United States Patent
Hohlig et al.

(10) Patent No.: US 12,188,021 B2
(45) Date of Patent: Jan. 7, 2025

(54) C5A BINDING NUCLEIC ACIDS

(71) Applicant: APTARION biotech AG, Berlin (DE)

(72) Inventors: Kai Hohlig, Berlin (DE); Axel Vater, Berlin (DE); Klaus Buchner, Berlin (DE); Christian Maasch, Berlin (DE); Sven Klussmann, Berlin (DE)

(73) Assignee: APTARION biotech AG, Berlin (DE)

( * ) Notice: Subject to any disclaimer, the term of this patent is extended or adjusted under 35 U.S.C. 154(b) by 0 days.

(21) Appl. No.: 17/982,469

(22) Filed: Nov. 7, 2022

(65) Prior Publication Data

US 2024/0384275 A1 Nov. 21, 2024

Related U.S. Application Data

(60) Continuation of application No. 16/819,102, filed on Mar. 15, 2020, now Pat. No. 11,492,625, which is a division of application No. 15/376,338, filed on Dec. 12, 2016, now Pat. No. 10,590,424, which is a continuation of application No. 14/371,006, filed as application No. PCT/EP2013/000056 on Jan. 10, 2013, now Pat. No. 9,518,265.

(30) Foreign Application Priority Data

Jan. 10, 2012 (EP) .................................. 12000106
Jan. 10, 2012 (WO) ................. PCT/EP2012/000089
Oct. 8, 2012 (EP) .................................. 12006960

(51) Int. Cl.
*C12N 15/115* (2010.01)
*A61K 31/7088* (2006.01)
*C07K 14/47* (2006.01)

(52) U.S. Cl.
CPC ........ *C12N 15/115* (2013.01); *A61K 31/7088* (2013.01); *C07K 14/472* (2013.01); *C12N 2310/16* (2013.01); *C12N 2310/344* (2013.01); *G01N 2333/4716* (2013.01)

(58) Field of Classification Search
None
See application file for complete search history.

(56) References Cited

U.S. PATENT DOCUMENTS

| | | | |
|---|---|---|---|
| 6,140,490 A | 10/2000 | Biesecker et al. | |
| 6,395,888 B1 | 5/2002 | Biesecker et al. | |
| 6,566,343 B2 | 5/2003 | Biesecker et al. | |
| 7,538,211 B2 | 5/2009 | Benedict et al. | |
| 7,579,456 B2 | 8/2009 | Benedict et al. | |
| 7,803,931 B2 | 9/2010 | Benedict et al. | |
| 7,964,572 B2 | 6/2011 | Biesecker et al. | |
| 8,507,456 B2 | 8/2013 | Purschke et al. | |
| 2003/0191084 A1 | 10/2003 | Biesecker et al. | |
| 2006/0018871 A1 | 1/2006 | Benedict et al. | |
| 2006/0105980 A1 | 5/2006 | Benedict et al. | |
| 2007/0048248 A1 | 3/2007 | Benedict et al. | |
| 2007/0116710 A1 | 5/2007 | Bell et al. | |
| 2009/0269356 A1 | 10/2009 | Epstein | |
| 2011/0046207 A1 | 2/2011 | Purschke et al. | |
| 2011/0060027 A1 | 3/2011 | Benedict et al. | |
| 2011/0196201 A1 | 8/2011 | Biesecker et al. | |
| 2012/0065254 A1 | 3/2012 | Jarosch et al. | |
| 2013/0165501 A1 | 6/2013 | Purschke et al. | |
| 2014/0350088 A1 | 11/2014 | Jarosch et al. | |
| 2015/0031755 A1 | 1/2015 | Schulzchen et al. | |
| 2015/0232852 A1 | 8/2015 | Purschke et al. | |

OTHER PUBLICATIONS

Vater et al., "Identification . . . aptamers," Mol Imm 47:2290, 2010.
Vater & Klussmann, "Toward . . . prospects," Curr Opn Drug Disc Dev 6:253-261, 2003.
Bunka et al., "Development . . . therapeutics," Curr Opn Pharm 10:557-562, 2010.
Ulrich, "RNA . . . therapy," Handbook Exp Pharm 173:305-326, 2006.
Kanwar et al., "Chimeric . . . delivery," Crit Rev Biochem Mol Biol 46:459-477, 2011.
Nimjee et al., "Aptamers . . . therapeutics," Ann Rev Med 56:555-583, 2005.
Eaton et al., "Post-SELEX . . . aptamers," Bioorg Med Chem 5:1087-1096, 1997.
Lee, "Interaction . . . Selex," Nar 30:5360-5368, 2002.
Trevino et al., "Evolution . . . heterogeneity," PNAS 108:13492-13497, 2011.
Biesecker et al., "Derivation . . . C5," Immunopharm 42:219-230, 1999.
Proctor et al., "Recent . . . inhibitors," Expert Opn Thera Patents 16:445-458, 2006.
Eulberg et al., "Development . . . antagonist," NAR 33(4)e45, 2005.
Eulberg & Klussmann, "Spiegelmers: Biostable Aptamers," ChemBioChem 4:979-983, 2003.

*Primary Examiner* — Sean McGarry
(74) *Attorney, Agent, or Firm* — MDIP LLC

(57) ABSTRACT

The present invention is related to a nucleic acid molecule capable of binding to human C5a, wherein the nucleic acid molecule comprises a central stretch of nucleotides, wherein the central stretch of nucleotides comprises a nucleotide sequence of 5' AUGn$_1$GGUGKUn$_2$n$_3$RGGGHUGUKGGGn$_4$Gn$_5$CGACGCA 3' [SEQ ID NO: 61], wherein n$_1$ is U or dU, n$_2$ is G or dG, n$_3$ is A or dA, n$_4$ is U or dU, n$_5$ is U or dU and G, A, U, C, H, K, and R are ribonucleotides, and dU, dG and dA are 2'-deoxyribonucleotides.

22 Claims, 26 Drawing Sheets
Specification includes a Sequence Listing.

| Name | SEQ ID NO. | Sequence: 5'-3' | KD [nM] mC5a | KD [nM] huC5a |
|---|---|---|---|---|
| 274-B5-002 | 001 | GCCUG AUGUGGUUGAAGGUUGUGGGUCGACGCA CAGGC | 3.5 | 12.1 |
| 274-D5-002 | 002 | GCCUG AUGUGGUUGAGGGUUGUGGGUCGACGCA CAGGC | 2.2 | 7.8 |
| 274-C8-002 | 003 | GCCUG AUGUGGUUGAAGGUUGUUGGGUCGACGCA CAGGC | 0.9 | 5.1 |
| 274-C8-002-G14 (=NOX-D19001) | 004 | GCCUG AUGUGGUUGAAGGGUUGUGGGUCGACGCA CAGGC | 0.3 | 1.4 |
| 274-C5-002 | 005 | GCCUG AUGUGGUUGAGGGUUGUGGGUCGACGCA CAGGC | 0.3 | 1.6 |
| 274-G6-002 | 006 | GCCUG AUGUGGUUGAGGGGAUGUGGGUCGACGCA CAGGC | 1.0 | 4.8 |
| 274-H6-002 | 007 | GCCUG AUGUGGUUGAGGGCUGUGGGUCGACGCA CAGGC | n.d. | n.d. | any of G, C, U and A is a ribonucleotide; nucleotides edged by □ represent a C5a-binding motif;
KD: Dissociation constant K_D of Spiegelmers (L-nucleic acid), molecules of the indicated sequence were tested as Spiegelmers (L-nucleic acid) measured as surface plasmon resonance on Biacore using direct binding to covalently immobilized human C5a (huC5a) or mouse C5a (mC5a)

Fig.1

| Name | SEQ ID NO. | Sequence: 5'-3' | KD [nM] huC5a |
|---|---|---|---|
| NOX-D19001 | 004 | GCCUG|AUGUGGUGGUGAAGGUUGGGUUGGGUGUCGACGCA|CAGGC | 1.38 |
| NOX-D19001-D09 | 008 | GCCUG|AUGdUGUGGUGAAGGUUGGGUUGGGUGUCGACGCA|CAGGC | 0.71 |
| NOX-D19001-D16 | 009 | GCCUG|AUGUGGUGdGAAGGUUGGGUUGGGUGUCGACGCA|CAGGC | 1.03 |
| NOX-D19001-D17 | 010 | GCCUG|AUGUGGUGGUGdAAGGUUGGGUUGGGUGUCGACGCA|CAGGC | 0.91 |
| NOX-D19001-D30 | 011 | GCCUG|AUGUGGUGGUGAAGGUUGGGUUGGGdUGUCGACGCA|CAGGC | 0.77 |
| NOX-D19001-D32 | 012 | GCCUG|AUGUGGUGGUGAAGGUUGAAGGUUGGGUGdUCGACGCA|CAGGC | 0.92 |
| NOX-D19001-D40 | 013 | GCCUG|AUGUGGUGGUGAAGGUUGGGUUGGGUGUCGACGCA|dCAGGC | 0.88 | any of G, C, U and A is a ribonucleotide;     any of dG, dC, dU and dA is a 2'-desoxyribonucleotide;

nucleotides edged by ☐ represent a C5a-binding motif;

KD: Dissociation constant $K_D$ of Spiegelmers (L-nucleic acid), molecules of the indicated sequence were tested as Spiegelmers (L-nucleic acid) measured as surface plasmon resonance on Biacore using direct binding to covalently immobilized human C5a (huC5a)

Fig. 2

| Name | SEQ ID NO. | Sequence: 5'-3' | KD [nM] |
|---|---|---|---|
| 2 RNA-to-DNA substitutions: | | | |
| NOX-D19001-D09-30 | 014 | GCCUGAUGdUGGUGGUGAAGGUUGUUGGdGUGUCGACGCACAGGC | 0.461 |
| NOX-D19001-D09-32 | 015 | GCCUGAUGdUGGUGGUGAAGGUUGUUGGdGUGUCGACGCACAGGC | 0.566 |
| NOX-D19001-D09-40 | 016 | GCCUGAUGdUGGUGGUGAAGGUUGUUGGGUGUCGACGCAdCAGGC | 0.570 |
| NOX-D19001-D09-32 | 017 | GCCUGACGUGGUGGUGAAGGUUGUUGGdGUdUCGACGCACAGGC | 0.855 |
| NOX-D19001-D30-40 | 018 | GCCUGAUGUGGUGGUGAAGGUUGUUGGdGUGUCGACGCAdCAGGC | 0.624 |
| NOX-D19001-D32-40 | 019 | GCCUGAUGUGGUGGUGAAGGUUGUUGGGUGUCGACGCAdCAGGC | 0.652 |
| 3 RNA-to-DNA substitutions: | | | |
| NOX-D19001-D09-30-32 | 020 | GCCUGAUGdUGGUGGUGAAGGUUGUUGGdGUdUCGACGCACAGGC | 0.526 |
| NOX-D19001-D09-30-40 | 021 | GCCUGAUGdUGGUGGUGAAGGUUGUUGGdGUGUCGACGCAdCAGGC | 0.400 |
| NOX-D19001-D09-32-40 | 022 | GCCUGAUGdUGGUGGUGAAGGUUGUUGGGUGdUCGACGCAdCAGGC | 0.448 |
| NOX-D19001-D30-32-40 | 023 | GCCUGAUGUGGUGGUGAAGGUUGUUGGdGUdUCGACGCAdCAGGC | 0.880 |
| 4 RNA-to-DNA substitutions: | | | |
| NOX-D19001-D09-30-32-40 | 024 | GCCUGAUGdUGGUGGUGAAGGUUGUUGGdGUdUCGACGCAdCAGGC | 0.385 |
| 5 RNA-to-DNA substitutions: | | | |
| NOX-D19001-D09-16-30-32-40 | 025 | GCCUGAUGdUGGUdGGUGAAGGUUGUUGGdGUdUCGACGCAdCAGGC | 0.351 |
| NOX-D19001-D09-17-30-32-40 | 026 | GCCUGAUGdUGGUGdGUGAAGGUUGUUGGdGUdUCGACGCAdCAGGC | 0.308 |
| 6 RNA-to-DNA substitutions: | | | |
| NOX-D19001-D09-16-17-30-32-40 (= NOX-D19001-6xDNA) | 027 | GCCUGAUGdUGGUdGdGUGAAGGUUGUUGGdGUdUCGACGCAdCAGGC | 0.36 |

Fig. 3 any of G, C, U and A is a ribonucleotide; any of dG, dC, dU and dA is a 2'-desoxyribonucleotide; nucleotides edged by ☐ represent a C5a-binding motif;

KD: Dissociation constant $K_D$ of Spiegelmers (L-nucleic acid), molecules of the indicated sequence were tested as Spiegelmers (L-nucleic acid) measured as surface plasmon resonance on Biacore using direct binding to covalently immobilized human C5a (huC5a)

Fig. 3 continuation

| Name | SEQ ID NO. | Sequence: 5'-3' | nt | KD [nM] huC5a |
|---|---|---|---|---|
| NOX-D19001-6xDNA | 027 | GCCUGAUGdUGGUGdAAGGUUGdGdUGdUCGACGCAdCAGGC | 44 | 0.36 |
| NOX-D19001-6xDNA-007 | 028 | CCUGAUGdUGGUGdAAGGUUGdGdUGdUCGACGCAdCAGGC | 43 | 0.46 |
| NOX-D19001-6xDNA-008 | 029 | CUGAUGdUGGUGdAAGGUUGdGdUGdUCGACGCAdCAGGC | 42 | 0.57 |
| NOX-D19001-6xDNA-009 | 030 | UGAUGdUGGUGdAAGGUUGdGdUGdUCGACGCAdCAGGC | 41 | 3.51 |
| NOX-D19001-6xDNA-010 | 031 | GAUGdUGGUGdAAGGUUGdGdUGdUCGACGCAdCAGGC | 40 | 6.89 |
| NOX-D19001-6xDNA-011 | 032 | GCUGAUGdUGGUGdAAGGUUGdGdUGdUCGACGCAdCAGC | 42 | 0.34 |
| NOX-D19001-6xDNA-012 | 033 | GUGAUGdUGGUGdAAGGUUGdGdUGdUCGACGCAdCAC | 40 | 0.81 |
| NOX-D19001-6xDNA-013 | 034 | UGAUGdUGGUGdAAGGUUGdGdUGdUCGACGCAdCA | 38 | 8.22 |
| NOX-D19001-6xDNA-018 | 035 | GCCGAUGdUGGUGdAAGGUUGdGdUGdUCGACGCAdCGGC | 42 | 0.30 |
| NOX-D19001-6xDNA-019 | 036 | GGCGAUGdUGGUGdAAGGUUGdGdUGdUCGACGCAdCGCC | 42 | 0.24 |
| NOX-D19001-6xDNA-020 (=NOX-D20001) | 037 | GCGAUGdUGGUGdAAGGUUGdGdUGdUCGACGCAdCGC | 40 | 0.42 |
| NOX-D19001-6xDNA-021 | 038 | CUGAUGdUGGUGdAAGGUUGdGdUGdUCGACGCAdCAGC | 41 | 0.70 |
| NOX-D19001-6xDNA-022 | 039 | UGAUGdUGGUGdAAGGUUGdGdUGdUCGACGCAdCAGC | 40 | 3.27 | any of G, C, U and A is a ribonucleotide;  any of dG, dC, dU and dA is a 2'-desoxyribonucleotide;

nucleotides edged by ☐ represent a C5a-binding motif;  nt.: number of nucleotides;

KD: Dissociation constant $K_D$ of Spiegelmers (L-nucleic acid), molecules of the indicated sequence were tested as Spiegelmers (L-nucleic acid) measured as surface plasmon resonance on Biacore using direct binding to covalently immobilized human C5a (huC5a)

Fig. 4A

| Name | SEQ ID NO. | Sequence: 5'-3' | nt | KD [nM] huC5a |
|---|---|---|---|---|
| NOX-D19001-6xDNA | 027 | GCCUG AUGdUGGUdGdAAGGUUGGGdUGdUUGGdUCGACGCA dCAGGC | 44 | 0.42 |
| NOX-D19001-6xDNA-023 | 040 | CG AUGdUGGUdGdAAGGUUGGGdUGdUUGGdUCGACGCA dCAGC | 40 | 9.38 |
| NOX-D19001-6xDNA-024 | 041 | G AUGdUGGUdGdAAGGUUGGGdUGdUUGGdUCGACGCA dCAGC | 39 | 8.29 |
| NOX-D19001-6xDNA-025 | 042 | GCUG AUGdUGGUdGdAAGGUUGGGdUGdUUGGdUCGACGCA dCAC | 41 | 5.01 |
| NOX-D19001-6xDNA-026 | 043 | GCUG AUGdUGGUdGdAAGGUUGGGdUGdUUGGdUCGACGCA dCC | 40 | 16.8 |
| NOX-D19001-6xDNA-027 | 044 | GCUG AUGdUGGUdGdAAGGUUGGGdUGdUUGGdUCGACGCA dCA | 40 | 4.71 |
| NOX-D19001-6xDNA-028 | 045 | CG AUGdUGGUdGdAAGGUUGGGdUGdUUGGdUCGACGCA dCGC | 39 | 3.36 |
| NOX-D19001-6xDNA-029 | 046 | G AUGdUGGUdGdAAGGUUGGGdUGdUUGGdUCGACGCA dCGC | 38 | 6.89 |
| NOX-D19001-6xDNA-030 | 047 | GCG AUGdUGGUdGdAAGGUUGGGdUGdUUGGdUCGACGCA dCC | 39 | 16.1 |
| NOX-D19001-6xDNA-032 | 048 | GCG AUGdUGGUdGdAAGGUUGGGdUGdUUGGdUCGACGCA dC | 38 | 5.58 |
| NOX-D19001-6xDNA-033 | 049 | GG AUGdUGGUdGdAAGGUUGGGdUGdUUGGdUCGACCGCA dCC | 38 | 5.47 | any of G, C, U and A is a ribonucleotide; any of dG, dC, dU and dA is a 2'-desoxyribonucleotide;

nucleotides edged by ☐ represent a C5a-binding motif; nt.: number of nucleotides;

KD: Dissociation constant $K_D$ of Spiegelmers (L-nucleic acid), molecules of the indicated sequence were tested as Spiegelmers (L-nucleic acid) measured as surface plasmon resonance on Biacore using direct binding to covalently immobilized human C5a (huC5a)

Fig. 4B

| Name | SEQ ID NO. | Sequence: 5'-3' | KD [nM] | IC50 [nM] |
|---|---|---|---|---|
| NOX-D19001-020 | 55 | GCGAUGUGGUGAAGGUUGUUGGGUGUCGACGCACGC | 11.3 | 9.4 |
| 1 RNA-to-DNA substitutions: | | | | |
| NOX-D19001-1xDNA-020 | 56 | GCGAUGdUGGUGAAGGUUGUUGGGUGUCGACGCACGC | 1.34 | 3 |
| 2 RNA-to-DNA substitutions: | | | | |
| NOX-D19001-2xDNA-020 | 57 | GCGAUGdUGGUGAAGGUUGUUGGGdUGUCGACGCACGC | 0.73 | 2.2 |
| 3 RNA-to-DNA substitutions: | | | | |
| NOX-D19001-3xDNA-020 | 58 | GCGAUGdUGGUGAAGGUUGUUGGGdUGUCGACGCACGC | 0.91 | 3.7 |
| NOX-D19001-2dU-1dC-020 (=NOX-D21001) | 59 | GCGAUGdUGGUGAAGGUUGUUGGGdUGUCGACGCAdCGC | 0.82 | 0.6 |
| 4 RNA-to-DNA substitutions: | | | | |
| NOX-D19001-3dU-1dC-020 | 60 | GCGAUGdUGGUGAAGGUUGUUGGGdUGUCGACGCAdCGC | 0.87 | 0.6 | any of G, C, U and A is a ribonucleotide; any of dG, dC, dU and dA is a 2'-desoxyribonucleotide;

nucleotides edged by ☐ represent a C5a-binding motif;

$K_D$: Dissociation constant $K_D$ of Spiegelmers (L-nucleic acid) measured as surface plasmon resonance on Biacore using direct binding to covalently immobilized human C5a (huC5a) (L-nucleic acid), molecules of the indicated sequence were tested as Spiegelmers $IC_{50}$: Half maximal inhibitory concentration (IC50) of Spiegelmers (L-nucleic acid), molecules of the indicated sequence were tested as Spiegelmers in a cell culture *in vitro* taxis assy to inhibit C5a

Fig. 5

| NOX-D20 binding to: | $K_D$ [pM] |
|---|---|
| mouse C5a | 19.1 |
| human C5a | 299 |
| rat C5a | -- |
| rhesus monkey C5a | -- |

Fig. 8 continuation

Alignment of C5a from selected species

```
human:   TLQKKIEEIAAKYKHSVVKKCCYDGACVNNDETCEQRAARISLGPRCIKAFTECCVVASQLRANISHKDMQLGR
[SEQ ID NO: 050]

rhesus:  MLQEKIEEIAAKYKHLVVKKCCYDGVRINHDETCEQRAARISVGPRCVKAFTECCVVASQLRANNSHKDLQLGR
[SEQ ID NO: 054]

mouse:   NLHLLRQKIEEQAAKYKHSVPKKCCYDGARVNFYETCEERVARVTIGPLCIRAFNECCTIANKIRKESPHKPVQLGR
[SEQ ID NO: 052]

rat:     DLQLLHQKVEEQAAKYKHRVPKKCCYDGARENKYETCEQRVARVTIGPHCIRAFNECCTIADKIRKESHHKGMLLGR
[SEQ ID NO: 051]
```

Fig. 11

C5A BINDING NUCLEIC ACIDS

The application contains a Sequence Listing which was submitted electronically in .XML format. Said Sequence Listing is incorporated herein by reference in entirety. Said .XML copy was created on 23 Jan. 2024, is named 021315-08772308.xml and is 354,457 bytes in size. Said XML form of the Sequence Listing is a substantive copy of previously filed Sequence Listings in paper and in computer readable form and is part of the instant specification.

The present invention is related to a nucleic acid molecule capable of a binding to C5a and/C5, the use thereof for the manufacture of a medicament, a diagnostic agent, and a detecting agent, respectively, a composition comprising said nucleic acid molecule, a complex comprising said nucleic acid molecule, a method for screening of an antagonist of an activity mediated by C5a and/C5 using said nucleic nucleic acid molecule, and a method for the detection of said nucleic acid molecule.

The primary structure of the human anaphylatoxin C5a (complement factor 5a; SwissProt entry P01031) was determined in 1978 (Fernandez & Hugh 1978). It consists of 74 amino acids accounting for a molecular weight of 8,200 Da while the carbohydrate portion accounts for approximately 3,000 Da. The carbohydrate portion of C5a exists as a single complex oligosaccharide unit attached to an asparagine at position 64. The three disulfide bonds confer a stable, rigid structure to the molecule.

Although the three-dimensional structure of C5a forms from different mammalian species has generally been maintained, the amino acid sequence has not particularly well been conserved during evolution Sequence alignment demonstrates 64% overall sequence identity of human and mouse C5a. Human C5a shares the following percentages of identical amino acids with C5a from:

Macaca mulatta (rhesus monkey) 85%
Macaca fascicularis (cynomolgus monkey) 85%
Bos taurus (bovine) 69%
Sus scrofa (pig) 68%
Mus musculus (mouse) 64%
Rattus norvegicus (rat) 61%

Besides the limited sequence homology, glycosylation is also heterogeneous. While human C5a is glycosylated on asparagine 64, the murine homologue is not glycosylated at all. The more distantly related human proteins C3a and C4a share only 35 and 40%, respectively, identity with C5a.

The complement system was discovered at the beginning of the last century as a heat sensitive serum fraction that "complemented" the antisera mediated lysis of cells and bacteria. Being a humoral component of the natural unspecific (innate) immune response, it plays an essential role in host defence against infectious agents and in the inflammatory process. Complement can be activated via three distinct pathways (i) after an antibody attaches itself to a cell surface or bacteria (referred as classical pathway), (ii) directly by bacterial or viral glycolipids (referred as alternative pathway), or (iii) by carbohydrates on bacteria (referred as lectin pathway). All these activation pathways converge at the point of activation of the complement components C3 and C5, where the common terminal pathway starts, culminating in assembly of the membrane attack complex (abbr. MAC). The complement system consists of more than 20 soluble proteins that function either as proteolytic enzymes or as binding proteins and making up about 10% of the total globulins in vertebrate serum. In addition, the complement system includes multiple distinct cell-surface receptors that exhibit specificity for proteolytic fragments of complement proteins and that are expressed by inflammatory cells and cells regulating the adaptive immune response. There are several regulatory proteins that inhibit complement activation and thus protect host cells from accidental complement attack. The complement system can become activated independently or together with the adaptive immune response.

The functions of complement include the process of opsonization (i.e. making bacteria more susceptible to phagocytosis), lysis of bacteria and foreign cells by inserting a pore into their membrane (referred as membrane attack complex), generation of chemotactically active substances, increase of vascular permeability, evocation of smooth muscle contraction, and promotion of mast cell degranulation. Similar to the coagulation cascade, the process of complement activation is organized in sequential enzymatic steps also known as an enzymatic cascade (Sim and Laich, 2000). The detailed sequence of these interactions is outlined in the following.

Classical Pathway. This antibody-dependent activation pathway complements the specific antibody response. It is as elaborately controlled as the alternative pathway, but lacks the spontaneous initiation ability; i.e. the antibody-independent recognition function, and the feedback amplification mechanism. Among the activators of the classical pathway are antigen-antibody complexes, β-amyloid, DNA, polyinosinic acid, polyanion-polycation complexes like heparin/protamine, some enveloped viruses, monosodium urate crystals, lipid A of bacterial cell walls, plicatic acid, ant venom polysaccharide, subcellular membranes (such as mitochondria), as well as cell- and plasma-derived enzymes such as plasmin, kallikrein, activated Hageman factor, elastase or cathepsins. The antibody-induced classical pathway starts with C1, which binds to the Fc-fragment of an antibody (IgM>IgG3>IgG1>>IgG2) ligated to a cell surface antigen. C1 is a recognition complex composed of 22 polypeptide chains in 3 subunits; C1q, C1r, C1s. C1q is the actual recognition portion, a glycoprotein containing a collagen-like domain (exhibiting hydroxyproline and hydroxylysine residues) that looks like a bunch of tulips. Upon binding via C1q, C1r is activated to become a protease that cleaves C1s to a form that activates (by cleavage) both C2 and C4 to C2a/b and C4a/b. C2a and C4b combine to produce C4b2a, the C3 convertase (C3 activating enzyme). C4a has only weak anaphylatoxin activity but is not chemotactic. C3 is central to all three activation pathways. In the classical pathway, C4b2a convertase cleaves C3 into C3a/b. C3a is an anaphylatoxin. C3b combines with C4b2a to form C4b2a3b complex (C5 convertase). C3b can also bind directly to cells making them susceptible to phagocytosis (opsonization).

Alternative pathway. This pathway does not require antibodies for activation and is of major importance in host defence against bacterial and viral infection because—unlike the classical pathway—it is directly activated by surface structures of invading microorganisms such as bacterial/viral glycolipids or endotoxins. Other activators are inulins, rabbit erythrocytes, desialylated human erythrocytes, cobra venom factor, or phosphorothioate oligonucleotides.

The six proteins C3, Factors B, D, H, I, and properdin together perform the functions of initiation, recognition and activation of the pathway which results in the formation of activator-bound C3/C5 convertase. The cascade begins with C3. A small amount of C3b is always found in circulation as a result of spontaneous cleavage of C3 ("C3-tickover"), but the concentrations are generally kept very low by subsequent degradation. However, when C3b binds to sugars on a cell surface, it can serve as a nucleus for alternative pathway activation. Then Factor B binds to C3b. In the presence of Factor D, bound Factor B is cleaved to Ba and Bb; Bb contains the active site for a C3 convertase. Next, properdin binds to C3bBb to stabilize the C3bBb convertase on the cell surface leading to cleavage of further C3 molecules. Finally, the alternative C5 convertase C3bBb3b forms which cleaves C5 to C5a/b. Once present, C5b initiates assembly of the membrane attack complex as described above. Generally, only Gram-negative cells can be directly lysed by antibody plus complement; Gram-positive cells are mostly resistant. However, phagocytosis is greatly enhanced by opsonization with C3b (phagocytes have C3b receptors on their surface) and antibody is not always required. In addition, complement can neutralize virus particles either by direct lysis or by preventing viral penetration of host cells.

Lectin pathway. The most recently discovered lectin or mannan-binding lectin (abbr. MBL) pathway depends on innate recognition of foreign substances (i.e., bacterial surfaces). This pathway has structural and functional similarities to the classical pathway. Activation of the lectin pathway is initiated by the acute phase protein MBL, which recognizes mannose on bacteria, IgA and probably structures exposed by damaged endothelium. MBL is homologous to C1q and triggers the MBL associated serine proteases (abbr. MASPs), of which the three forms MASP1, MASP2 and MASP3 have been described. Further lectin pathway activation is virtually identical to classical pathway activation forming the same C3 and C5 convertases. In addition there is some evidence that MASPs under some conditions may activate C3 directly.

Terminal pathway. All three activation pathways converge in the formation of C5 convertase (C4b2a3b in the classical and lectin pathway, C3bBb3b in the alternative pathway), which cleaves C5 to C5a/b. C5a has potent anaphylatoxin activity and is chemotactic. The other C5 fragment C5b functions with its hydrophobic binding site as an anchor on the target cell surface to which the lytic membrane attack complex (MAC or terminal complement complex, abbr. TCC) forms. The MAC is assembled from five precursor proteins: C5b, C6, C7, C8, and C9. The final event is the formation of C9 oligomers, which insert themselves as transmembrane channels into the plasma membrane leading to osmotic lysis of the cell. MAC assembly is controlled by the soluble plasma factors S protein (also known as vitronectin) and SP-40,40 (also so known as clusterin), and by CD59 and HRF (homologous restriction factor) on host cell membranes. Many kinds of cells are sensitive to complement mediated lysis: erythrocytes, platelets, bacteria, viruses possessing a lipoprotein envelope, and lymphocytes.

The complement system is a potent mechanism for initiating and amplifying inflammation. This is mediated through fragments of the complement components. Anaphylatoxins are the best defined fragments and are proteolytic fragments of the serine proteases of the complement system: C3a, C4a and C5a. Anaphylatoxins are not only produced in the course of complement activation, but also from activation of other enzyme systems which may directly cleave C3, C4 and C5. Such enzymes include thrombin, plasmin, kallikrein, tissue and leukocyte lysosomal enzymes, and bacterial proteases. The anaphylatoxins have powerful effects on blood vessel walls, causing contraction of smooth muscle (e.g. ileal, bronchial, uterine and vascular muscle) and an increase in vascular permeability. These effects show specific tachyphylaxis (i.e. repeated stimulation induces diminishing responses) and can be blocked by antihistamines; they are probably mediated indirectly via release of histamine from mast cells and basophils. C5a is the 74-amino acid N-terminal cleavage product of the C5 plasmaprotein a chain. It is bound by the receptor C5aR (also known as C5R1 or CD88) with high affinity, a molecule present on many different cell types: most prominently on neutrophils, macrophages, smooth muscle cells, and endothelial cells. C5a is by far the most powerful anaphylatoxin, approximately 100 times more effective than C3a, and 1000 times more effective than C4a. This activity decreases in the order C5a>histamine>acetylcholine>C3a>>C4a.

C5a is extremely potent at stimulating neutrophil chemotaxis, adherence, respiratory burst generation and degranulation. C5a also stimulates neutrophils and endothelial cells to present more adhesion molecules; the intravenous injection of C5a, for example, quickly leads to neutropenia in animal experiments by triggering adherence of neutrophils to the blood vessel walls. Ligation of the neutrophil C5a receptor is followed by mobilization of membrane arachidonic acid which is metabolized to prostaglandins and leukotrienes including LTB4, another potent chemoattractant for neutrophils and monocytes. Following ligation of monocyte C5a receptors, IL-1 is released. Thus, the local release of C5a at sites of inflammation results in powerful pro-inflammatory stimuli. In fact, the release of C5a is connected directly or indirectly with many acute or chronic conditions, such as immune complex associated diseases in general (Heller et al., 1999); asthma (Kohl, 2001); septic shock (Huber-Lang et al., 2001); systemic inflammatory response syndrome (abbr. SIRS); multiorgan failure (abbr. MOF); acute respiratory distress syndrome (abbr. ARDS); inflammatory bowel syndrome (abbr. IBD) (Woodruff et al., 2003); infections; severe burns (Piccolo et al., 1999); reperfusion injury of organs such as heart (van der Pals et al. 2010), spleen, bladder, pancreas, stomach, lung, liver, kidney, limbs, brain, sceletal muscle or intestine (Riley et al., 2000); psoriasis (Bergh et al., 1993); myocarditis; multiple sclerosis (Muller-Ladner et al., 1996); and rheumatoid arthritis (abbr.RA) (Woodruff et al., 2002). Numerous overviews over the relation between the complement system and diseases are published (Kirschfink, 1997; Kohl, 2001; Makrides, 1998; Walport, 2001a; Walport, 2001b).

Cell injury by complement occurs as a consequence of activation of either the classical or the alternative pathway on the surface of a cell. The MAC constitutes a supramolecular organisation that is composed of approximately twenty protein molecules and representing a molecular weight of approx. 1.7 million Da. The fully assembled MAC contains one molecule each of C5b, C6, C7, and C8 and several molecules of C9. All these MAC components are glycoproteins. When C5 is cleaved by C5 convertase and C5b is produced, self-assembly of the MAC begins. C5b and C6 form a stable and soluble bimolecular complex which binds to C7 and induces it to express a metastable site through which the nascent trimolecular complex (C5b-7) can insert itself into membranes, when it occurs on or in close proximity to a target lipid bilayer. Insertion is mediated by hydrophobic regions on the C5b-7 complex that appear following C7 binding to C5b-6. Membrane-bound C5b-7 commits MAC assembly to a membrane site and forms the receptor for C8. The binding of one C8 molecule to each C5b-7 complex gives rise to small trans-membrane channels of less than 1 nm functional diameter that may perturb target bacterial and erythrocyte membranes. Each membrane-bound C5b-8 complex acts as a receptor for multiple C9 molecules and appears to facilitate insertion of C9 into the hydrocarbon core of the cell membrane. Binding of one molecule of C9 initiates a process of C9 oligomerisation at the membrane attack site. After at least 12 molecules are incorporated into the complex, a discrete channel structure is formed. Therefore the end product consists of the tetramolecular C5b-8 complex (with a molecular weight of approximately 550 kDa) and tubular poly-C9 (with a molecular weight of approximately 1,100 kDa). This form of the MAC, once inserted into the cell membranes, creates complete transmembrane channels leading to osmotic lysis of the cell. The transmembrane channels formed vary in size depending on the number of C9 molecules incorporated into the channel structure. Whereas the presence of poly-C9 is not absolutely essential for the lysis of red blood cells or of nucleated cells, it may be necessary for the killing of bacteria.

The complement system is primarily beneficial in the body's defense against invading microorganisms. The early components of the complement cascade are important for opsonization, of infectious agents followed by their elimination from the body. In addition, they serve several normal functions of the immune system like controlling formation and clearance of immune complexes or cleaning up debris, dead tissues and foreign substances. All three activation pathways which recognize different molecular patterns that (in the healthy body) define an extensive array of non-self structures help controlling invaders. The terminal complement pathway—which culminates in the assembly of the MAC—represents a further line of defense by lysing bacteria and foreign cells.

The importance of a functional complement system becomes clear when the effects of complement deficiencies are considered. For example, individuals that are missing one of the alternative pathway proteins or late components (C3-C9) tend to get severe infections with pyogenic organisms, particularly *Neisseria* species. Deficiencies in the classical pathway components (such as C1, C2, C4) are also associated with increased, though not as strongly elevated, risk of infection. Complement components like C1 and MBL do also have the ability to neutralize viruses by interfering with the viral interaction with the host cell membrane, thus preventing entrance into the cell.

Of note, although cleavage of C5 leads to C5a as well as the MAC, the clinical features of C5 deficiency do not differ markedly from those of other terminal component deficiencies (e.g. C6, C7, C8, C9) suggesting that the absence of C5 does not contribute significantly to the clinical picture in C5-deficient patients. Therefore, the selective antagonisation of C5a promises to be the optimal leverage, so that the normal up- and downstream disease-preventing functions of complement remain intact. Thus, only the deleterious overproduction of the proinflammatory anaphylatoxin is blocked.

The fact that C5aR-deficient mice—although they are more susceptible for infections with *Pseudomonas aeruginosa*—appear otherwise normal, suggests that the blockade of C5a function does not have deleterious effects.

Several compounds targeting C5a or C5 or the respective receptor are known and were successfully tested in in vivo models. Some of them have been further tested in clinical trials.

The C5-specific humanized antibody, eculizumab is approved for paroxysmal nocturnal hemoglobinuria and has shown efficacy in treating atypical haemolytic uraemic syndrome (aHUS), acute antibody-mediated kidney allograft rejection and cold agglutinin disease. It prevents cleavage of C5 and inhibits the action of both C5a and C5b. Besides similar research-stage C5 antibodies and antibody fragments, antibodies that selectively disrupt C5a:C5aR (CD88) interaction and leaves C5 cleavage and C5b-dependent MAC-formation unaffected are of special interest. Examples are the humanized anti-C5a mAb MEDI-7814 that is in Phase I clinical development for the potential iv treatment of inflammatory disorders and tissue injury and the C5a antibody TNX-558 for which however no development has been reported since 2007. An antibody to the C5a receptor, neutrazumab, is under development for rheumatoid arthritis and stroke (Ricklin & Lambris 2007; Wagner & Frank 2010).

A PEGylated anti-C5 aptamer (ARC-1905) is in preclinical development for AMD. CCX168 is a small molecule C5aR inhibitor currently in Phase II clinical development for anti-neutrophil cytoplasmic autoantibody-associated vasculitides (ChemoCentryx Press Release Oct. 17, 2011). Another C5aR antagonist in clinical development is MP-435 for the treatment of rheumatoid arthritis.

No development has been reported for the small molecule/peptidomimetic C5a receptor antagonists JPE-1375, JSM-7717 recently (Ricklin & Lambris 2007). Another inhibitor of the C5a receptor CD88, the cyclic hexapeptide PMX53, has been efficacious in inflammatory animal models, but has not met endpoints in placebo-controlled double-blind clinical studies in patients with rheumatoid arthritis. The clinical development for AMD has also been discontinued (Wagner & Frank 2010). A research-stage variant of PMX53, PMX205, has been published to be active in a murine model of Alzheimer's dementia (Fonseca et al. 2009). A further clinical stage compound is the C5a receptor (C5aR) antagonist, CCX-168. A Phase I trial has been initiated initiated for inflammatory and autoimmune diseases in January 2010.

Beside the effects of C5a as described supra, new data let assume that the generation of C5a in a tumor microenvironment enhance tumor growth by the suppression the antitumor CD8+ T-cell-mediated response, whereby said suppression seems to be associated with the recruitment of myeloid-derived suppressor cells into tumors and augmentation of their T-cell-directed suppressive abilities. Markiewski et al. showed that a blockade of the C5a receptors by a peptidic C5a receptor antagonist led to a retarded tumor growth in a mouse model (Markiewski et al., 2008).

Most of peptidic compounds are prone to degradation and modification by peptidases and additionally show a fast clearance rate from the body, preferably the human body. Thus, these peptidic compounds cannot be considered as drug-like molecules, a prerequisite for the development of drugs in general to be marketed.

Several Spiegelmers specifically binding to human C5a, but not to C5a of other species, were developed in the past (see WO2009/040113 and WO2010/108657).

Because for pre-clinical and clinical development animal models are essential, the problem underlying the present invention is to provide a compound which interacts with mouse C5a. More specifically, the problem underlying the present invention is to provide for a compound which interacts with both mouse C5a and human C5a.

A further problem underlying the present invention is to provide a compound for the manufacture of a medicament for the treatment of a human, and/or non-human diseases, whereby the disease is characterized by C5a being either directly or indirectly involved in the pathogenetic mechanism of such disease.

A still further problem underlying the present invention is to provide a compound for the manufacture of a diagnostic agent for the treatment of a disease, whereby the disease is characterized by C5a being either directly or indirectly involved in the pathogenetic mechanism of such disease.

These and other problems underlying the present invention are solved by the subject matter of the attached independent claims. Preferred embodiments may be taken from the dependent claims.

The problem underlying the present invention is solved in a first aspect, which is also the first embodiment of the first aspect, by a nucleic acid molecule capable of binding to human C5a, wherein the nucleic acid molecule comprises a central stretch of nucleotides, wherein the central stretch of nucleotides comprises a nucleotide sequence of

[SEQ ID NO: 61]
5' AUGn$_1$GGUGKUn$_2$n$_3$RGGGHUGUKGGGn$_4$Gn$_5$CGACGCA 3', wherein
 n$_1$ is U or dU, n$_2$ is G or dG, n$_3$ is A or dA, n$_4$ is U or dU, n$_5$ is U or dU and
 G, A, U, C, H, K, and R are ribonucleotides, and
 dU, dG and dA are 2'-deoxyribonucleotides.

In a second embodiment of the first aspect which is also an embodiment of the first embodiment of the first aspect, the central stretch of nucleotides comprises a nucleotide sequence selected from the group of

[SEQ ID NO: 62]
a) 5' AUGn$_1$GGUGUUn$_2$n$_3$AGGGUUGUGGGGn$_4$Gn$_5$CGACGCA 3',

[SEQ ID NO: 63]
b) 5' AUGn$_1$GGUGUUn$_2$n$_3$GGGGUUGUGGGGn$_4$Gn$_5$CGACGCA 3',

[SEQ ID NO: 64]
c) 5' AUGn$_1$GGUGUUn$_2$n$_3$AGGGUUGUUGGGn$_4$Gn$_5$CGACGCA 3',

[SEQ ID NO: 65]
d) 5' AUGn$_1$GGUGGUn$_2$n$_3$AGGGUUGUUGGGn$_4$Gn$_5$CGACGCA 3',

[SEQ ID NO: 66]
e) 5' AUGn$_1$GGUGGUn$_2$n$_3$GGGGUUGUGGGGn$_4$Gn$_5$CGACGCA 3',

[SEQ ID NO: 67]
f) 5' AUGn$_1$GGUGGUn$_2$n$_3$GGGGAUGUGGGGn$_4$Gn$_5$CGACGCA 3', and

[SEQ ID NO: 68]
g) 5' AUGn$_1$GGUGUUn$_2$n$_3$GGGGCUGUGGGGn$_4$Gn$_5$CGACGCA 3', wherein
 n$_1$ is U or dU, n$_2$ is G or dG, n$_3$ is A or dA, n$_4$ is U or dU, n$_5$ is U or dU and
 G, A, U and C are ribonucleotides, and
 dU, dG and dA are 2'-deoxyribonucleotides.

In a third embodiment of the first aspect which is also an embodiment of the second embodiment of the first aspect, the central stretch of nucleotides comprises a nucleotide sequence of

[SEQ ID NO: 65]
5' AUGn$_1$GGUGGUn$_2$n$_3$AGGGUUGUUGGGn$_4$Gn$_5$CGACGCA 3' n$_1$ is U or dU, n$_2$ is G or dG, n$_3$ is A or dA, n$_4$ is U or dU, n$_5$ is U or dU and
 G, A, U and C are ribonucleotides, and
 dU, dG and dA are 2'-deoxyribonucleotides.

In a fourth embodiment of the first aspect which is also an embodiment of the third embodiment of the first aspect, the central stretch of nucleotides comprises a nucleotide sequence selected from the group of

[SEQ ID NO: 73]
a) 5' AUGdUGGUGGUGAAGGGUUGUUGGGUGUCGACGCA 3',

[SEQ ID NO: 74]
b) 5' AUGUGGUGGUdGAAGGGUUGUUGGGUGUCGACGCA 3',

[SEQ ID NO: 75]
c) 5' AUGUGGUGGUGdAAGGGUUGUUGGGUGUCGACGCA 3',

[SEQ ID NO: 76]
d) 5' AUGUGGUGGUGAAGGGUUGUUGGGdUGUCGACGCA 3',

[SEQ ID NO: 77]
e) 5' AUGUGGUGGUGAAGGGUUGUUGGGUGdUCGACGCA 3',

[SEQ ID NO: 78]
f) 5' AUGdUGGUGGUGAAGGGUUGUUGGGdUGUCGACGCA 3',

[SEQ ID NO: 79]
g) 5' AUGdUGGUGGUGAAGGGUUGUUGGGUGdUCGACGCA 3',

[SEQ ID NO: 80]
h) 5' AUGUGGUGGUGAAGGGUUGUUGGGdUGdUCGACGCA 3',

[SEQ ID NO: 81]
i) 5' AUGdUGGUGGUGAAGGGUUGUUGGGdUGdUCGACGCA 3',

[SEQ ID NO: 82]
j) 5' AUGdUGGUGGUdGAAGGGUUGUUGGGdUGdUCGACGCA 3'

[SEQ ID NO: 83]
k) 5' AUGdUGGUGGUGdAAGGGUUGUUGGGdUGdUCGACGCA 3',

[SEQ ID NO: 84]
l) 5' AUGdUGGUGGUdGdAAGGGUUGUUGGGdUGdUCGACGCA 3', preferably the central stretch of nucleotides is

[SEQ ID NO: 78]
5' AUGdUGGUGGUGAAGGGUUGUUGGGdUGUCGACGCA 3'
or
[SEQ ID NO: 84]
5' AUGdUGGUGGUdGdAAGGGUUGUUGGGdUGdUCGACGCA 3'.

In a fifth embodiment of the first aspect which is also an embodiment of the second embodiment of the first aspect, the central stretch of nucleotides comprises a nucleotide sequence of

[SEQ ID NO: 66]
5' AUGn$_1$GGUGGUn$_2$n$_3$GGGGUUGUGGGGn$_4$Gn$_5$CGACGCA 3', wherein
 n$_1$ is U or dU, n$_2$ is G or dG, n$_3$ is A or dA, n$_4$ is U or dU, n$_5$ is U or dU and
 G, A, U and C are ribonucleotides, and
 dU, dG and dA are 2'-deoxyribonucleotides.

In a sixth embodiment of the first aspect which is also an embodiment of the second embodiment of the first aspect, the central stretch of nucleotides comprises a nucleotide sequence of

[SEQ ID NO: 67]
5' AUGn$_1$GGUGGUn$_2$n$_3$GGGGAUGUGGGGn$_4$Gn$_5$CGACGCA 3', wherein
 n$_1$ is U or dU, n$_2$ is G or dG, n$_3$ is A or dA, n$_4$ is U or dU, n$_5$ is U or dU and
 G, A, U and C are ribonucleotides, and
 dU, dG and dA are 2'-deoxyribonucleotides.

In a seventh embodiment of the first aspect which is also an embodiment of the second embodiment of the first aspect, the central stretch of nucleotides comprises a nucleotide sequence of

[SEQ ID NO: 64]
5' AUGn₁GGUGUUn₂n₃AGGGUUGUUGGGn₄Gn₅CGACGCA 3', wherein
$n_1$ is U or dU, $n_2$ is G or dG, $n_3$ is A or dA, $n_4$ is U or dU, $n_5$ is U or dU and
G, A, U and C are ribonucleotides, and
dU, dG and dA are 2'-deoxyribonucleotides.

In an eighth embodiment of the first aspect which is also an embodiment of the first, second, third, fourth, fifth, sixth and seventh embodiment of the first aspect, the central stretch of nucleotides consists of ribonucleotides and 2'-deoxyribonucleotides.

In a ninth embodiment of the first aspect which is also an embodiment of the first, second, third, fifth, sixth and seventh embodiment of the first aspect, the central stretch of nucleotides consists of ribonucleotides.

In a tenth embodiment of the first aspect which is also an embodiment of the the first, second, third, fourth, fifth, sixth, seventh, eighth and ninth embodiment of the first aspect, the nucleic acid molecule comprises in 5'→3' direction a first terminal stretch of nucleotides, the central stretch of nucleotides and a second terminal stretch of nucleotides, wherein
the first terminal stretch of nucleotides comprises one to five nucleotides, and
the second terminal stretch of nucleotides comprises one to five nucleotides,
preferably
the first terminal stretch of nucleotides comprises three to five nucleotides, and
the second terminal stretch of nucleotides comprises three to five nucleotides,
more preferably
the first terminal stretch of nucleotides comprises three nucleotides, and
the second terminal stretch of nucleotides comprises three nucleotides.

In an eleventh embodiment of the first aspect which is also an embodiment of the tenth embodiment of the first aspect, the first terminal stretch of nucleotides comprises a nucleotide sequence of 5' $Z_1Z_2Z_3Z_4$G 3' and the second terminal stretch of nucleotides comprises a nucleotide sequence of 5' $Z_5Z_6Z_7Z_5 Z_9$ 3',
wherein
$Z_1$ is G or absent, $Z_2$ is S or absent, $Z_3$ is S or absent, $Z_4$ is B or absent, $Z_5$ is C or dC, $Z_6$ is V or absent, $Z_7$ is S or absent, $Z_8$ is S or absent, $Z_9$ is C or absent, and
G, S, B, C, V are ribonucleotides, and
dC is a 2'-deoxyribonucleotide,
preferably
a) $Z_1$ is G, $Z_2$ is S, $Z_3$ is S, $Z_4$ is B, $Z_5$ is C or dC, $Z_6$ is V, $Z_7$ is S, $Z_8$ is S, $Z_9$ is C, or
b) $Z_1$ is absent, $Z_2$ is S, $Z_3$ is S, $Z_4$ is B, $Z_5$ is C or dC, $Z_6$ is V, $Z_7$ is S, $Z_8$ is S, $Z_9$ is absent, or
c) $Z_1$ is absent, $Z_2$ is absent, $Z_3$ is S, $Z_4$ is B, $Z_5$ is C or dC, $Z_6$ is V, $Z_7$ is S, $Z_8$ is absent, $Z_9$ is absent, or
d) $Z_1$ is absent, $Z_2$ is absent, $Z_3$ is absent, $Z_4$ is B, $Z_5$ is C or dC, $Z_6$ is V, $Z_7$ is absent, $Z_8$ is absent, $Z_9$ is absent, or
e) $Z_1$ is absent, $Z_2$ is S, $Z_3$ is S, $Z_4$ is B, $Z_5$ is C or dC, $Z_6$ is V, $Z_7$ is S, $Z_8$ is S, $Z_9$ is C, or
f) $Z_1$ is absent, $Z_2$ is absent, $Z_3$ is S, $Z_4$ is B, $Z_5$ is C or dC, $Z_6$ is V, $Z_7$ is S, $Z_8$ is S, $Z_9$ is C, or
g) $Z_1$ is absent, $Z_2$ is absent, $Z_3$ is absent, $Z_4$ is B, $Z_5$ is C or dC, $Z_6$ is V, $Z_7$ is S, $Z_8$ is S, $Z_9$ is C, or
h) $Z_1$ is absent, $Z_2$ is absent, $Z_3$ is absent, $Z_4$ is absent, $Z_5$ is C or dC, $Z_6$ is V, $Z_7$ is S, $Z_8$ is S, $Z_9$ is C, or
i) $Z_1$ is absent, $Z_2$ is absent, $Z_3$ is S, $Z_4$ is B, $Z_5$ is C or dC, $Z_6$ is V, $Z_7$ is S, $Z_8$ is S, $Z_9$ is absent, or
j) $Z_1$ is absent, $Z_2$ is absent, $Z_3$ is absent, $Z_4$ is B, $Z_5$ is C or dC, $Z_6$ is V, $Z_7$ is S, $Z_8$ is S, $Z_9$ is absent, or
k) $Z_1$ is absent, $Z_2$ is absent, $Z_3$ is absent, $Z_4$ is absent, $Z_5$ is C or dC, $Z_6$ is V, $Z_7$ is S, $Z_8$ is S, $Z_9$ is absent, or
l) $Z_1$ is absent, $Z_2$ is S, $Z_3$ is S, $Z_4$ is B, $Z_5$ is C or dC, $Z_6$ is V, $Z_7$ is S, $Z_8$ is absent, $Z_9$ is absent, or
m) $Z_1$ is absent, $Z_2$ is S, $Z_3$ is S, $Z_4$ is B, $Z_5$ is C or dC, $Z_6$ is V, $Z_7$ is absent, $Z_8$ is absent, $Z_9$ is absent, or
n) $Z_1$ is absent, $Z_2$ is absent, $Z_3$ is absent, $Z_4$ is absent, $Z_5$ is C, $Z_6$ is V, $Z_7$ is S, $Z_8$ is absent, $Z_9$ is absent, or
o) $Z_1$ is absent, $Z_2$ is absent, $Z_3$ is absent, $Z_4$ is B, $Z_5$ is C or dC, $Z_6$ is V, $Z_7$ is S, $Z_8$ is absent, $Z_9$ is absent, or
p) $Z_1$ is absent, $Z_2$ is absent, $Z_3$ is S, $Z_4$ is B, $Z_5$ is C or dC, $Z_6$ is V, $Z_7$ is absent, $Z_8$ is absent, $Z_9$ is absent, or
q) $Z_1$ is absent, $Z_2$ is absent, $Z_3$ is S, $Z_4$ is B, $Z_5$ is C or dC, $Z_6$ is absent, $Z_7$ is absent, $Z_8$ is absent, $Z_9$ is absent.

In a twelfth embodiment of the first aspect which is also an embodiment of the tenth and eleventh embodiment of the first aspect, the first terminal stretch of nucleotides comprises a nucleotide sequence of 5' GCCUG 3' and the second terminal stretch of nucleotides comprises a nucleotide sequence of 5' CAGGC 3' or of 5' dCAGGC 3', wherein C, A, G and U are ribonucleotides, and dC is a 2'-deoxyribonucleotide.

In a 13th embodiment of the first aspect which is also an embodiment of the twelfth embodiment of the first aspect, the second terminal stretch of nucleotides comprises a nucleotide sequence of 5' dCAGGC 3'.

In a 14th embodiment of the first aspect which is also an embodiment of the twelfth embodiment of the first aspect, the second terminal stretch of nucleotides comprises a nucleotide sequence of 5' CAGGC 3'.

In a 15th embodiment of the first aspect which is also an embodiment of the tenth and eleventh embodiment of the first aspect, the the first terminal stretch of nucleotides comprises a nucleotide sequence of 5' CCUG 3' or 5' CUG 3' or 5' UG 3' or 5' G 3', and the second terminal stretch of nucleotides comprises a nucleotide sequence of 5' dCAGGC 3', wherein C, A, G and U are ribonucleotides, and dC is a 2'-deoxyribonucleotide.

In a 16th embodiment of the first aspect which is also an embodiment of the 15th embodiment of the first aspect, the the first terminal stretch of nucleotides comprises a nucleotide sequence of 5' CCUG 3'.

In a 17th embodiment of the first aspect which is also an embodiment of the 15th embodiment of the first aspect, the the first terminal stretch of nucleotides comprises a nucleotide sequence of 5' CUG 3'.

In an 18th embodiment of the first aspect which is also an embodiment of the tenth and eleventh embodiment of the first aspect,
a) the first terminal stretch of nucleotides comprises a nucleotide sequence of 5' GCUG 3' and the second terminal stretch of nucleotides comprises a nucleotide sequence of 5' dCAGC 3'; or
b) the first terminal stretch of nucleotides comprises a nucleotide sequence of 5' GCCG 3' and the second terminal stretch of nucleotides comprises a nucleotide sequence of 5' dCGGC 3'; or c) the first terminal stretch of nucleotides comprises a nucleotide sequence of 5' GGCG 3' and the second terminal stretch of nucleotides comprises a nucleotide sequence of 5' dCGCC 3'; wherein C, A, G and U are ribonucleotides, and dC is a 2'-deoxyribonucleotide.

In a 19$^{th}$ embodiment of the first aspect which is also an embodiment of the 18$^{th}$ embodiment of the first aspect, first terminal stretch of nucleotides comprises a nucleotide sequence of 5' GGCG 3' and the second terminal stretch of nucleotides comprises a nucleotide sequence of 5' dCGCC 3'.

In a 20$^{th}$ embodiment of the first aspect which is also an embodiment of the tenth and eleventh embodiment of the first aspect, the the first terminal stretch of nucleotides comprises a nucleotide sequence of 5' CUG 3' or 5' UG 3' or 5' CG 3' or 5' G 3', and the second terminal stretch of nucleotides comprises a nucleotide sequence of 5' dCAGC 3', wherein C, A, G and U are ribonucleotides, and dC is a 2'-deoxyribonucleotide.

In a 21$^{st}$ embodiment of the first aspect which is also an embodiment of the tenth and eleventh embodiment of the first aspect, the first terminal stretch of nucleotides comprises a nucleotide sequence of 5' GCUG 3', and the second terminal stretch of nucleotides comprises a nucleotide sequence of 5' dCAC 3' or 5' dCC 3' or 5' dCA 3', wherein C, A, G and U are ribonucleotides, and dC is a 2'-deoxyribonucleotide.

In a 22$^{nd}$ embodiment of the first aspect which is also an embodiment of the tenth and eleventh embodiment of the first aspect, a) the first terminal stretch of nucleotides comprises a nucleotide sequence of 5' GUG 3' and the second terminal stretch of nucleotides comprises a nucleotide sequence of 5' dCAC 3'; or b) the first terminal stretch of nucleotides comprises a nucleotide sequence of 5' UG 3' and the second terminal stretch of nucleotides comprises a nucleotide sequence of 5' dCA 3'; or c) the first terminal stretch of nucleotides comprises a nucleotide sequence of 5' GCG 3' and the second terminal stretch of nucleotides comprises a nucleotide sequence of 5' dCGC 3'; or d) the first terminal stretch of nucleotides comprises a nucleotide sequence of 5' CG 3' and the second terminal stretch of nucleotides comprises a nucleotide sequence of 5' dCGC 3'; or e) the first terminal stretch of nucleotides comprises a nucleotide sequence of 5' G 3' and the second terminal stretch of nucleotides comprises a nucleotide sequence of 5' dCGC 3'; or f) the first terminal stretch of nucleotides comprises a nucleotide sequence of 5' GCG 3' and the second terminal stretch of nucleotides comprises a nucleotide sequence of 5' dCC 3'; or g) the first terminal stretch of nucleotides comprises a nucleotide sequence of 5' GCG 3' and the second terminal stretch of nucleotides comprises a nucleotide sequence of 5' dC 3'; or h) the first terminal stretch of nucleotides comprises a nucleotide sequence of 5' GG 3' and the second terminal stretch of nucleotides comprises a nucleotide sequence of 5' dCC 3';

i) the first terminal stretch of nucleotides comprises a nucleotide sequence of 5' GCG 3' and the second terminal stretch of nucleotides comprises a nucleotide sequence of 5' CGC 3'; wherein C, A, U and G are ribonucleotides, and dC is a 2'-deoxyribonucleotide.

In a 23$^{rd}$ embodiment of the first aspect which is also an embodiment of the 22$^{nd}$ embodiment of the first aspect, the first terminal stretch of nucleotides comprises a nucleotide sequence of 5' GCG 3' and the second terminal stretch of nucleotides comprises a nucleotide sequence of 5' dCGC 3'.

In a 24$^{th}$ embodiment of the first aspect which is also an embodiment of the first, second, third, fifth, sixth, seventh, ninth, tenth, eleventh, twelfth and 14$^{th}$ embodiment of the first aspect, the nucleic acid molecule comprises a nucleotide sequence selected from the group of SEQ ID NO: 3, SEQ ID NO: 4, SEQ ID NO: 5, SEQ ID NO: 6 and SEQ ID NO: 90, or a nucleic acid molecule having an identity of at least 85% to the nucleic acid molecule comprising a nucleotide sequence selected from the group of SEQ ID NO: 3, SEQ ID NO: 4, SEQ ID NO: 5, SEQ ID NO: 6 and SEQ ID NO: 90, or a nucleic acid molecule which is homologous to the the nucleic acid molecule comprising a nucleotide sequence selected from the group of SEQ ID NO: 3, SEQ ID NO: 4, SEQ ID NO: 5, SEQ ID NO: 6 and SEQ ID NO: 90, wherein the homology is at least 85%.

In a 25$^{th}$ embodiment of the first aspect which is also an embodiment of the first, second, third, fourth, eighth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$ and 23$^{rd}$ embodiment of the first aspect, the nucleic acid molecule comprises a nucleotide sequence selected from the group of SEQ ID NO: 14, SEQ ID NO: 21, SEQ ID NO: 24, SEQ ID NO: 25, SEQ ID NO: 26, SEQ ID NO: 27, SEQ ID NO: 37, SEQ ID NO: 57, SEQ ID NO: 59, SEQ ID NO: 60, SEQ ID NO: 91 and SEQ ID NO: 92, or a nucleic acid molecule having an identity of at least 85% to the nucleic acid molecule comprising a nucleotide sequence selected from the group of 14, SEQ ID NO: 21, SEQ ID NO: 24, SEQ ID NO: 25, SEQ ID NO: 26, SEQ ID NO: 27, SEQ ID NO: 37, SEQ ID NO: 57, SEQ ID NO: 59, SEQ ID NO: 60, SEQ ID NO: 91 and SEQ ID NO: 92, or a nucleic acid molecule which is homologous to the the nucleic acid molecule comprising a nucleotide sequence selected from the group of 14, SEQ ID NO: 21, SEQ ID NO: 24, SEQ ID NO: 25, SEQ ID NO: 26, SEQ ID NO: 27, SEQ ID NO: 37, SEQ ID NO: 57, SEQ ID NO: 59, SEQ ID NO: 60, SEQ ID NO: 91 and SEQ ID NO: 92, wherein the homology is at least 85%.

In a 26$^{th}$ embodiment of the first aspect which is also an embodiment of the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18th, 19$^{th}$, 20$^{th}$, 21$^{st}$, 22$^{nd}$, 23$^{rd}$, 24$^{th}$ and 25$^{th}$ embodiment of the first aspect, the nucleic acid molecule is capable of binding human C5a and mouse C5a.

In a 27$^{th}$ embodiment of the first aspect which is also an embodiment of the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$ and 26$^{th}$ embodiment of the first aspect, the nucleic acid molecule comprises at least one binding moiety which is capable of binding human C5a and mouse C5a, wherein such binding moiety consists of L-nucleotides.

In a 28$^{th}$ embodiment of the first aspect which is also an embodiment of the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26th and 27th embodiment of the first aspect, the nucleotides of or the nucleotides forming the nucleic acid molecule are L-nucleotides.

In a 29th embodiment of the first aspect which is also an embodiment of the first, second, third, fourth, fifth, sixth, seventh, eighth, ninth, tenth, eleventh, twelfth, 13th, 14th, 15th, 16th, 17th, 18th, 19th, 20th, 21st, 22nd, 23rd, 24th, 25th, 26th, 27th and 28th embodiment of the first aspect, the nucleic acid molecule is an L-nucleic acid molecule.

In a 30th embodiment of the first aspect which is also an embodiment of the first, second, third, fourth, fifth, sixth, seventh, eighth, ninth, tenth, eleventh, twelfth, 13th, 14th, 15th, 16th, 17th, 18th, 19th, 20th, 21st, 22nd, 23rd, 24th, 25th, 26th, 27th, 28th and 29th embodiment of the first aspect, the nucleic acid is an antagonist of an activity mediated by human and/or mouse C5a.

In a 31st embodiment of the first aspect which is also an embodiment of the first, second, third, fourth, fifth, sixth, seventh, eighth, ninth, tenth, eleventh, twelfth, 13th, 14th, 15th, 16th, 17th, 18th, 19th, 20th, 21st, 22nd, 23rd, 24th, 25th, 26th, 27th, 28th, 29th and 30th embodiment of the first aspect, the nucleic acid molecule comprises a modification group, wherein excretion rate of the nucleic acid molecule comprising the modification group from an organism is decreased compared to a nucleic acid not comprising the modification group.

In a 32nd embodiment of the first aspect which is also an embodiment of the first, second, third, fourth, fifth, sixth, seventh, eighth, ninth, tenth, eleventh, twelfth, 13th, 14th, 15th, 16th, 17th, 18th, 19th, 20th, 21st, 22nd, 23rd, 24th, 25th, 26th, 27th, 28th, 29th and 30th embodiment of the first aspect, the nucleic acid molecule comprises a modification group, wherein the nucleic acid molecule comprising the modification group has an increased retention time in an organism compared to a nucleic acid molecule not comprising the modification group.

In a 33rd embodiment of the first aspect which is also an embodiment of the 31st and 32nd embodiment of the first aspect, the modification group is selected from the group comprising biodegradable and non-biodegradable modifications, preferably the modification group is selected from the group comprising polyethylene glycol, linear polyethylene glycol, branched polyethylene glycol, hydroxyethyl starch, a peptide, a protein, a polysaccharide, a sterol, polyoxypropylene, polyoxyamidate and poly (2-hydroxyethyl)-L-glutamine.

In a 34th embodiment of the first aspect which is also an embodiment of the 33rd embodiment of the first aspect, the modification group is a polyethylene glycol, preferably consisting of a linear polyethylene glycol or branched polyethylene glycol, wherein the molecular weight of the polyethylene glycol is preferably from about 20,000 to about 120,000 Da, more preferably from about 30,000 to about 80,000 Da and most preferably about 40,000 Da.

In a 35th embodiment of the first aspect which is also an embodiment of the 33rd embodiment of the first aspect, the modification group is hydroxyethyl starch, wherein preferably the molecular weight of the hydroxyethyl starch is from about 50 to about 1000 kDa, more preferably from about 100 to about 700 kDa and most preferably from 200 to 500 kDa.

In a 36th embodiment of the first aspect which is also an embodiment of the 31st, 32nd, 33rd, 34th and 35th embodiment of the first aspect, the modification group is coupled to the nucleic acid molecule via a linker, whereby preferably the linker is a biodegradable linker.

In a 37th embodiment of the first aspect which is also an embodiment of the 31st, 32nd, 33rd, 34th, 35th and 36th embodiment of the first aspect, the modification group is coupled to the 5'-terminal nucleotide and/or the 3'-terminal nucleotide of the nucleic acid molecule and/or to a nucleotide of the nucleic acid molecule between the 5'-terminal nucleotide of the nucleic acid molecule and the 3'-terminal nucleotide of the nucleic acid molecule.

In a 38th embodiment of the first aspect which is also an embodiment of the 31st, 32nd, 33rd, 34th, 35th, 36th and 37th embodiment of the first aspect, the organism is an animal or a human body, preferably a human body.

The problem underlying the present invention is solved in a second aspect, which is also the first embodiment of the second aspect, by a nucleic acid molecule according to the first, second, third, fourth, fifth, sixth, seventh, eighth, ninth, tenth, eleventh, twelfth, 13th, 14th, 15th, 16th, 17th, 18th, 19th, 20th, 21st, 22nd, 23rd, 24th, 25th, 26th, 27th, 28th, 29th, 30th, 31st, 32nd, 33rd, 34th, 35th, 36th, 37th and 38th embodiment of the first aspect, for use in a method for the treatment and/or prevention of a disease.

In a second embodiment of the second aspect which is also an embodiment of the first embodiment of the second aspect, the disease is associated with complement activation and C5a-mediated pathogenic mechanisms, and/or is selected from the group comprising of autoimmune disease, inflammatory disease, systemic inflammatory response syndrome, disease of the eye, ischemia/reperfusion injuries, delayed graft function, transplant rejection, cardiovascular disease, respiratory disease, acute reactions, infectious disease, neurological disease, neurodegenerative disease, fibrotic disease, hematological disease, metabolic disease, tumors and clinical complications associated with complement activation by biomaterials, preferably the systemic inflammatory response syndrome is selected from the group comprising sepsis and secondary damages of trauma or severe burns.

The problem underlying the present invention is solved in a third aspect, which is also the first embodiment of the third aspect, by a pharmaceutical composition comprising a nucleic acid molecule according to the first, second, third, fourth, fifth, sixth, seventh, eighth, ninth, tenth, eleventh, twelfth, 13th, 14th, 15th, 16th, 17th, 18th, 19th, 20th, 21st, 22nd, 23rd, 24th, 25th, 26th, 27th, 28th, 29th, 30th, 31st, 32nd 33rd, 34th, 35th, 36th, 37th and 38th embodiment of the first aspect and according to the first embodiment of the second aspect, and optionally a further constituent, wherein the further constituent is selected from the group comprising a pharmaceutically acceptable excipient, a pharmaceutically acceptable carrier and a pharmaceutically active agent.

In a second embodiment of the third aspect which is also an embodiment of the first embodiment of the third aspect, the pharmaceutical composition comprises a nucleic acid molecule according to the first, second, third, fourth, fifth, sixth, seventh, eighth, ninth, tenth, eleventh, twelfth, 13th, 14th, 15th, 16th, 17th, 18th, 19th20th, 21st, 22nd, 23rd24th, 25th, 26th, 27th, 28th, 29th, 30th, 31st, 32nd, 33rd, 34th, 35th, 36th, 37th and 38th embodiment of the first aspect and according to the first embodiment of the second aspect, and a pharmaceutically acceptable carrier.

The problem underlying the present invention is solved in a fourth aspect, which is also the first embodiment of the fourth aspect, by the use of a nucleic acid molecule according to the first, second, third, fourth, fifth, sixth, seventh, eighth, ninth, tenth, eleventh, twelfth, 13th, 14th, 15th, 16th, 17th, 18th, 19th, 20th, 21st, 22nd, 23rd, 24th, 25th, 26th, 27th, 28t, 29th, 30th, 31st, 32nd, 33rd, 34th, 35th, 36th, 37th and 38th embodiment of the first aspect and according to the first embodiment of the second aspect, for the manufacture of a medicament.

In a second embodiment of the fourth aspect which is also an embodiment of the first embodiment of the fourth aspect, the medicament is for use in human medicine or for use in veterinary medicine.

In a third embodiment of the fourth aspect which is also an embodiment of the first and the second embodiment of the fourth aspect, the medicament is for the treatment and/or prevention of autoimmune disease, inflammatory disease, systemic inflammatory response syndrome, disease of the eye, ischemia/reperfusion injuries, delayed graft function, transplant rejection, cardiovascular disease, respiratory disease, acute reactions, infectious disease, neurological disease, neurodegenerative disease, fibrotic disease, hematological disease, metabolic disease, tumors and clinical complications associated with complement activation by biomaterials, preferably the systemic inflammatory response syndrome is selected from the group comprising sepsis and secondary damages of trauma or severe burns.

The problem underlying the present invention is solved in a fifth aspect, which is also the first embodiment of the fifth aspect, by the use of a nucleic acid molecule according to the first, second, third, fourth, fifth, sixth, seventh, eighth, ninth, tenth, eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$$31^{st}$, $32^{nd}$, $33^{rd}$, $34^{th}$, $35^{th}$, $36^{th}$, $37^{th}$ and $38^{th}$ embodiment of the first aspect and according to the first embodiment of the second aspect, for the manufacture of a diagnostic means.

The problem underlying the present invention is solved in a sixth aspect, which is also the first embodiment of the sixth aspect, by a complex comprising a nucleic acid molecule according to the first, second, third, fourth, fifth, sixth, seventh, eighth, ninth, tenth, eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$ and $38^{th}$ embodiment of the first aspect and according to the first embodiment of the second aspect, and C5a, wherein preferably the complex is a crystalline complex.

The problem underlying the present invention is solved in a seventh aspect, which is also the first embodiment of the seventh aspect, by the use of a nucleic acid molecule according to the first, second, third, fourth, fifth, sixth, seventh, eighth, ninth, tenth, eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$$28^{th}$, $29^{th}$, $30^{th}$, $31^{st}$, $32^{nd}$, $33^{rd}$, $34^{th}$, $35^{th}$, $36^{th}$, $37^{th}$ and $38^{th}$ embodiment of the first aspect and according to the first embodiment of the second aspect, for the detection of C5a.

The problem underlying the present invention is solved in an eighth aspect, which is also the first embodiment of the eighth aspect, by a method for the screening of an antagonist of an activity mediated by C5a comprising the following steps:
providing a candidate antagonist of the activity mediated by C5a,
providing a nucleic acid molecule according to the first, second, third, fourth, fifth, sixth, seventh, eighth, ninth, tenth, eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$ and $38^{th}$ embodiment of the first aspect and according to the first embodiment of the second aspect, providing a test system which provides a signal in the presence of an antagonist of the activity mediated by C5a, and determining whether the candidate antagonist of the activity mediated by C5a is an antagonist of the activity mediated by C5a.

The problem underlying the present invention is solved in a ninth aspect, which is also the first embodiment of the ninth aspect, by a kit for the detection of C5a, wherein the kit comprises a nucleic acid molecule according to the first, second, third, fourth, fifth, sixth, seventh, eighth, ninth, tenth, eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$ and $38^{th}$ embodiment of the first aspect and according to the first embodiment of the second aspect, and at least an instruction leaflet or a reaction vessel.

The problem underlying the present invention is solved in a tenth aspect, which is also the first embodiment of the tenth aspect, by a method for the detection of a nucleic acid according to the first, second, third, fourth, fifth, sixth, seventh, eighth, ninth, tenth, eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$ and $38^{th}$ embodiment of the first aspect and according to the first embodiment of the second aspect, in a sample, wherein the method comprises the steps of a) providing a capture probe, wherein the capture probe is at least partially complementary to a first part of the nucleic acid molecule according to the first, second, third, fourth, fifth, sixth, seventh, eighth, ninth, tenth, eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$ and $38^{th}$ embodiment of the first aspect and according to the first embodiment of the second aspect, and a detection probe, wherein the detection probe is at least partially complementary to a second part of the nucleic acid molecule according to the first, second, third, fourth, fifth, sixth, seventh, eighth, ninth, tenth, eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$ and $38^{th}$ embodiment of the first aspect and according to the first embodiment of the second aspect, or, alternatively, the capture probe is at least partially complementary to a second part of the nucleic acid molecule according to the first, second, third, fourth, fifth, sixth, seventh, eighth, ninth, tenth, eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$ $37^{th}$ and $38^{th}$ embodiment of the first aspect and according to the first embodiment of the second aspect, and the detection probe is at least partially complementary to a first part of the nucleic acid molecule according to the first, second, third, fourth, fifth, sixth, seventh, eighth, ninth, tenth, eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$ and $38^{th}$ embodiment of the first aspect and according to the first embodiment of the second aspect;

b) adding the capture probe and the detection probe separately or combined to a sample containing the nucleic acid molecule according to the first, second, third, fourth, fifth, sixth, seventh, eighth, ninth, tenth, eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, 30$^{th}$, 31$^{st}$, 32$^{nd}$, 33$^{rd}$, 34$^{th}$, 35$^{th}$, 36$^{th}$, 37$^{th}$ and 38$^{th}$ embodiment of the first aspect and according to the first embodiment of the second aspect, or presumed to contain the nucleic acid molecule according to the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$ 22$^{nd}$, 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{rd}$, 34$^{th}$, 35$^{th}$, 36$^{th}$, 37$^{th}$ and 38$^{th}$ embodiment of the first aspect and according to the first embodiment of the second aspect;

c) allowing the capture probe and the detection probe to react either simultaneously or in any order sequentially with the nucleic acid molecule according to the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{rd}$, 34$^{th}$, 35$^{th}$, 36$^{th}$, 37$^{th}$ and 38$^{th}$ embodiment of the first aspect and according to the first embodiment of the second aspect, or part thereof;

d) optionally detecting whether or not the capture probe is hybridized to the nucleic acid molecule according to the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{rd}$, 34$^{th}$, 35$^{th}$, 36$^{th}$, 37$^{th}$ and 38$^{th}$ embodiment of the first aspect and according to the first embodiment of the second aspect, provided in step a); and e) detecting the complex formed in step c) consisting of the nucleic acid molecule according to the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{rd}$, 34$^{th}$, 35$^{th}$, 36$^{th}$, 37$^{th}$ and 38$^{th}$ embodiment of the first aspect and according to the first embodiment of the second aspect, and the capture probe and the detection probe.

In a second embodiment of the tenth aspect which is also an embodiment of the first embodiment of the tenth aspect, the detection probe comprises a detection means, and/or wherein the capture probe is immobilized to a support, preferably a solid support.

In a third embodiment of the tenth aspect which is also an embodiment of the first and the second embodiment of the tenth aspect, any detection probe which is not part of the complex formed in step c) is removed from the reaction so that in step e) only a detection probe which is part of the complex, is detected.

In a fourth embodiment of the tenth aspect which is also an embodiment of the first, second and third embodiment of the tenth aspect, step e) comprises the step of comparing the signal generated by the detection means when the capture probe and the detection probe are hybridized in the presence of the nucleic acid molecule according to the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{th}$, 34$^{th}$, 35$^{th}$, 36$^{th}$, 37$^{th}$ and 38$^{th}$ embodiment of the first aspect and according to the first embodiment of the second aspect, or part thereof, and in the absence of said.

While not wishing to be bound by any theory, the present inventors have surprising found that the nucleic acid molecule according to the present invention binds specifically and with high affinity to both mouse C5a and human C5a, thereby inhibiting the binding of C5a to its C5a receptor, although the sequence homology of mouse C5a and human C5a is only 64% in the homologous region and mouse C5a having 3 additional N-terminal amino acids. Moreover, in contrast to human C5a, mouse C5a is not glycosylated. Asparagine$^{64}$, the glycosylation site in human C5a is mutated to glutamate in mouse. In particular the shown affinity of several individual C5a binding nucleic acids in the picomolar range could not be foreseen.

Furthermore, the instant inventors have surprisingly found that the nucleic acid molecule according to the present invention is suitable to block the interaction of C5a with the C5a receptor. Insofar, the nucleic acid molecule according to the present invention can also be viewed as an antagonist of the C5a receptor and, respectively, as an antagonist of the effects of C5a, in particular the effects of C5a on its receptor. An antagonist to C5a is a molecule that binds to C5a—such as the nucleic acid molecules according to the present invention—and inhibits the function of C5a, preferably in an in vitro assay or in an in vivo model as described in the Examples.

It is within the present invention that the nucleic acid according to the present invention is a nucleic acid molecule. Insofar the terms nucleic acid and nucleic acid molecule are used herein in a synonymous manner if not indicated to the contrary. Moreover, such nucleic acid(s) is/are preferably also referred to herein as the nucleic acid molecule(s) according to the (present) invention, the nucleic acid(s) according to the present invention, the inventive nucleic acid(s) or the inventive nucleic acid molecule(s).

The features of the nucleic acids according to the present invention as described herein can be realised in any aspect of the present invention where the nucleic acid is used, either alone or in any combination.

As to the various diseases, conditions and disorders which may be treated or prevented by using the nucleic acid molecule according to the present invention and compositions, preferably pharmaceutical compositions comprising the same, it has to be acknowledged that such diseases, conditions and disorders are those which are described herein, including and in particular those described and set forth in the introductory part of the instant application.

Insofar, the respective passages of the specification and the introductory part of the specification form an integral part of the present disclosure teaching the suitability of the nucleic acid molecule of the present invention for the prevention and treatment, respectively, for said diseases, conditions, and disorders. Additionally, a nucleic molecule according to the present invention is preferred if the physiological effect of the C5a-C5a receptor axis is related to higher plasma levels of C5a.

As used herein the term C5a refers to any C5a including, but not limited to, mammalian C5a. Preferably, the mammalian C5a is selected from the group comprising human, rat, mouse, monkey C5a (see C5a species alignment in FIG. 11). More preferably the C5a is human C5a. Human C5a is a basic protein having the amino acid sequence according to SEQ. ID. No. 50. Mouse C5a is a basic protein having the amino acid sequence according to SEQ. ID. No. 52.

As outlined in more detail in the claims and example 1, the present inventors could more surprisingly identify a number of different binding nucleic acid molecules capable of binding both human and mouse C5a.

As outlined in more detail herein, the present inventors have identified a number of different C5a binding nucleic acid molecules capable of binding both, human and mouse C5a, whereby the nucleic acid molecules can be characterised in terms of stretches of nucleotides which are also referred to herein as disclosed (see Example 1). As experimentally shown in examples 8 and 9 the inventors could surprisingly demonstrate in several systems that the nucleic acid molecule according to the present invention issuitbale for the treatment of sepsis.

Each of the different types of C5a binding nucleic acid molecules of the invention that bind to C5a comprises three different stretches of nucleotides: a first terminal stretch of nucleotides, a central stretch of nucleotides and a second terminal stretch of nucleotides. In general, C5a binding nucleic acid molecules of the present invention comprise at their 5'-end and the 3'-end each one of the terminal stretches of nucleotides, i.e. the first terminal stretch of nucleotides or the second terminal stretch of nucleotides (also referred to as 5'-terminal stretch of nucleotides and 3'-terminal stretch of nucleotides). The first terminal stretch of nucleotides and the second terminal stretch of nucleotides can, in principle due to their base complementarity, hybridize to each other, whereby upon hybridization a double-stranded structure is formed. However, such hybridization is not necessarily realized in the molecule under physiological and/or non-physiological conditions. The three stretches of nucleotides of C5a binding nucleic acid molecules—the first terminal stretch of nucleotides, the central stretch of nucleotides and second terminal stretch of nucleotides—are arranged to each other in 5'→3'-direction: the first terminal stretch of nucleotides—the central stretch of nucleotides—the second terminal stretch of nucleotides. Alternatively, the second terminal stretch of nucleotides, the central stretch of nucleotides and the terminal first stretch of nucleotides are arranged to each other in 5'→3'-direction.

The length of the central stretch of nucleotides of the nucleic acids according to the present invention is preferably 34.

The length of the first terminal stretch of nucleotides of the nucleic acids according to the present invention is between one and five nucleotides, preferably between three and five nucleotides, more preferably three nucleotides.

The length of the second terminal stretch of nucleotides of the nucleic according to the present invention is between one and five nucleotides, preferably between three and five nucleotides, more preferably three nucleotides.

The terms 'stretch' and 'stretch of nucleotides' are used herein in a synonymous manner if not indicated to the contrary.

The differences in the sequences of the defined stretches between the different C5a binding nucleic acid molecules may influence the binding affinity to C5a. Based on binding analysis of the different C5a binding nucleic acid molecules of the present invention the central stretch and the nucleotides forming the same are individually and more preferably in their entirety essential for binding of the C5a binding nucleic acid molecule to C5a.

In a preferred embodiment the nucleic acid molecule according to the present invention is a single nucleic acid molecule. In a further embodiment, the single nucleic acid molecule is present as a multitude of the single nucleic acid molecule or as a multitude of the single nucleic acid molecule species.

It will be acknowledged by the ones skilled in the art that the nucleic acid molecule in accordance with the invention preferably consists of nucleotides which are covalently linked to each other, preferably through phosphodiester links or linkages.

It is within the present invention that the nucleic acid molecule according to the present invention comprises two or more stretches or part(s) thereof that can, in principle, hybridise with each other. Upon such hybridisation a double-stranded structure is formed. It will be acknowledged by the ones skilled in the art that such hybridisation may or may not occur, particularly under in vitro and/or in vivo conditions. Also, in case of hybridisation, such hybridisation does not necessarily occur over the entire length of the two stretches where, at least based on the rules for base pairing, such hybridisation and thus formation of a double-stranded structure may, in principle, occur. As preferably used herein, a double-stranded structure is a part of a nucleic acid molecule or a structure formed by two or more separate strands or two spatially separated stretches of a single strand of a nucleic acid molecule, whereby at least one, preferably two or more base pairs exist which are base pairing preferably in accordance with the Watson-Crick base pairing rules. It will also be acknowledged by the one skilled in the art that other base pairing such as Hoogsten base pairing may exist in or may form such double-stranded structure. It is also to be acknowledged that the feature that two stretches hybridize preferably indicates that such hybridization is assumed to happen due to base complementarity of the two stretches regardless of whether such hybridization actually occurs in vivo and/or in vitro. In connection with the present invention such stretches are the first terminal stretch of nucleotides and the second stretch of nucleotides which, in an embodiment, may hybridize as defined above.

In a preferred embodiment the term arrangement as used herein, means the order or sequence of structural or functional features or elements described herein in connection with the nucleic acids molecule(s) disclosed herein.

It will be acknowledged by the person skilled in the art that the nucleic acids according to the present invention are capable of binding to both C5a and C5. This binding characteristic arises from the fact that for the identification of the nucleic acids a moiety of C5a was used which is present in both C5a and C5. Accordingly, the nucleic acids according to the present invention are suitable for the detection of either C5a or C5 or both. Also, it will be acknowledged by the person skilled in the art that the nucleic acid molecule according to the present invention is an antagonist to both C5 and C5a. Because of this the nucleic acids according to the present invention are suitable for the treatment and prevention, respectively, of any disease which is associated with or caused by either C5a or C5 or both. The scientific rational may be taken from the prior art which establishes that C5a and C5, respectively, are involved or associated with a variety of diseases and conditions, respectively, and which is incorporated herein by reference.

The C5a binding nucleic acid molecule of present invention disclosed herein have been shown to recognize C5a in the context of C5 (see Example 1). Therefore, it was investigated whether C5 cleavage to the anaphylatoxin C5a and C5b, which is part of the membrane attack complex (MAC) is inhibited by C5a binding nucleic acids. The MAC is the ultimate product of the complement cascade: a pore consisting of C5b-9. MAC is believed to insert into the cytoplasmic membranes of pathogens and kill them by induction of cytoplasmic leakage. The assay for C5 cleavage was achieved by using a complement-dependent sheep erythrocyte hemolysis test. The C5a binding molecule of the invention did not inhibit hemolysis (see Example 6). The C5a binding nucleic acid molecule of the invention does not interfere with C5 cleavage and MAC formation and are therefore selective antagonists of C5a only. If used as a medicament, this may be advantageous in many diseases, since the formation of the MAC that is beneficial in pathogen defense is not compromised in their presence.

The nucleic acid molecule according to the present invention shall also comprise nucleic acids which are essentially homologous to the particular sequences disclosed herein. The term substantially homologous shall be understood such as the homology is at least 75%, preferably 85%, more preferably 90% and most preferably more that 95%, 96%, 97%, 98% or 99%.

The actual percentage of homologous nucleotides present in the nucleic acid according to the present invention will depend on the total number of nucleotides present in the nucleic acid.

The percent modification can be based upon the total number of nucleotides present in the nucleic acid.

The homology between two nucleic acid molecules can be determined as known to the person skilled in the art. More specifically, a sequence comparison algorithm may be used for calculating the percent sequence homology for the test sequence(s) relative to the reference sequence, based on the designated program parameters. The test sequence is preferably the sequence or nucleic acid molecule which is said to be homologous or to be tested whether it is homologous, and if so, to what extent, to a different nucleic acid molecule, whereby such different nucleic acid molecule is also referred to as the reference sequence. In an embodiment, the reference sequence is a nucleic acid molecule as described herein, preferably a nucleic acid molecule having a sequence according to any one of SEQ ID NO: 3, SEQ ID NO: 4, SEQ ID NO: 5, SEQ ID NO: 6, SEQ ID NO: 90, SEQ ID NO: 14, SEQ ID NO: 21, SEQ ID NO: 24, SEQ ID NO: 25, SEQ ID NO: 26, SEQ ID NO: 27, SEQ ID NO: 37, SEQ ID NO: 57, SEQ ID NO: 59, SEQ ID NO: 60, SEQ ID NO: 91 and SEQ ID NO: 92. Optimal alignment of sequences for comparison can be conducted, e.g., by the local homology algorithm of Smith & Waterman (Smith & Waterman, 1981) by the homology alignment algorithm of Needleman & Wunsch (Needleman & Wunsch, 1970) by the search for similarity method of Pearson & Lipman (Pearson & Lipman, 1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

One example of an algorithm that is suitable for determining percent sequence identity is the algorithm used in the basic local alignment search tool (hereinafter "BLAST"), see, e.g. Altschul et al (Altschul et al. 1990 and Altschul et al, 1997). Software for performing BLAST analyses is publicly available through the National Center for Biotechnology Information (hereinafter "NCBI"). The default parameters used in determining sequence identity using the software available from NCBI, e.g., BLASTN (for nucleotide sequences) and BLASTP (for amino acid sequences) are described in McGinnis et al (McGinnis et al, 2004).

The nucleic acids according to the present invention shall also comprise nucleic acids which have a certain degree of identity relative to the nucleic acids disclosed herein and defined by their nucleotide sequence. More preferably, the instant invention also comprises those nucleic acid molecules which have an identity of at least 75%, preferably 85%, more preferably 90% and most preferably more than 95%, 96%, 97%, 98% or 99% relative to the nucleic acids disclosed herein and defined by their nucleotide sequence or a part thereof.

The term inventive nucleic acid or nucleic acid according to the present invention shall also comprise those nucleic acids comprising the nucleic acids sequences disclosed herein or part thereof, preferably to the extent that the nucleic acids or said parts are involved in the binding to human C5a. Such nucleic acid is, in an embodiment, one of the nucleic acid molecules described herein, or a derivative and/or a metabolite thereof, whereby such derivative and/or metabolite are preferably a truncated nucleic acid compared to the nucleic acid molecules described herein. Truncation may be related to either or both of the ends of the nucleic acids as disclosed herein. Also, truncation may be related to the inner sequence of nucleotides of the nucleic acid, i.e. it may be related to the nucleotide(s) between the 5' and the 3' terminal nucleotide, respectively. Moreover, truncation shall comprise the deletion of as little as a single nucleotide from the sequence of the nucleic acids disclosed herein. Truncation may also be related to more than one stretch of the inventive nucleic acid(s), whereby the stretch can be as little as one nucleotide long. The binding of a nucleic acid according to the present invention can be determined by the ones skilled in the art using routine experiments or by using or adopting a method as described herein, preferably as described herein in the example part.

The nucleic acid molecule according to the present invention may be either a D-nucleic acid molecule or an L-nucleic acid molecule. Preferably, the nucleic acid molecule according to the present invention is an L-nucleic acid molecule. More preferably, the nucleic acid molecule of the present invention is a Spiegelmer.

It is also within the present invention that, in an embodiment, each and any of the nucleic acid molecules described herein in their entirety in terms of their nucleic acid sequence(s) are limited to the particular indicated nucleotide sequence(s). In other words, the terms "comprising" or "comprise(s)" shall be interpreted in such embodiment in the meaning of containing or consisting of.

It is also within the present invention that the nucleic acids according to the present invention are part of a longer nucleic acid whereby this longer nucleic acid comprises several parts whereby at least one such part is a nucleic acid according to the present invention, or a part thereof. The other part(s) of these longer nucleic acids can be either one or several D-nucleic acid(s) or one or several L-nucleic acid(s). Any combination may be used in connection with the present invention. These other part(s) of the longer nucleic acid either alone or taken together, either in their entirety or in a particular combination, can exhibit a function which is different from binding, preferably from binding to C5a. One possible function is to allow interaction with other molecules, whereby such other molecules preferably are different from C5a, such as, e.g., for immobilization, cross-linking, detection or amplification. In a further embodiment of the present invention the nucleic acids according to the invention comprise, as individual or combined moieties, several of the nucleic acids of the present invention. Such nucleic acid comprising several of the nucleic acids of the present invention is also encompassed by the term longer nucleic acid.

An L-nucleic acid as used herein is a nucleic acid or nucleic acid molecule consisting of L-nucleotides, preferably consisting completely of L-nucleotides.

A D-nucleic acid as used herein is nucleic acid or nucleic acid molecule consisting of D-nucleotides, preferably consisting completely of D-nucleotides.

The terms nucleic acid and nucleic acid molecule are used herein in an interchangeable manner if not explicitly indicated to the contrary.

Also, if not indicated to the contrary, any nucleotide sequence is set forth herein in 5'→3' direction.

As preferably used herein any position of a nucleotide is determined or referred to relative to the 5' end of a sequence, a stretch or a substretch containing such nucleotide. Accordingly, a second nucleotide is the second nucleotide counted from the 5' end of the sequence, stretch and substretch, respectively. Also, in accordance therewith, a penultimate nucleotide is the second nucleotide counted from the 3' end of a sequence, stretch and substretch, respectively.

Irrespective of whether the nucleic acid molecule of the invention consists of D-nucleotides, L-nucleotides or a combination of both with the combination being e.g. a random combination or a defined sequence of stretches consisting of at least one L-nucleotide and at least one D-nucleic acid, the nucleic acid may consist of desoxyribonucleotide(s), ribonucleotide(s) or combinations thereof.

It is also within the present invention that the nucleic acid molecule consists of both ribonucleotides and 2'deoxyribonucleotides. The 2'deoxyribonucleotides and ribonucleotides are shown in FIGS. 22 and 23. In order to distinguish between ribonucleotides and 2'deoxyribonucleotides in the sequences of the nucleic acid molecules according to the present invention the following reference code is used herein.

The nucleic acid molecule according to the present invention consists of 2'deoxyribonucleotides, wherein
dG is 2'deoxy-guanosine-5'-monophosphate,
dC is 2'deoxy-cytidine-5'-monophosphate,
dA is 2'deoxy-adenosine-5'-monophosphate,
dU is 2'deoxy-uridine 5'monophosphate The nucleic acid molecule according to the present invention consists of ribonucleotides, wherein
G is guanosine-5'-monophosphate,
C is cytidine 5'-monophosphate,
A is adenosine-5'-monophosphate,
U is uridine-5'monophosphate.

For definition of ribonucleotide sequence motifs, the IUPAC abbreviations for ambiguous nucleotides are used:
S strong G or C;
W weak A or U;
R purine G or A;
Y pyrimidine C or U;
K keto G or U;
M imino A or C;
B not A C or U or G;
D not C A or G or U;
H not G A or C or U;
V not U A or C or G;
N all A or G or C or U Designing the nucleic acid molecule of the invention as an L-nucleic acid molecule is advantageous for several reasons. L-nucleic acid molecules are enantiomers of naturally occurring nucleic acids. D-nucleic acid molecules, however, are not very stable in aqueous solutions and particularly in biological systems or biological samples due to the widespread presence of nucleases. Naturally occurring nucleases, particularly nucleases from animal cells are not capable of degrading L-nucleic acids. Because of this, the biological half-life of an L-nucleic acid molecule is significantly increased in such a system, including the animal and human body. Due to the lacking degradability of L-nucleic acid molecules no nuclease degradation products are generated and thus no side effects arising therefrom observed in such a system including the animal and human body. This aspect distinguishes L-nucleic acid molecules from factually all other compounds which are used in the therapy of diseases and/or disorders involving the presence of C5. An L-nucleic acid molecule which specifically binds to a target molecule through a mechanism different from Watson Crick base pairing, or an aptamer which consists partially or completely of L-nucleotides, particularly with those parts of the aptamer being involved in the binding of the aptamer to the target molecule, is also called a spiegelmer. Aptamers and spiegelmers as such are known to a person skilled in the art and are, among others, described in 'The Aptamer Handbook' (eds. Klussmann, 2006).

It is also within the present invention that the nucleic acid molecule of the invention, regardless whether it is are present as a D-nucleic acid, L-nucleic acid or D,L-nucleic acid or whether it is DNA or RNA, may be present as single stranded or double stranded nucleic acid molecule. Typically, the nucleic acid molecule is a single stranded nucleic acid molecule which exhibits a defined secondary structure due to its primary sequence and may thus also form a tertiary structure. The nucleic acid molecule, however, may also be double stranded in the meaning that two strands which are complementary or partially complementary to each other are hybridised to each other.

The nucleic acid molecule of the invention may be modified. Such modification may be related to the single nucleotide of the nucleic acid molecule and is well known in the art. Examples for such modification are described by, among others, Venkatesan et al. (Venkatesan et al., 2003) and Kusser (Kusser, 2000). Such modification can be a H atom, a F atom or O—$CH_3$ group or $NH_2$-group at the 2' position of one, several of all of the individual nucleotides of which the nucleic acid molecule consists. Also, the nucleic acid molecule according to the present invention can comprise at least one LNA nucleotide. In an embodiment the nucleic acid molecule according to the present invention consists of LNA nucleotides.

In an embodiment, the nucleic acid molecule according to the present invention may be a multipartite nucleic acid molecule. A multipartite nucleic acid molecule as used herein is a nucleic acid molecule which consists of at least two separate nucleic acid strands. These at least two nucleic acid strands form a functional unit whereby the functional unit is a ligand to a target molecule and, preferably an antagonist to the target molecule, in the instant case of C5a. The at least two nucleic acid strands may be derived from any of the nucleic acid molecule of the invention by either cleaving a nucleic acid molecule of the invention to generate at least two strands or by synthesising one nucleic acid molecule corresponding to a first part of the full-length nucleic acid molecule of the invention and another nucleic acid molecule corresponding to another part of the full-length nucleic acid molecule of the invention. Depending on the number of parts forming the full-length nucleic acid molecules the corresponding number of parts having the required nucleotide sequence will be synthesized It is to be acknowledged that both the cleavage approach and the synthesis approach may be applied to generate a multipartite nucleic acid molecule where there are more than two strands as exemplified above. In other words, the at least two separate nucleic acid strands are typically different from two strands being complementary and hybridising to each other although a certain extent of complementarity between said at least two separate nucleic acid strands may exist and whereby such complementarity may result in the hybridisation of said separate strands.

Finally, it is also within the present invention that a fully closed, i.e. circular structure for the nucleic acid molecule according to the present invention is realized, i.e. that the nucleic acid molecule according to the present invention are closed in an embodiment, preferably through a covalent linkage, whereby more preferably such covalent linkage is made between the 5' end and the 3' end of the nucleic acid sequence of the nucleic acid molecule of the invention as disclosed herein or any derivative thereof.

A possibility to determine the binding constants of the nucleic acid molecules according to the present invention is the use of the methods as described in example 3 and 4 which confirms the above finding that the nucleic acids according to the present invention exhibit a favourable $K_D$ value range. An appropriate measure in order to express the intensity of the binding between the individual nucleic acid molecule and the target which is in the present case C5a is the so-called $K_D$ value which as such as well the method for its determination are known to the one skilled in the art.

Preferably, the $K_D$ value shown by the nucleic acids according to the present invention is below 1 µM. A $K_D$ value of about 1 µM is said to be characteristic for a non-specific binding of a nucleic acid to a target. As will be acknowledged by the ones skilled in the art, the $K_D$ value of a group of compounds such as the nucleic acids according to the present invention is within a certain range. The above-mentioned $K_D$ of about 1 µM is a preferred upper limit for the $K_D$ value. The lower limit for the $K_D$ of target binding nucleic acids can be as little as about 10 picomolar or can be higher. It is within the present invention that the $K_D$ values of individual nucleic acids binding to C5a is preferably within this range. Preferred ranges can be defined by choosing any first number within this range and any second number within this range. Preferred upper $K_D$ values are 250 nM and 100 nM, preferred lower $K_D$ values are 50 nM, 10 nM, 1 nM, 100 pM and 10 pM. The more preferred upper $K_D$ value is 10 nM, the more preferred lower $K_D$ value is 100 pM.

In addition to the binding properties of the nucleic acid molecules according to the present invention, the nucleic acid molecules according to the present invention inhibit the function of the respective target molecule which is in the present case C5a. The inhibition of the function of C5a—for instance the stimulation of the respective receptors as described previously—is achieved by binding of nucleic acid molecules according to the present invention to C5a and forming a complex of a nucleic acid molecule according to the present invention and C5a. Such complex of a nucleic acid molecule and C5a cannot stimulate the receptors that normally are stimulated by C5a, i.e. C5a which is not present in a complex with a nucleic acid molecule of the invention. Accordingly, the inhibition of receptor function by nucleic acid molecules according to the present invention is independent from the respective receptor that can be stimulated by C5a but results from preventing the stimulation of the receptor by C5a by the nucleic acid molecules according to the present invention.

A possibility to determine the inhibitory constant of the nucleic acid molecules according to the present invention is the use of the methods as described in example 5 which confirms the above finding that the nucleic acids according to the present invention exhibit a favourable inhibitory constant which allows the use of said nucleic acids in a therapeutic treatment scheme. An appropriate measure in order to express the intensity of the inhibitory effect of the individual nucleic acid molecule on interaction of the target which is in the present case C5a and the respective receptor, is the so-called half maximal inhibitory concentration (abbr. $IC_{50}$) which as such as well the method for its determination are known to the one skilled in the art.

Preferably, the $IC_{50}$ value shown by the nucleic acid molecules according to the present invention is below 1 µM. An $IC_{50}$ value of about 1 µM is said to be characteristic for a non-specific inhibition of target functions by a nucleic acid molecule. As will be acknowledged by the ones skilled in the art, the $IC_{50}$ value of a group of compounds such as the nucleic acid molecules according to the present invention is within a certain range. The above-mentioned $IC_{50}$ of about 1 µM is a preferred upper limit for the $IC_{50}$ value. The lower limit for the $IC_{50}$ of target binding nucleic acid molecules can be as little as about 10 picomolar or can be higher. It is within the present invention that the $IC_{50}$ values of individual nucleic acids binding to C5a is preferably within this range. Preferred ranges can be defined by choosing any first number within this range and any second number within this range. Preferred upper $IC_{50}$ values are 250 nM and 100 nM, preferred lower $IC_{50}$ values are 50 nM, 10 nM, 1 nM, 100 pM and 10 pM. The more preferred upper $IC_{50}$ value is 5 nM, the more preferred lower $IC_{50}$ value is 100 pM.

The nucleic acid molecules according to the present invention may have any length provided that they are still able to bind to the target molecule. It will be acknowledged in the art that there are preferred lengths of the nucleic acids according to the present inventions. Typically, the length is between 15 and 120 nucleotides. It will be acknowledged by the ones skilled in the art that any integer between 15 and 120 is a possible length for the nucleic acids according to the present invention. More preferred ranges for the length of the nucleic acids according to the present invention are lengths of about 20 to 100 nucleotides, about 20 to 80 nucleotides, about 20 to 60 nucleotides, about 38 to 44 nucleotides and about 40 nucleotides.

It is within the present invention that the nucleic acid molecule of the present invention comprises a moiety which preferably is a high molecular weight moiety and/or which preferably allows to modify the characteristics of the nucleic acid molecule in terms of, among others, residence time in the animal body, preferably the human body. A particularly preferred embodiment of such modification is PEGylation and HESylation of the nucleic acids according to the present invention. As used herein PEG stands for poly(ethylene glycole) and HES for hydroxyethly starch. PEGylation as preferably used herein is the modification of a nucleic acid molecule according to the present invention whereby such modification consists of a PEG moiety which is attached to a nucleic acid molecule according to the present invention.

HESylation as preferably used herein is the modification of a nucleic acid molecule according to the present invention whereby such modification consists of a HES moiety which is attached to a nucleic acid molecule according to the present invention. These modifications as well as the process of modifying a nucleic acid molecule using such modifications, is described in European patent application EP 1 306 382, the disclosure of which is herewith incorporated in its entirety by reference.

In the case of PEG being such high molecular weight moiety the molecular weight is preferably about 20,000 to about 120,000 Da, more preferably from about 30,000 to about 80,000 Da and most preferably about 40,000 Da. In the case of HES being such high molecular weight moiety the molecular weight is preferably from about 50 kDa to about 1000 kDa, more preferably from about 100 kDa to about 700 kDa and most preferably from 200 kDa to 500 kDa. HES exhibits a molar substitution of 0.1 to 1.5, more preferably of 1 to 1.5 and exhibits a substitution grade expressed as the C2/C6 ratio of approximately 0.1 to 15, preferably of approximately 3 to 10. The process of HES modification is, e.g., described in German patent application DE 1 2004 006 249.8 the disclosure of which is herewith incorporated in its entirety by reference.

The modification can, in principle, be made to the nucleic acid molecule of the present invention at any position thereof. Preferably such modification is made either to the 5'-terminal nucleotide, the 3'-terminal nucleotide and/or any nucleotide between the 5' nucleotide and the 3' nucleotide of the nucleic acid molecule.

The modification and preferably the PEG and/or HES moiety can be attached to the nucleic acid molecule of the present invention either directly or indirectly, preferably indirectly through a linker. It is also within the present invention that the nucleic acid molecule according to the present invention comprises one or more modifications, preferably one or more PEG and/or HES moiety. In an embodiment the individual linker molecule attaches more than one PEG moiety or HES moiety to a nucleic acid molecule according to the present invention. The linker used in connection with the present invention can itself be either linear or branched. This kind of linkers are known to the ones skilled in the art and are further described in international patent applications WO2005/074993 and WO2003/035665.

In a preferred embodiment the linker is a biodegradable linker. The biodegradable linker allows to modify the characteristics of the nucleic acid molecule according to the present invention in terms of, among other, residence time in an animal body, preferably in a human body, due to release of the modification from the nucleic acid molecule according to the present invention.

Usage of a biodegradable linker may allow a better control of the residence time of the nucleic acid molecule according to the present invention. A preferred embodiment of such biodegradable linker is a biodegradable linker as described in, but not limited to, international patent applications WO2006/052790, WO2008/034122, WO2004/092191 and WO2005/099768.

It is within the present invention that the modification or modification group is a biodegradable modification, whereby the biodegradable modification can be attached to the nucleic acid molecule of the present invention either directly or indirectly, preferably through a linker. The biodegradable modification allows modifying the characteristics of the nucleic acid molecule according to the present invention in terms of, among other, residence time in an animal body, preferably in a human body, due to release or degradation of the modification from the nucleic acid molecule according to the present invention. Usage of a biodegradable modification may allow a better control of the residence time of the nucleic acid molecule according to the present invention. A preferred embodiment of such biodegradable modification is biodegradable as described in, but not restricted to, international patent applications WO2002/065963, WO2003/070823, WO2004/113394 and WO2000/41647, preferably in WO2000/41647, page 18, line 4 to 24.

Beside the modifications as described above, other modifications can be used to modify the characteristics of the nucleic acid molecule according to the present invention, whereby such other modifications may be selected from the group of proteins, lipids such as cholesterol and sugar chains such as amylase, dextran etc.

Without wishing to be bound by any theory, by modifying the nucleic acid molecule according to the present invention with a high molecular weight moiety such as a polymer and more particularly one or several of the polymers disclosed herein, which are preferably physiologically acceptable, the excretion kinetic of the thus modified nucleic acid molecule of the invention from an animal or human body to which the modified nucleic acid molecule of the invention is administered is changed is changed. More particularly, due to the increased molecular weight of the tus modified nucleic acid molecule of the invention and due to the nucleic acid molecule of the invention not being subject to metabolism particularly when in the L form, i.e. being an L-nucleic acid molecule, excretion from an animal body, preferably from a mammalian body and more preferably from a human body is decreased. As excretion typically occurs via the kidneys, the present inventors assume that the glomerular filtration rate of the thus modified nucleic acid molecule is significantly reduced compared to a nucleic acid molecule not having this kind of high molecular weight modification which results in an increase in the residence time of the modified nucleic acid molecule in the animal body. In connection therewith it is particularly noteworthy that, despite such high molecular weight modification the specificity of the nucleic acid molecule according to the present invention is not affected in a detrimental manner. Insofar, the nucleic acid molecule according to the present invention has among others, the surprising characteristic—which normally cannot be expected from a pharmaceutically active compound—that a pharmaceutical formulation providing for a sustained release is not necessarily required for providing a sustained release of the nucleic acid molecule according to the present invention. Rather, the nucleic acid molecule according to the present invention in its modified form comprising a high molecular weight moiety, can as such already be used as a sustained release-formulation as it acts, due to its modification, already as if it was released from a sustained-release formulation. Insofar, the modification(s) of the nucleic acid molecule according to the present invention as disclosed herein and the thus modified nucleic acid molecule according to the present invention and any composition comprising the same may provide for a distinct, preferably controlled pharmacokinetics and biodistribution thereof. This also includes residence time in the circulation of the animal and human body and distribution to tissues in such animal and human. Such modifications are further described in the patent application WO2003/035665.

However, it is also within the present invention that the nucleic acid molecule according to the present invention does not comprise any modification and particularly no high molecular weight modification such as PEG or HES. Such embodiment is particularly preferred when the nucleic acid molecule according to the present invention shows preferential distribution to any target organ or tissue in the body or when a fast clearance of the nucleic acid molecule according to the present invention from the body after administration is desired. A nucleic acid molecule according to the present invention as disclosed herein with a preferential distribution profile to any target organ or tissue in the body would allow establishment of effective local concentrations in the target tissue while keeping systemic concentration of the nucleic acid molecule low. This would allow the use of low doses which is not only beneficial from an economic point of view, but also reduces unnecessary exposure of other tissues to the nucleic acid molecule, thus reducing the potential risk of side effects. Fast clearance of the nucleic acid molecule according to the present invention from the body after administration might be desired, among others, in case of in vivo imaging or specific therapeutic dosing requirements using the nucleic acid molecule according to the present invention or medicaments comprising the same.

The inventive nucleic acids, which are also referred to herein as the nucleic acids according to the present invention, and/or the antagonists according to the present invention may be used for the generation or manufacture of a medicament. Such medicament or a pharmaceutical composition according to the present invention contains at least one of the inventive nucleic acids, optionally together with further pharmaceutically active compounds, whereby the inventive nucleic acid preferably acts as pharmaceutically active compound itself. Such medicaments comprise in preferred embodiments at least a pharmaceutically acceptable carrier.

Such carrier may be, e.g., water, buffer, PBS, glucose solution, preferably a 5% glucose salt balanced solution, starch, sugar, gelatine or any other acceptable carrier substance. Such carriers are generally known to the one skilled in the art. It will be acknowledged by the person skilled in the art that any embodiments, use and aspects of or related to the medicament of the present invention is also applicable to the pharmaceutical composition of the present invention and vice versa.

The indication, diseases and disorders for the treatment and/or prevention of which the nucleic acids, the pharmaceutical compositions and medicaments in accordance with or prepared in accordance with the present invention result from the involvement, either direct or indirect, of C5a in the respective pathogenetic mechanism.

The local release of C5a at sites of inflammation results in powerful pro-inflammatory stimuli. Thus, neutralization of C5a might be beneficial in many acute or chronic conditions, such as immune complex associated diseases in general (Heller et al., 1999); neurodegeneration and inflammation, e.g. in Alzheimer's disease (Bonifati & Kishore, 2007), where the complement C5a receptor antagonist PMX205 improved behavioral parameters and a reduction of pathological markers such as fibrillar deposits and activated glia (Fonseca et al. 2009). Other inflammatory diseases with C5a involvement are systemic lupus erythematosus (Jacob et al. 2010a; Jacob et al. 2010b), asthma (Kohl, 2001); secondary damages of trauma (Yao et al. 1998); septic shock (Huber-Lang et al., 2001); systemic inflammatory response syndrome (SIRS); multiorgan failure (MOF); acute respiratory distress syndrome (ARDS); inflammatory bowel syndrome (IBD) (Woodruff et al., 2003); immune-complex-mediated renal disease (Wang, 2006), e.g. as a complication of systemic lupus erythematosus (Manderson et al, 2004); infections and their consequences (e.g. vascular leakage or bone loss such as bone loss secondary to periodontitis (Breivik et al. 2011)); severe burns (Piccolo et al., 1999); reperfusion injury of organs such as heart, spleen, bladder, pancreas, stomach, lung, liver, kidney, limbs, brain, sceletal muscle or intestine (Riley et al., 2000)(Gueler et al. 2008; Khan et al. 2011; van der Pals et al. 2010; Zheng et al. 2008) that may lead amongst others to delayed graft function (Lewis et al, 2008) or fibrosis and/or remodelling of the organ, e.g. after an infarction of heart, brain or lung leading to secondary damage; psoriasis (Bergh et al., 1993); myocarditis; multiple sclerosis (Muller-Ladner et al., 1996); paroxysmal nocturnal hemoglobinuria (PNH), hemolysis, thromboembolism (Hillmern et al. 2007) and rheumatoid arthritis (RA) (Woodruff et al., 2002), resection of renal cell carcinoma and activation of osteoclasts promoting bone destruction, e.g. resulting in osteoarthtitis or delayed healing. Complement C5a has also been found in elevated amounts in drusen in age-related macular degeneration and it has been shown to lead to increased VEGF-expression and to promote choroidal neovascularization that may lead to vision impairment and loss (Nozaki et al, 2006).

Activation of the complement system has also been shown to raise susceptibility to develop cerebral malaria in a mouse model. C5a or C5a receptor blockade using serum from mice immunized with theses molecules conferred resistance to cerebral malaria. Therefore, blocking the C5 C5a axis may be beneficial in the prevention of developing malaria, especially cerebral malaria in humans (Patel et al. 2008).

Autoimmune inflammatory diseases with complement involvement have been reviewed recently (Chen et al. 2010). An expert review on possible and already pursued complement-targeted therapies appeared in Nature Biotechnology (Ricklin & Lambris, 2007). An update was published in Molecular Medicine in 2011 (Ehrnthaller et al. 2011).

Of course, because the C5a binding nucleic acids according to the present invention interact with or bind to human C5a, a skilled person will generally understand that the C5a binding nucleic acids according to the present invention can easily be used for the treatment, prevention and/or diagnosis of any disease of humans and animals as described herein. In connection therewith, it is to be acknowledged that the nucleic acid molecules according to the present invention can be used for the treatment and prevention of any of the diseases, disorder or condition described herein, irrespective of the mode of action underlying such disease, disorder and condition.

In the following, and without wishing to be bound by any theory, the rational for the use of the nucleic acid molecules according to the present invention in connection with the various diseases, disorders and conditions is provided, thus rendering the claimed therapeutic, preventive and diagnostic applicability of the nucleic acid molecules according to the present invention plausible. In order to avoid any unnecessary repetition, it should be acknowledged that due to the involvement of the C5a-C5a receptor axis as outlined in connection therewith said axis may be addressed by the nucleic acid molecules according to the present invention such that the claimed therapeutic, preventive and diagnostic effect is achieved. It should furthermore be acknowledged that the particularities of the diseases, disorders and conditions, of the patients and any detail of the treatment regimen described in connection therewith, may be subject to preferred embodiments of the instant application.

Myeloid-derived suppressor (abbr. MDS) cells were originally observed in cancer patient >30 years ago, their role as spoilers of anti-tumor immunity is only now being appreciated. A heterogeneous population of normal myeloid cells trapped in intermediate stages of differentiation, MDS cells accumulate in the blood, lymph nodes and at tumor sites in virtually all cancer patients. In healthy individuals, these cells differentiate into macrophages, dendritic cells and neutrophils, but the tumors secrete a range of factors that disrupt diffentiation of immune progenitor cells (Ostrand-Rosenberg, 2008). As shown for isolated MSD cells from the peripheral blood and the spleens of healthy mice, the MDS cells express the C5a receptor on their surface to a similar extent—an abundant expression—to that of their mature counterparts granulocytes and monocytes. As well in tumor bearing mice, the MDS cells express the C5a receptor, but the expression level is lower on the surface of tumor associated MSD cells than on MSD cells in the peripheral blood and spleen. The reason is that the C5a receptor is internatilzed in tumor associated cells as shown by Markiewski et al, a C5a receptor antagonist can block the function of the C5a receptor on the surface of the MSD cells and led to an impaired tumor growth (Markiewski et al. 2008). C5a also acts as a suppressor of natural killer cell (NK cell) functions providing an explanation for negative impact of complement on tumor surveillance and NK function disorders in patients with certain immune diseases (Li et al. 2012; Min et al. 2012).

Accordingly, disease and/or disorders and/or diseased conditions for the treatment and/or prevention of which the medicament according to the present invention may be used include, but are not limited to tumor associated diseases and/or disorders and/or diseased conditions.

In a preferred embodiment, tumor or tumour is the name for a swelling or lesion formed by an abnormal growth of cells (termed neoplastic). A tumor can be benign, pre-malignant or malignant tumor. Moreover a tumor can be a solid tumor, preferably carcininoma, sarcomaa, aoteoma, fibrosarcoma, and chondrosoma The tumors which can in particular be treated by a medicament or a nucleic acid molecule according to the present invention are preferably those tumors which are selected from the group comprising tumors of the endocrine system, the eye, the gastrointestinal tract, the genital system, the haematopoietic system (including mixed and embryonic tumours), the mammary gland, the nervous system, the respiratory system, the skeleton, the skin, the soft tissues, the urinary outflow system Preferably, these tumors are selected from the group comprising breast cancer, ovary carcinoma, prostate carcinoma, osteosarcoma, glioblastoma, melanoma, small-cell lung carcinoma and colorectal carcinoma.

It is within the present invention that the medicament and pharmaceutical composition, respectively, containing a nucleic acid according to the present inventors may be used for the treatment in such way.

In a further embodiment, the medicament comprises a further pharmaceutically active agent for the treatment of tumors. Such further pharmaceutically active compounds are, among others but not limited thereto, those known to antineoplastic-active substances as alkylating agents, antimetabolites, antiangiogenic agents, mitose inhibiting agents, topoisomerase inhibitors, inhibitors of the cellular signal transduction, hormones, antibodies, immune conjugates and fusion proteins.

Other pharmaceutically active compounds are, among others but not limited thereto, those known to Bleomycin, inhibitors of thymidylatsynthase such as Raltitrexed and Pemetrexed, enzymes such as L-asparaginase, Miltefosin and ANAgrelid, inhibitors of the proteasome such as Bortezomib.

Moreover, the medicament according to the present invention may be used for the treatment and/or prevention of chronic obstructive pulmonary disease.

Chronic obstructive pulmonary disease (abbr. COPD) is a lung ailment that is characterized by a persistent blockage of airflow from the lungs. It is an under-diagnosed, life-threatening lung disease that interferes with normal breathing and is not fully reversible. COPD includes a few lung diseases: the most common are chronic bronchitis and emphysema. Many people with COPD have both of these diseases. The emphysema is a damage to the air sacs at the tips of the airways what makes it hard for the body to take in the oxygen it needs. During chronic bronchitis the airways are irritated, red, and make too much sticky mucus. The walls of the airways are swollen and partly block the air from passing through.

Neutrophils are attracted towards a C5a gradient, release superoxide radicals to kill pathogens and release beta-glucuronidase to hydrolyse complex glucuronide conjugates at the site of inflammation. However, these valuable defense mechanisms can be damaging to the body if the neutrophils are recruited to sites of pathogen-free inflammation, e.g. at reperfused sites after infaction, stroke or organ transplantation or in cases of autoimmune disease, alzheimer's disease and others that are listed below.

In turn, excessively high C5a concentrations—especially if they are not only locally elevated as they appear during sepsis—lead to a systemic activation of the neutrophils (leading to organ damage) with subsequent exhaustion and deactivation by means of reduced C5a receptor expression on the neutrophils' cell surface. This renders the patient even more vulnerable to the pathogens that persist in his body (Huber-Lang et al. 2002).

A C5a-binding nucleic acid that is also inhibitory for the C5a-mediated effects on its receptor (CD88) (as shown by chemotaxis assays using differentiated BAF-3 cells) has therefore the potential to block the above named consequences of C5a signaling and could prove beneficial as part of a medicament in a number of diseases and conditions which aberrant C5a signaling is implicated in. One of these conditions is polymicrobial sepsis. There is a rich body of literature collecting evidence for the detrimental role of C5a signaling in sepsis (Ward 2010b).

Nucleic acids according to the present inventions were found to improve survival of mice and organ function parameters in cecal ligation and puncture (CLP) studies. CLP is a well-established rodent model for polymicrobial sepsis. Recently the role of complement C5 in sepsis induced by cecal ligation and puncture was investigated in wild-type and C5-deficient mice (Flierl et al. 2008). C5−/− mice had no survival advantage compared to WT mice and displayed a 400-fold increase of blood-borne bacteria when compared to wild-type mice. These effects were linked to the inability of C5 (−/−) mice to assemble the terminal membrane attack complex (MAC). The authors conclude that, during sepsis, selective blockade of C5a or its receptor (rather than C5) seems a more promising strategy, because C5a-blockade still allows for MAC formation while the adverse effects of C5a are prevented. In agreement, genetic deletion of C5a receptors CD88 and C5L2, pharmacological blockade of CD88 or pharmacological neutralization of C5a has been shown to be protective in cecal ligation and puncture (CLP)—induced sepsis (Czermak et al. 1999; Rittirsch et al. 2008). A translational in vitro model of meningococcal sepsis using human whole blood confirms that selective C5a inhibition (in contrast to blockade of C5 cleavage) prevents potentially harmful leukocyte activation without comprising bacterial clearance (Sprong et al. 2003). Inhibition of C5a prevents multiorgan failure in experimental sepsis by limiting systemic inflammation, coagulation and other pathogenic mechanisms (Huber-Lang et al. 2001; Huber-Lang et al. 2002; Laudes et al. 2002; Rittirsch et al. 2008; Ward 2010a). The nucleic acids according to this invention, though binding to C5 do not block C5 cleavage to C5a and C5b which is required for MAC formation.

On the contrary, the inventive nucleic acids occupy the protein C5, which also increases terminal plasma half-life and selectively block the action of C5a once this has been liberated, e.g. by the C5 convertase. In a sepsis model, nucleic acids according to this invention have been shown to limit inflammation, prevent multi organ failure and edema formation and to improve survival. Sepsis patients often require mechanical ventilation due to acute lung injury (ALI) and acute respiratory distress syndrome (ARDS). ALI/ARDS may also develop from a direct infection of the lung by community- or hospital-acquired infections in pneumonia. There is abundant evidence for a pathogenic role of C5a in ALI/ARDS. C5a induced tissue factor expression contributes to fibrin deposition within pulmonary alveoli of ALI/ARDS patients (Kambas et al. 2008). Experimental ALI is attenuated in C5−/− mice and C5a-neutralisation or silencing of C5aR in the lungs suppresses the inflammatory response and prevents vascular leakage (Bosmann & Ward 2012).

Moreover, other disease and/or disorders and/or diseased conditions for the treatment and/or prevention of which the medicament according to the present invention may be used include, but are not limited to are autoimmune diseases such as rheumatoid arthritis (abbr. RA), ankylosing spodylitis (abbr. AS), systemic lupus erythematosus (abbr. SLE), multiple sclerosis (abbr. MS), psoriasis, alopecia areata, warm and cold autoimmune hemolytic anemia (abbr. AIHA), atypical haemolytic uremia, pernicious anemia, acute inflammatory diseases, autoimmune adrenalitis, chronic inflammatory demyelinating polyneuropathy (abbr. CIDP), Churg-Strauss syndrome, Cogan syndrome, CREST syndrome, pemphigus vulgaris and pemphigus *foliaceus*, bullous pemphigoid, polymyalgia rheumatica, polymyositis, primary biliary cirrhosis, pancreatitis, peritonitis, psoriatic arthritis, rheumatic fever, sarcoidosis, Sjogren's syndrome, scleroderma, celiac disease, stiff-man syndrome, Takayasu arteritis, transient gluten intolerance, autoimmune uveitis, vitiligo, polychondritis, dermatitis herpetiformis (abbr. DH) or Duhring's disease, fibromyalgia, Goodpasture syndrome, Guillain-Barre syndrome, Hashimoto thyroiditis, autoimmune hepatitis, inflammatory bowel disease (abbr. IBD), Crohn's disease, colitis ulcerosa, myasthenia gravis, immune complex disorders, glomerulonephritis, polyarteritis nodosa, anti-phospholipid syndrome, polyglandular autoimmune syndrome, idiopathic pulmonar fibrosis, idiopathic thrombocytopenic purpura (abbr. ITP), urticaria, autoimmune infertility, juvenile rheumatoid arthritis, sarcoidosis, autoimmune cardiomyopathy, Lambert-Eaton syndrome, lichen sclerosis, Lyme disease, Graves disease, Behçet's disease, Meniere's disease, reactive arthritis (Reiter's syndrome); infections with viruses such as HIV, HBV, HCV, CMV or intracellular parasites such as *Leishmania, Rickettsia, Chlamydia, Coxiella, Plasmodium, Brucella*, mycobacteria, *Listeria, Toxoplasma* and *Trypanosoma*; secondary damages of trauma; local inflammation, shock, anaphylactic shock, burn, septic shock, haemorrhagic shock, systemic inflammatory response syndrome (abbr. SIRS), multiple organ failure (abbr. MOF), asthma and allergy, vasculitides such as arteritis temporalis, vasculitis, vascular leakage, and atherosclerosis; acute injuries of the central nervous system, myocarditis, dermatomyositis, gingivitis, acute respiratory insufficiency, chronic obstructive pulmonary disease, stroke, myocardial infarction, reperfusion injury, neurocognitive dysfunction, burn, inflammatory diseases of the eye such as uveitis, age-related macular degeneration (abbr. AMD), diabetic retinopathy (abbr. DR), diabetic macular edema (abbr. DME), ocular pemphigoid, keratoconjunctivitis, Stevens-Johnson syndrome, and Graves ophthalmopathy; local manifestations of systemic diseases, inflammatory diseases of the vasculature, acute injuries of the central nervous system, type 1 and 2 diabetes, the manifestations of diabetes, SLE, and rheumatic disease in the eye, brain, vasculature, heart, lung, kidneys, liver, gastrointestinal tract, spleen, skin, bones, lymphatic system, blood or other organ systems, for the prevention and/or support and/or post-operative treatment of coronary artery bypass graft (abbr. CABG), off-pump coronary artery bypass graft (abbr. OPCABG), minimally invasive direct coronary artery bypass graft (abbr. MIDCAB), percutaneous transluminal coronary angioplasty (abbr. PTCA), thrombolysis, organ transplantation, and vessel clamping surgery; for the prevention of organ damage of a transplanted organ or of an organ to be transplanted or for use of treatment of transplant rejection for transplanted organs such as liver, kidney, intestine, lung, heart, skin, limb, cornea, Langerhans islet, bone marrow, blood vessels and pancreas; fetal rejection.

The various diseases and disorders for the treatment and/or prevention of which the nucleic acids can be used, may be grouped as follows:

1. Autoimmune/inflammatory diseases 1.1 Systemic autoimmune and/or inflammatory diseases comprising allergy, septic shock, secondary damages of trauma, warm and cold autoimmune hemolytic anemia (abbr. AIHA), systemic inflammatory response syndrome (abbr. SIRS), hemorrhagic shock, diabetes type 1, diabetes type 2, the manifestations of diabetes, diffuse scleroderma, periodontitis and its associates bone loss, polychondritis, polyglandular autoimmune syndrome, rheumatoid arthritis, systemic lupus erythematosus (abbr. SLE) and manifestations thereof, reactive arthritis (also known as Reiter's syndrome).

1.2 Autoimmune and/or inflammatory diseases of the gastro-intestinal tract comprising Crohn's disease, colitis ulcerosa, celiac disease, transient gluten intolerance, inflammatory bowel disease (abbr. IBD), pancreatitis, gastrointestinal allergic hypersensitivity, necrotizing enterocolitis.

1.3 Autoimmune and/or inflammatory diseases of the skin comprising psoriasis, urticaria, dermatomyositis, pemphigus vulgaris, pemphigus *foliaceus*, bullous pemphigoid, morphea/linear scleroderma, vitiligo, dermatitis herpetiformis (abbr. DH) or Duhring's disease, lichen sclerosis.

1.4 Autoimmune and/or inflammatory diseases of the vasculature comprising vasculitides (preferably arteritis temporalis), vasculitis, Henoch Schonlein purpura, anti-neutrophil cytoplasmic antibody (ANCA)-associated vasculitis, vascular leakage, polymyalgia rheumatica, atherosclerosis, Churg-Strauss syndrome, Takayasu arteritis, Goodpasture syndrome (=antiglomerular basement membrane disease; mostly affecting the kidneys glomeruli and the lungs), glomerulonephritis, polyarteritis nodosa, Behçet's disease 1.5 Autoimmune and/or inflammatory diseases of the nervous system comprising multiple sclerosis (abbr. MS), chronic inflammatory demyelinating polyneuropathy (abbr. CIDP), neurocognitive dysfunction, stiff-man syndrome, Guillain-Barre syndrome, myasthenia gravis, Lambert-Eaton syndrome, neuromyelitis optica (Devic syndrome).

1.6 Muscular skeletal autoimmune and/or inflammatory diseases comprising rheumatoid arthritis, rheumatic disease in the eye, brain, lung, kidneys, heart, liver, gastrointestinal tract, spleen, skin, bones, lymphatic system, blood or other organs, ankylosing spodylitis (abbr. AS), sarcoidosis, periodontitis and associated bone loss, polymyalgia rheumatica, polymyositis, psoriatic arthritis, rheumatic fever, polychondritis, fibromyalgia, juvenile rheumatoid arthritis, Lyme disease, reactive arthritis (also known as Reiter's syndrome).

1.7 Other autoimmune and/or inflammatory diseases comprise Cogan syndrome, autoimmune adrenalitis, immune complex disorders, Méniére's disease, local inflammations, alopecia areata, acute inflammatory diseases, primary biliary cirrhosis, Sjogren's syndrome, scleroderma, diffuse scleroderma, CREST syndrome, Morphea/linear scleroderma, autoimmune uveitis, Hashimoto thyroiditis (autoimmune thyroid destruction), Graves disease, autoimmune hepatitis, non-alcoholic steatohepatitis, glomerulonephritis, peritonitis, anti-phospholipid syndrome, idiopathic pulmonary fibrosis, renal fibrosis, hepatic fibrosis, autoimmune infertility, fetal rejection or miscarriage and graft-versus-host disease.
2. Diseases of the eye comprising uveitis, conjunctivitis, age-related macular degeneration (abbr. AMD), diabetic retinopathy (abbr. DR), diabetic macular edema (abbr. DME), retinal vessel occlusion, glaucoma, cataract, autoimmune retinal and intraocular inflammatory disease, ocular pemphigoid, keratoconjunctivitis, Stevens-Johnson syndrome, and Graves ophthalmopathy.
3. Reperfusion injuries and transplant rejections comprising stroke, myocardial infarction, reperfusion injuries, posttransplant thrombotic microangiopathy or organ damage to transplanted organs, such as liver (Arumugam et al. 2004), kidney (Arumugam et al. 2003), intestine, lung, heart, skin, limb, comea, islets of Langerhans (Tokodai et al. 2010), bone marrow, blood vessels and pancreas, kidney damage after organ or bone marrow transplantation.
4. Prevention of transplant rejection comprising transplant rejection of transplanted organs, such as liver, kidney, intestine, lung, heart, skin, limb, comea, islets of Langerhans, bone marrow, blood vessels and pancreas.
5. Cardiovascular diseases comprising atherosclerosis, myocarditis, myocardial infarction, stroke, pulmonary arterial hypertension (PAH), Abdominal Aortic Aneurism, inflammatory diseases of the vasculature, vasculitides, preferably arteritis temporalis, vasculitis, vascular leakage, the manifestations of diabetes, preeclempsia, autoimmune cardiomyopathy, vein host disease, arrythmogenic right ventrivular dysplasia/cardiomyopathy, for the prevention and/or support and/or post-operative treatment of coronary artery bypass graft (abbr. CABG).
6. Metabolic dysfunction comprising insulin resistance, glucose intolerance, adipose inflammation, and cardiovascular dysfunction in diet-induced obesity.
7. Respiratory diseases comprising asthma, acute respiratory insufficiency, acute lung injury, transfusion related lung injury, adult respiratory distress syndrome, chronic obstructive pulmonary disease, ventilator-induced lung injury, pneumonia and complications thereof.
8. Inflammatory diseases comprising inflammatory disease of the eye, autoimmune uveitis (Copland et al. 2010), conjunctivitis, vernal conjunctivitis, local manifestations of systemic diseases.
9. Acute reactions comprising secondary damages of trauma and fractures, shock, burn, anaphylactic shock, hemorrhagic shock, multiple organ failure (abbr. MOF), acute injuries of the central nervous system, acute injuries of the central nervous system, acute damage due to excessive C5a production by an activated coagulation system such as after organ or islet transplantation,
10. pain, acute pain, chronic pain, neuropathic pain, morphine tolerance and withdrawal-induced hyperalgesia.
11. Neurological and neurodegenerative disorders comprising neuropathies, Amyotrophic Lateral Sclerosis (ALS), Alzheimer's disease and Parkinson's disease (Farkas et al. 1998).
12. Infectious diseases comprising
12.1 bacterial infections, preferably meningitis, Lyme disease, reactive arthritis (also known as Reiter's syndrome), urinary tract and kidney infection, sepsis and its complications such as organ failure, cardiac dysfunction, systemic hypoperfusion, acidosis, adult respiratory distress syndrome, infections with intracellular pathogens (Klos et al. 2009),
12.2 viral infections, preferably HIV, HBV, HCV, CMV, viral meningitis
12.3 intracellular parasites, preferably *Leishmania, Rickettsia, Chlamydia, Coxiella, plasmodium*, especially cerebral malaria, *Brucella*, mycobacteria, *Listeria, Toxoplasma* and *Trypanosoma*.
13. Hemotological diseases comprising diseases associated with activation of coagulation and fibrinolytic systems disseminated intravascular coagulation (DIC) and/or thrombosis, pernicious anemia, warm and cold autoimmune hemolytic anemia (abbr. AIHA), anti-phospholipid syndrome and its associated complications, arterial and venous thrombosis, pregnancy complications such as recurrent miscarriage and fetal death, preeclampsia, placental insufficiency, fetal growth restriction, cervical remodeling and preterm birth, idiopathic thrombocytopenic purpura (abbr. ITP), atypical hemolytic uremic syndrome (aHUS), paroxysmal nocturnal hemoglobinuria (PNH) and allergic transfusion reactions.
14. Clinical complications associated with activation by biomaterials of complement and coagulation cascades occurring in procedures comprising hemodialysis, apheresis, visco-supplementation of arthritic joints, cardiopulmonary bypass, prosthetic vascular grafts and use of cardio vascular devices.

The nucleic acids according to the present invention may also be used in an intra-operative manner to avoid deleterious effects of the patient's immune system, more preferably for the prevention and/or support and/or post-operative treatment of coronary artery bypass graft (abbr. CABG), off-pump coronary artery bypass graft (abbr. OPCABG), minimally invasive direct coronary artery bypass graft (abbr. MIDCAB), percutaneous transluminal coronary angioplasty (abbr. PTCA), thrombolysis, organ transplantation, brain and spinal cord surgery, reconstructive surgery, and vessel clamping surgery, during any treatment with artificial ventilation or ventilation assistance to avoid lung ventilator-induced lung injury or secondary damages, such as vascular leakage and/or emphysema, for the prevention of organ damage of a transplanted organ or of an organ to be transplanted or for use of treatment of transplant rejection and reperfusion injury for transplanted organs, such as liver, kidney, intestine, lung, heart, skin, limb, cornea, islets of Langerhans, bone marrow, blood vessels and pancreas.

It is within the present invention that the medicament and pharmaceutical composition, respectively, containing a nucleic acid according to the present inventors may be used for the treatment in such way.

In a further embodiment, the medicament comprises a further pharmaceutically active agent.

Such further pharmaceutically active compounds are, among others but not limited thereto, those known to suppress the immune system such as calcineurin inhibitors, cyclosporin A, methotrexate, azathioprin, tacrolimus, rapamycin, chlorambucil, leflunomide, mycophenolate mofetil, brequinar, mizoribin, thalidomide, or deoxyspergualin. The further pharmaceutically active compound can be, in a further embodiment, also one of those compounds which reduce histamine production such as meclozin, clemastin, dimetinden, bamipin, ketotifen, cetirizin, loveceti-rizin, cesloratadin, azelastin, mizolastin, levocabastin, terfenadin, fexofenadin, or ebastin. Such compounds can also be, but are not limited to, steroids and are preferably selected from the group comprising corticosteroids like prednisone, methylprednisolone, hydrocortisone, dexamethasone, triamcinolone, betamethasone, effervescent, or budesonide.

Further, such compound can be one or several antibiotics such as, but not restricted to, aminoglycosides, P-lactam antibiotics, gyrase inhibitors, glycopeptide antibiotics, lincosamide, macrolide antibiotics, nitroimidazole derivatives, polypeptide antibiotics, sulfonamides, trimethoprim and tetracycline. Additionally, more specific anti-inflammatory or anti-angiogenic biologics can be used in combination such as bevacizumab, ranibizumab, IL-10, erlizumab, tolermab, rituximab, gomiliximab, basiliximab, daclizumab, HuMax-TAC, visilizumab, HuMaxCD4, clenoliximab, MAX 16H5, TNX 100, toralizumab, alemtuzumab, CY 1788, galiximab, pexelizumab, eculizumab, PMX-53, ETI 104, FG 3019, bertilimumab, 249417 (anti-factor IX) abciximab, YM 337, omalizumab, talizumab, fontolizumab, J695 (anti-IL12), HuMaxIL-15, mepolizumab, elsilimomab, HuDREG, anakinra, Xoma-052, adalimumab, infliximab, certolizumab, afelimomab, CytoFab, AME 527, Vapaliximab, bevacizumab, ranibizumab, vitaxin, belimumab, MLN 1202, volociximab, F200 (anti-α5β1), efalizumab, m60.11 (anti.CD11b), etanercept, onercept, rilonacept, abatacept, natalizumab, or siplizumab, tocilizumab, ustekinumab, ABT-874. Finally, the further pharmaceutically active agent may be a modulator of the activity of any other chemokine which can be a chemokine agonist or antagonist or a chemokine receptor agonist or antagonist whereby the chemokine can also be a chemotactic lipid. An example is the SIP receptor modulator fingolimod.

Alternatively, or additionally, such further pharmaceutically active agent is a further nucleic acid according to the present invention. Alternatively, the medicament comprises at least one more nucleic acid which binds to a target molecule different from C5a or exhibits a function which is different from the one of the nucleic acids according to the present invention.

In general the C5a antagonist can be combined with inhibitors of other proinflammatory molecules or their receptors. Examples for proinflammatory molecules whose action can be attenuated in combination with the C5a antagonist are IL-1, IL-2, IL-5, IL-6, IL-8, IL-10, IL-12, IL-13, IL-15, IL-16, IL-17, IL-18, IL-23, TNF, α4β7, α5β1, BlyS, cadherin, CCR2, CD11a, CD11b, CD125, CD130, CD16, CD18, CD2, CD20,CD22, CD23, CD25, CD28, CD3, CD30, CD4, CD40, CD40L, CD44, CD45R, CD54, CD62E, CD62L, CD68, CD8, CD80, CD86, CD95, CEP, gastrin-R, C1, C1-esterase, C5, factor D, MBL, complement receptor 1, CRTH2-receptor, CTGF, E- and P-selectin, eotaxin, factor IX, FGF-20, Fgl-2, GM-CSF, GP IIb/IIIa receptor, HMG1, ICAM-1, IgE, thymocytes, IFNγ, IFNr, IP-10, MCP-1, M-CSF receptor, MIF, MMP9, PDGF-D, SDF-1, TGFβ1, tissue factor, tyrosine kinase receptor, VAP-1, VCAM-1, VEGF, VLA1, von Willebrandt factor, sphingosine 1 Phosphate, ceramide-1 phosphate, and inhibitors of mitogens, e.g. inhibitors of lysophosphatidic acid.

Finally, the further pharmaceutically active agent may be a modulator of the activity of any other chemokine which can be a chemokine agonist or antagonist or a chemokine receptor agonist or antagonist. Alternatively, or additionally, such further pharmaceutically active agent is a further nucleic acid according to the present invention. Alternatively, the medicament comprises at least one more nucleic acid which binds to a target molecule different from C5a or exhibits a function which is different from the one of the nucleic acids according to the present invention.

It is within the present invention that the medicament is alternatively or additionally used, in principle, for the prevention of any of the diseases disclosed in connection with the use of the medicament for the treatment of said diseases. Respective markers therefore, i.e. for the respective diseases are known to the ones skilled in the art. Preferably, the respective marker is C5a.

In one embodiment of the medicament of the present invention, such medicament is for use in combination with other treatments for any of the diseases disclosed herein, particularly those for which the medicament of the present invention is to be used.

"Combination therapy" (or "co-therapy") includes the administration of a medicament of the invention and at least a second agent as part of a specific treatment regimen intended to provide the beneficial effect from the co-action of these therapeutic agents, i.e. the medicament of the present invention and said second agent. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected).

"Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to a subject a single capsule having a fixed ratio of each therapeutic agent or in multiple, single capsules for each of the therapeutic agents.

Sequential or substantially simultaneous administration of each therapeutic agent can be effected by any appropriate route including, but not limited to, topical routes, oral routes, intravenous routes, intramuscular routes, and direct absorption through mucous membrane tissues. The therapeutic agents can be administered by the same route or by different routes. For example, a first therapeutic agent of the combination selected may be administered by injection while the other therapeutic agents of the combination may be administered topically.

Alternatively, for example, all therapeutic agents may be administered topically or all therapeutic agents may be administered by injection. The sequence in which the therapeutic agents are administered is not narrowly critical unless noted otherwise. "Combination therapy" also can embrace the administration of the therapeutic agents as described above in further combination with other biologically active ingredients. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

As outlined in general terms above, the medicament according to the present invention can be administered, in principle, in any form known to the ones skilled in the art. A preferred route of administration is systemic administration, more preferably by parenteral administration, preferably by injection. Alternatively, the medicament may be administered locally. Other routes of administration comprise intramuscular, intraperitoneal, and subcutaneous, per orum, intranasal, intratracheal or pulmonary with preference given to the route of administration that is the least invasive, while ensuring efficiency.

Parenteral administration is generally used for subcutaneous, intramuscular or intravenous injections and infusions. Additionally, one approach for parenteral administration employs the implantation of a slow-release or sustained-released systems, which assures that a constant level of dosage is maintained, that are well known to the ordinary skill in the art.

Furthermore, preferred medicaments of the present invention can be administered in intranasal form via topical use of suitable intranasal vehicles, inhalants, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels, wherein the concentration of active ingredient would typically range from 0.01% to 15%, w/w or w/v.

The medicament of the present invention will generally comprise an effective amount of the active component(s) of the therapy, including, but not limited to, a nucleic acid molecule of the present invention, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the medicament of the present invention.

In a further aspect the present invention is related to a pharmaceutical composition. Such pharmaceutical composition comprises at least one of the nucleic acids according to the present invention and preferably a pharmaceutically acceptable vehicle. Such vehicle can be any vehicle or any binder used and/or known in the art. More particularly such binder or vehicle is any binder or vehicle as discussed in connection with the manufacture of the medicament disclosed herein. In a further embodiment, the pharmaceutical composition comprises a further pharmaceutically active agent.

The preparation of a medicament and a pharmaceutical composition will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including eye drops, creams, lotions, salves, inhalants and the like. The use of sterile formulations, such as saline-based washes, by surgeons, physicians or health care workers to treat a particular area in the operating field may also be particularly useful. Compositions may also be delivered via microdevice, microparticle or sponge.

Upon formulation, a medicament will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the individual or the subject to be treated. Specific amounts of active compound required for administration depend on the judgment of the practitioner and are peculiar to each individual.

A minimal volume of a medicament required to disperse the active compounds is typically utilized. Suitable regimes for administration are also variable, but would be typified by initially administering the compound and monitoring the results and then giving further controlled doses at further intervals.

For instance, for oral administration in the form of a tablet or capsule (e.g., a gelatin capsule), the active drug component, i.e. a nucleic acid molecule of the present invention and/or any further pharmaceutically active agent, also referred to herein as therapeutic agent(s) or active compound(s) can be combined with an oral, non-toxic, pharmaceutically acceptable inert carrier such as ethanol, glycerol, water and the like. Moreover, when desired or necessary, suitable binders, lubricants, disintegrating agents, and coloring agents can also be incorporated into the mixture. Suitable binders include starch, magnesium aluminum silicate, starch paste, gelatin, methylcellulose, sodium carboxymethylcellulose and/or polyvinylpyrrolidone, natural sugars such as glucose or beta-lactose, corn sweeteners, natural and synthetic gums such as acacia, tragacanth or sodium alginate, polyethylene glycol, waxes, and the like. Lubricants used in these dosage forms include sodium oleate, sodium stearate, magnesium stearate, sodium benzoate, sodium acetate, sodium chloride, silica, talcum, stearic acid, its magnesium or calcium salt and/or polyethyleneglycol, and the like. Disintegrators include, without limitation, starch, methyl cellulose, agar, bentonite, xanthan gum starches, agar, alginic acid or its sodium salt, or effervescent mixtures, and the like. Diluents, include, e.g., lactose, dextrose, sucrose, mannitol, sorbitol, cellulose and/or glycine.

The medicament of the invention can also be administered in such oral dosage forms as timed release and sustained release tablets or capsules, pills, powders, granules, elixirs, tinctures, suspensions, syrups and emulsions. Suppositories are advantageously prepared from fatty emulsions or suspensions.

The pharmaceutical composition or medicament may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating, or coating methods, and typically contain about 0.1% to 75%, preferably about 1% to 50%, of the active ingredient.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension. Additionally, solid forms suitable for dissolving in liquid prior to injection can be formulated.

For solid compositions, excipients include pharmaceutical grades of mannitol, lactose, starch, magnesium stearate, sodium saccharin, talcum, cellulose, glucose, sucrose, magnesium carbonate, and the like. The active compound defined above, may be also formulated as suppositories, using for example, polyalkylene glycols, for example, propylene glycol, as the carrier. In some embodiments, suppositories are advantageously prepared from fatty emulsions or suspensions.

The medicaments and nucleic acid molecules, respectively, of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, what is well known to the ordinary skill in the art. For example, the nucleic acid molecules described herein can be provided as a complex with a lipophilic compound or non-immunogenic, high molecular weight compound constructed using methods known in the art. Additionally, liposomes may bear such nucleic acid molecules on their surface for targeting and carrying cytotoxic agents internally to mediate cell killing. An example of nucleic-acid associated complexes is provided in U.S. Pat. No. 6,011,020.

The medicaments and nucleic acid molecules, respectively, of the present invention may also be coupled with soluble polymers as targetable drug carriers. Such polymers can include polyvinylpyrrolidone, pyran copolymer, polyhydroxypropyl-methacrylamide-phenol, polyhydroxyethyl-aspanamidephenol, or polyethyleneoxidepolylysine substituted with palmitoyl residues. Furthermore, the medicaments and nucleic acid molecules, respectively, of the present invention may be coupled to a class of biodegradable polymers useful in achieving controlled release of a drag, for example, polylactic acid, polyepsilon capro lactone, polyhydroxy butyric acid, polyorthoesters, polyacetals, polydihydropyrans, polycyanoacrylates and cross-linked or amphipathic block copolymers of hydrogels.

If desired, the pharmaceutical composition and medicament, respectively, to be administered may also contain minor amounts of non-toxic auxiliary substances such as wetting or emulsifying agents, pH buffering agents, and other substances such as for example, sodium acetate, and triethanolamine oleate.

The dosage regimen utilizing the nucleic acid molecules and medicaments, respectively, of the present invention is selected in accordance with a variety of factors including type, species, age, weight, sex and medical condition of the patient; the severity of the condition to be treated; the route of administration; the renal and hepatic function of the patient; and the particular aptamer or salt thereof employed. An ordinarily skilled physician or veterinarian can readily determine and prescribe the effective amount of the drug required to prevent, counter or arrest the progress of the condition.

Effective plasma levels of the nucleic acid according to the present invention preferably range from 500 fM to 500 µM in the treatment of any of the diseases disclosed herein.

The nucleic acid molecules and medicaments, respectively, of the present invention may preferably be administered in a single daily dose, every second or third day, weekly, every second week, in a single monthly dose or every third month.

It is within the present invention that the medicament as described herein constitutes the pharmaceutical composition disclosed herein.

In a further aspect the present invention is related to a method for the treatment of a subject who is in need of such treatment, whereby the method comprises the administration of a pharmaceutically active amount of at least one of the nucleic acids according to the present invention. In an embodiment, the subject suffers from a disease or is at risk to develop such disease, whereby the disease is any of those disclosed herein, particularly any of those diseases disclosed in connection with the use of any of the nucleic acids according to the present invention for the manufacture of a medicament.

It is to be understood that the nucleic acid as well as the antagonists according to the present invention can be used not only as a medicament or for the manufacture of a medicament, but also for cosmetic purposes, particularly with regard to the involvement of C5a in inflamed regional skin lesions. Therefore, a further condition or disease for the treatment or prevention of which the nucleic acid, the medicament and/or the pharmaceutical composition according to the present invention can be used, is inflamed regional skin lesions.

As preferably used herein a diagnostic or diagnostic agent or diagnostic means is suitable to detect, either directly or indirectly C5a, preferably C5a as described herein and more preferably C5a as described herein in connection with the various disorders and diseases described herein.

The diagnostic is suitable for the detection and/or follow-up of any of the disorders and diseases, respectively, described herein. Such detection is possible through the binding of the nucleic acids according to the present invention to C5a. Such binding can be either directly or indirectly be detected. The respective methods and means are known to the ones skilled in the art. Among others, the nucleic acids according to the present invention may comprise a label which allows the detection of the nucleic acids according to the present invention, preferably the nucleic acid bound to C5a. Such a label is preferably selected from the group comprising radioactive, enzymatic and fluorescent labels. In principle, all known assays developed for antibodies can be adopted for the nucleic acids according to the present invention whereas the target-binding antibody is substituted to a target-binding nucleic acid. In antibody-assays using unlabeled target-binding antibodies the detection is preferably done by a secondary antibody which is modified by radioactive, enzymatic and fluorescent labels and bind to the target-binding antibody at its Fc-fragment. In the case of a nucleic acid, preferably a nucleic acid according to the present invention, the nucleic acid is modified with such a label, whereby preferably such a label is selected from the group comprising biotin, Cy-3 and Cy-5, and such label is detected by an antibody directed against such label, e.g. an anti-biotin antibody, an anti-Cy3 antibody or an anti-Cy5 antibody, or—in the case that the label is biotin—the label is detected by streptavidin or avidin which naturally bind to biotin. Such antibody, streptavidin or avidin in turn is preferably modified with a respective label, e.g. a radioactive, enzymatic or fluorescent label (like an secondary antibody).

In a further embodiment the nucleic acid molecules according to the invention are detected or analysed by a second detection means, wherein the said detection means is a molecular beacon.

The methodology of molecular beacon is known to persons skilled in the art. In brief, nucleic acids probes which are also referred to as molecular beacons, are a reverse complement to the nucleic acids sample to be detected and hybridise because of this to a part of the nucleic acid sample to be detected. Upon binding to the nucleic acid sample the fluorophoric groups of the molecular beacon are separated which results in a change of the fluorescence signal, preferably a change in intensity. This change correlates with the amount of nucleic acids sample present.

It will be acknowledged that the detection of C5a using the nucleic acids according to the present invention will particularly allow the detection of C5a as defined herein.

In connection with the detection of C5a a preferred method comprises the following steps:
(a) providing a sample which is to be tested for the presence of C5a,
(b) providing a nucleic acid according to the present invention,
(c) reacting the sample with the nucleic acid, preferably in a reaction vessel
whereby step (a) can be performed prior to step (b), or step (b) can be preformed prior to step (a).

In a preferred embodiment a further step d) is provided, which consists in the detection of the reaction of the sample with the nucleic acid. Preferably, the nucleic acid of step b) is immobilised to a surface. The surface may be the surface of a reaction vessel such as a reaction tube, a well of a plate, or the surface of a device contained in such reaction vessel such as, for example, a bead. The immobilisation of the nucleic acid to the surface can be made by any means known to the ones skilled in the art including, but not limited to, non-covalent or covalent linkages. Preferably, the linkage is established via a covalent chemical bond between the surface and the nucleic acid. However, it is also within the present invention that the nucleic acid is indirectly immobilised to a surface, whereby such indirect immobilisation involves the use of a further component or a pair of interaction partners. Such further component is preferably a compound which specifically interacts with the nucleic acid to be immobilised which is also referred to as interaction partner, and thus mediates the attachment of the nucleic acid to the surface. The interaction partner is preferably selected from the group comprising nucleic acids, polypeptides, proteins and antibodies. Preferably, the interaction partner is an antibody, more preferably a monoclonal antibody. Alternatively, the interaction partner is a nucleic acid, preferably a functional nucleic acid. More preferably such functional nucleic acid is selected from the group comprising aptamers, Spiegelmers, and nucleic acids which are at least partially complementary to the nucleic acid. In a further alternative embodiment, the binding of the nucleic acid to the surface is mediated by a multi-partite interaction partner. Such multi-partite interaction partner is preferably a pair of interaction partners or an interaction partner consisting of a first member and a second member, whereby the first member is comprised by or attached to the nucleic acid and the second member is attached to or comprised by the surface. The multi-partite interaction partner is preferably selected from the group of pairs of interaction partners comprising biotin and avidin, biotin and streptavidin, and biotin and neutravidin. Preferably, the first member of the pair of interaction partners is biotin.

A preferred result of such method is the formation of an immobilised complex of C5a and the nucleic acid, whereby more preferably said complex is detected. It is within an embodiment that from the complex the C5a is detected.

A respective detection means which is in compliance with this requirement is, for example, any detection means which is specific for that/those part(s) of the C5a. A particularly preferred detection means is a detection means which is selected from the group comprising nucleic acids, polypeptides, proteins and antibodies, the generation of which is known to the ones skilled in the art.

The method for the detection of C5a also comprises that the sample is removed from the reaction vessel which has preferably been used to perform step c).

The method comprises in a further embodiment also the step of immobilising an interaction partner of C5a on a surface, preferably a surface as defined above, whereby the interaction partner is defined as herein and preferably as above in connection with the respective method and more preferably comprises nucleic acids, polypeptides, proteins and antibodies in their various embodiments. In this embodiment, a particularly preferred detection means is a nucleic acid according to the present invention, whereby such nucleic acid may preferably be labelled or non-labelled. In case such nucleic acid is labelled it can directly or indirectly be detected. Such detection may also involve the use of a second detection means which is, preferably, also selected from the group comprising nucleic acids, polypeptides, proteins and embodiments in the various embodiments described herein. Such detection means are preferably specific for the nucleic acid according to the present invention. In a more preferred embodiment, the second detection means is a molecular beacon. Either the nucleic acid or the second detection means or both may comprise in a preferred embodiment a detection label. The detection label is preferably selected from the group comprising biotin, a bromo-desoxyuridine label, a digoxigenin label, a fluorescence label, a UV-label, a radio-label, and a chelator molecule. Alternatively, the second detection means interacts with the detection label which is preferably contained by, comprised by or attached to the nucleic acid. Particularly preferred combinations are as follows:
the detection label is biotin and the second detection means is an antibody directed against biotin, or wherein
the detection label is biotin and the second detection means is an avidin or an avidin carrying molecule, or wherein
the detection label is biotin and the second detection means is a streptavidin or a streptavidin carrying molecule, or wherein
the detection label is biotin and the second detection means is a neutravidin or a neutravidin carrying molecule, or
wherein the detection label is a bromo-desoxyuridine and the second detection means is an antibody directed against bromo-desoxyuridine, or wherein
the detection label is a digoxigenin and the second detection means is an antibody directed against digoxigenin, or wherein
the detection label is a chelator and the second detection means is a radio-nuclide, whereby it is preferred that said detection label is attached to the nucleic acid. It is to be acknowledged that this kind of combination is also applicable to the embodiment where the nucleic acid is attached to the surface. In such embodiment it is preferred that the detection label is attached to the interaction partner.

Finally, it is also within the present invention that the second detection means is detected using a third detection means, preferably the third detection means is an enzyme, more preferably showing an enzymatic reaction upon detection of the second detection means, or the third detection means is a means for detecting radiation, more preferably radiation emitted by a radio-nuclide. Preferably, the third detection means is specifically detecting and/or interacting with the second detection means.

Also in the embodiment with an interaction partner of C5a being immobilised on a surface and the nucleic acid according to the present invention is preferably added to the complex formed between the interaction partner and the C5a, the sample can be removed from the reaction, more preferably from the reaction vessel where step c) and/or d) are preformed.

In an embodiment the nucleic acid according to the present invention comprises a fluorescence moiety and whereby the fluorescence of the fluorescence moiety is different upon complex formation between the nucleic acid and C5a and free C5a.

In a further embodiment the nucleic acid is a derivative of the nucleic acid according to the present invention, whereby the derivative of the nucleic acid comprises at least one fluorescent derivative of adenosine replacing adenosine. In a preferred embodiment the fluorescent derivative of adenosine is ethenoadenosine.

In a further embodiment the complex consisting of the derivative of the nucleic acid according to the present invention and the C5a is detected using fluorescence.

In an embodiment of the method a signal is created in step (c) or step (d) and preferably the signal is correlated with the concentration of C5a in the sample.

In a preferred aspect, the assays may be performed in 96-well plates, where components are immobilized in the reaction vessels as described above and the wells acting as reaction vessels.

The inventive nucleic acid may further be used as starting material for drug design. Basically there are two possible approaches. One approach is the screening of compound libraries whereas such compound libraries are preferably low molecular weight compound libraries. In an embodiment, the screening is a high throughput screening. Preferably, high throughput screening is the fast, efficient, trial-and-error evaluation of compounds in a target based assay.

In best case the analysis are carried by a colorimetric measurement. Libraries as used in connection therewith are known to the one skilled in the art.

Alternatively, the nucleic acid according to the present invention may be used for rational design of drugs. Preferably, rational drug design is the design of a pharmaceutical lead structure.

Starting from the 3-dimensional structure of the target which is typically identified by methods such as X-ray crystallography or nuclear magnetic resonance spectroscopy, computer programs are used to search through databases containing structures of many different chemical compounds. The selection is done by a computer, the identified compounds can subsequently be tested in the laboratory.

The rational design of drugs may start from any of the nucleic acid according to the present invention and involves a structure, preferably a three dimensional structure, which is similar to the structure of the inventive nucleic acids or identical to the binding mediating parts of the structure of the inventive nucleic acids. In any case such structure still shows the same or a similar binding characteristic as the inventive nucleic acids. In either a further step or as an alternative step in the rational design of drugs the preferably three dimensional structure of those parts of the nucleic acids binding to the neurotransmitter are mimicked by chemical groups which are different from nucleotides and nucleic acids. By this mimicry a compound different from the nucleic acids can be designed. Such compound is preferably a small molecule or a peptide.

In case of screening of compound libraries, such as by using a competitive assay which are known to the one skilled in the arts, appropriate C5a analogues, C5a agonists or C5a antagonists may be found. Such competitive assays may be set up as follows. The inventive nucleic acid, preferably a Spiegelmer which is a target binding L-nucleic acid, is coupled to a solid phase. In order to identify C5a analogues labelled C5a may be added to the assay. A potential analogue would compete with the C5a molecules binding to the Spiegelmer which would go along with a decrease in the signal obtained by the respective label. Screening for agonists or antagonists may involve the use of a cell culture assay as known to the ones skilled in the art.

The kit according to the present invention may comprise at least one or several of the inventive nucleic acids. Additionally, the kit may comprise at least one or several positive or negative controls. A positive control may, for example, be C5a, particularly the one against which the inventive nucleic acid is selected or to which it binds, preferably, in liquid form. A negative control may, e.g., be a peptide which is defined in terms of biophysical properties similar to C5a, but which is not recognized by the inventive nucleic acids. Furthermore, said kit may comprise one or several buffers. The various ingredients may be contained in the kit in dried or lyophilised form or solved in a liquid. The kit may comprise one or several containers which in turn may contain one or several ingredients of the kit. In a further embodiment, the kit comprises an instruction or instruction leaflet which provides to the user information on how to use the kit and its various ingredients.

The pharmaceutical and bioanalytical determination of the nucleic acid according to the present invention is elementarily for the assessment of its pharmacokinetic and biodynamic profile in several humors, tissues and organs of the human and non-human body. For such purpose, any of the detection methods disclosed herein or known to a person skilled in the art may be used.

In a further aspect of the present invention a sandwich hybridisation assay for the detection of the nucleic acid according to the present invention is provided. Within the detection assay a capture probe and a detection probe are used. The capture probe is complementary to the first part and the detection probe to the second part of the nucleic acid according to the present invention. Both, capture and detection probe, can be formed by DNA nucleotides, modified DNA nucleotides, modified RNA nucleotides, RNA nucleotides, LNA nucleotides and/or PNA nucleotides.

Hence, the capture probe comprise a sequence stretch complementary to the 5'-end of the nucleic acid according to the present invention and the detection probe comprise a sequence stretch complementary to the 3'-end of the nucleic acid according to the present invention. In this case the capture probe is immobilised to a surface or matrix via its 5'-end whereby the capture probe can be immobilised directly at its 5'-end or via a linker between of its 5'-end and the surface or matrix. However, in principle the linker can be linked to each nucleotide of the capture probe. The linker can be formed by hydrophilic linkers of skilled in the art or by D-DNA nucleotides, modified D-DNA nucleotides, D-RNA nucleotides, modified D-RNA nucleotides, D-LNA nucleotides, PNA nucleotides, L-RNA nucleotides, L-DNA nucleotides, modified L-RNA nucleotides, modified L-DNA nucleotides and/or L-LNA nucleotides.

Alternatively, the capture probe comprises a sequence stretch complementary to the 3'-end of the nucleic acid according to the present invention and the detection probe comprise a sequence stretch complementary to the 5'-end of the nucleic acid according to the present invention. In this case the capture probe is immobilised to a surface or matrix via its 3'-end whereby the capture probe can be immobilised directly at its 3'-end or via a linker between of its 3'-end and the surface or matrix. However, in principle, the linker can be linked to each nucleotide of the sequence stretch that is complementary to the nucleic acid according to the present invention.

The linker can be formed by hydrophilic linkers of skilled in the art or by D-DNA nucleotides, modified D-DNA nucleotides, D-RNA nucleotides, modified D-RNA nucleotides, D-LNA nucleotides, PNA nucleotides, L-RNA nucleotides, L-DNA nucleotides, modified L-RNA nucleotides, modified L-DNA nucleotides and/or L-LNA nucleotides.

The number of nucleotides of the capture and detection probe that may hybridise to the nucleic acid according to the present invention is variable and can be dependent from the number of nucleotides of the capture and/or the detection probe and/or the nucleic acid according to the present invention itself. The total number of nucleotides of the capture and the detection probe that may hybridise to the nucleic acid according to the present invention should be maximal the number of nucleotides that are comprised by the nucleic acid according to the present invention.

The minimal number of nucleotides (2 to 10 nucleotides) of the detection and capture probe should allow hybridisation to the 5'-end or 3'-end, respectively, of the nucleic acid according to the present invention. In order to realize high specificity and selectivity between the nucleic acid according to the present invention and other nucleic acids occurring in samples that are analyzed the total number of nucleotides of the capture and detection probe should be or maximal the number of nucleotides that are comprised by the nucleic acid according to the present invention.

Moreover the detection probe preferably carries a marker molecule or label that can be detected as previously described herein. The label or marker molecule can in principle be linked to each nucleotide of the detection probe. Preferably, the label or marker is located at the 5'-end or 3'-end of the detection probe, whereby between the nucleotides within the detection probe that are complementary to the nucleic acid according to the present invention, and the label a linker can be inserted. The linker can be formed by hydrophilic linkers of skilled in the art or by D-DNA nucleotides, modified D-DNA nucleotides, D-RNA nucleotides, modified D-RNA nucleotides, D-LNA nucleotides, PNA nucleotides, L-RNA nucleotides, L-DNA nucleotides, modified L-RNA nucleotides, modified L-DNA nucleotides and/or L-LNA nucleotides.

The detection of the nucleic acid according to the present invention can be carried out as follows:

The nucleic acid according to the present invention hybridises with one of its ends to the capture probe and with the other end to the detection probe. Afterwards unbound detection probe is removed by, e.g., one or several washing steps. The amount of bound detection probe which preferably carries a label or marker molecule, can be measured subsequently as, for example, outlined in more detail in WO/2008/052774 which is incorporated herein by reference.

As preferably used herein, the term treatment comprises in a preferred embodiment additionally or alternatively prevention and/or follow-up.

As preferably used herein, the terms disease and disorder shall be used in an interchangeable manner, if not indicated to the contrary.

As used herein, the term comprise is preferably not intended to limit the subject matter followed or described by such term. However, in an alternative embodiment the term comprises shall be understood in the meaning of containing and thus as limiting the subject matter followed or described by such term.

The various SEQ. ID. Nos., the chemical nature of the nucleic acid molecules according to the present invention and the target molecules C5a as used herein, the actual sequence thereof and the internal reference number is summarized in the following table.

TABLE 1

| SEQ ID NO. | Internal Reference | | Sequence |
|---|---|---|---|
| 1 | 274-B5-002 | L-RNA | GCCUGAUGUGGUGUUGAAGGGU UGUGGGGUGUCGACGCACAGGC |
| 2 | 274-D5-002 | L-RNA | GCCUGAUGUGGUGUUGAGGGGU UGUGGGGUGUCGACGCACAGGC |
| 3 | 274-C8-002 | L-RNA | GCCUGAUGUGGUGUUGAAGGGU UGUUGGGUGUCGACGCACAGGC |
| 4 | 274-C8-002-G14 (= NOX-D19001) | L-RNA | GCCUGAUGUGGUGGUGAAGGGU UGUUGGGUGUCGACGCACAGGC |
| 5 | 274-C5-002 | L-RNA | GCCUGAUGUGGUGGUGAGGGGU UGUGGGGUGUCGACGCACAGGC |
| 6 | 274-G6-002 | L-RNA | GCCUGAUGUGGUGGUGAGGGGA UGUGGGGUGUCGACGCACAGGC |
| 7 | 274-H6-002 | L-RNA | GCCUGAUGUGGUGUUGAGGGGC UGUGGGGUGUCGACGCACAGGC |
| 8 | NOX-D19001-D09 | L-RNA/L-DNA | GCCUGAUGd̲U̲GGUGGUGAAGGG UUGUUGGGU̲G̲UCGACGCACAGGC |

TABLE 1-continued

| SEQ ID NO. | Internal Reference | | Sequence |
|---|---|---|---|
| 9 | NOX-D19001-D16 | L-RNA/L-DNA | GCCUGAUGUGGUGGUdGAAGGG UUGUUGGGUGUCGACGCACAGGC |
| 10 | NOX-D19001-D17 | L-RNA/L-DNA | GCCUGAUGUGGUGGUGdAAGGG UUGUUGGGUGUCGACGCACAGGC |
| 11 | NOX-D19001-D30 | L-RNA/L-DNA | GCCUGAUGUGGUGGUGAAGGGUU GUUGGGdUGUCGACGCACAGGC |
| 12 | NOX-D19001-D32 | L-RNA/L-DNA | GCCUGAUGUGGUGGUGAAGGGUU GUUGGGUGdUCGACGCACAGGC |
| 13 | NOX-D19001-D40 | L-RNA/L-DNA | GCCUGAUGUGGUGGUGAAGGGUU GUUGGGUGUCGACGCAdCAGGC |
| 14 | NOX-D19001-D09-30 | L-RNA/L-DNA | GCCUGAUGdUGGUGGUGAAGGGU UGUUGGGdUGUCGACGCACAGGC |
| 15 | NOX-D19001-D09-32 | L-RNA/L-DNA | GCCUGAUGdUGGUGGUGAAGGGU UGUUGGGUGdUCGACGCACAGGC |
| 16 | NOX-D19001-D09-40 | L-RNA/L-DNA | GCCUGAUGdUGGUGGUGAAGGGU UGUUGGGUGUCGACGCAdCAGGC |
| 17 | NOX-D19001-D30-32 | L-RNA/L-DNA | GCCUGAUGUGGUGGUGAAGGGUU GUUGGGdUGdUCGACGCACAGGC |
| 18 | NOX-D19001-D30-40 | L-RNA/L-DNA | GCCUGAUGUGGUGGUGAAGGGUU GUUGGGdUGUCGACGCAdCAGGC |
| 19 | NOX-D19001-D32-40 | L-RNA/L-DNA | GCCUGAUGUGGUGGUGAAGGGUU GUUGGGUGdUCGACGCAdCAGGC |
| 20 | NOX-D19001-D09-30-32 | L-RNA/L-DNA | GCCUGAUGdUGGUGGUGAAGGGUU GUUGGGdUGdUCGACGCACAGGC |
| 21 | NOX-D19001-D09-30-40 | L-RNA/L-DNA | GCCUGAUGdUGGUGGUGAAGGGUU GUUGGGdUGUCGACGCAdCAGGC |
| 22 | NOX-D19001-D09-32-40 | L-RNA/L-DNA | GCCUGAUGdUGGUGGUGAAGGGUU GUUGGGUGdUCGACGCAdCAGGC |
| 23 | NOX-D19001-D30-32-40 | L-RNA/L-DNA | GCCUGAUGUGGUGGUGAAGGGUUG UUGGGdUGdUCGACGCAdCAGGC |
| 24 | NOX-D19001-D09-30-32-40 | L-RNA/L-DNA | GCCUGAUGdUGGUGGUGAAGGGUU GUUGGGdUGdUCGACGCAdCAGGC |
| 25 | NOX-D19001-D09-16-30-32-40 | L-RNA/L-DNA | GCCUGAUGdUGGUGGUdGAAGGGU UGUUGGGdUGdUCGACGCAdCAGGC |
| 26 | NOX-D19001-D09-17-30-32-40 | L-RNA/L-DNA | GCCUGAUGdUGGUGGUGdAAGGGUU GUUGGGdUGdUCGACGCAdCAGGC |
| 27 | NOX-D19001-D09-16-17-30-32-40 (= NOX-D19001-6xDNA) | L-RNA/L-DNA | GCCUGAUGdUGGUGGUdGdAAGGGU UGUUGGGdUGdUCGACGCAdCAGGC |
| 28 | NOX-D19001-6xDNA-007 | L-RNA/L-DNA | CCUGAUGdUGGUGGUdGdAAGG GUUGUUGGGdUGdUCGACGCAdCAGGC |
| 29 | NOX-D19001-6xDNA-008 | L-RNA/L-DNA | CUGAUGdUGGUGGUdGdAAGGG UUGUUGGGdUGdUCGACGCAdCAGGC |
| 30 | NOX-D19001-6xDNA-009 | L-RNA/L-DNA | UGAUGdUGGUGGUdGdAAGGGUUG UUGGGdUGdUCGACGCAdCAGGC |
| 31 | NOX-D19001-6xDNA-010 | L-RNA/L-DNA | GAUGdUGGUGGUdGdAAGGGUUG UUGGGdUGdUCGACGCAdCAGGC |

TABLE 1-continued

| SEQ ID NO. | Internal Reference | | Sequence |
|---|---|---|---|
| 32 | NOX-D19001-6xDNA-011 | L-RNA/L-DNA | GCUGAUGdUGGUGGUdGdAAGGG UUGUUUGGGdUGdUCGACGCAdCA GC |
| 33 | NOX-D19001-6xDNA-012 | L-RNA/L-DNA | GUGAUGdUGGUGGUdGdAAGGGU UGUUGGGdUGdUCGACGCAdCAC |
| 34 | NOX-D19001-6xDNA-013 | L-RNA/L-DNA | UGAUGdUGGUGGUdGdAAGGGUU GUUGGGdUGdUCGACGCAdCA |
| 35 | NOX-D19001-6xDNA-018 | L-RNA/L-DNA | GCCGAUGdUGGUGGUdGdAAGGGU UGUUGGGdUGdUCGACGCAdCGGC |
| 36 | NOX-D19001-6XDNA-019 | L-RNA/L-DNA | GGCGAUGdUGGUGGUdGdAAGGGU UGUUGGGdUGdUCGACGCAdCGCC |
| 37 | NOX-D19001-6xDNA-020 (= NOX-D20001) | L-RNA/L-DNA | GCGAUGdUGGUGGUdGdAAGGGUU GUUGGGdUGdUCGACGCAdCGC |
| 38 | NOX-D19001-6xDNA-021 | L-RNA/L-DNA | CUGAUGdUGGUGGUdGdAAGGGUU GUUGGGdUGdUCGACGCAdCAGC |
| 39 | NOX-D19001-6xDNA-022 | L-RNA/L-DNA | UGAUGdUGGUGGUdGdAAGGGUUG UUGGGdUGdUCGACGCAdCAGC |
| 40 | NOX-D19001-6xDNA-023 | L-RNA/L-DNA | CGAUGdUGGUGGUdGdAAGGGUU GUUGGGdUGdUCGACGCAdCAGC |
| 41 | NOX-D19001-6xDNA-024 | L-RNA/L-DNA | GAUGdUGGUGGUdGdAAGGGUUG UUGGGdUGdUCGACGCAdCAGC |
| 42 | NOX-D19001-6xDNA-025 | L-RNA/L-DNA | GCUGAUGdUGGUGGUdGdAAGGGU UGUUGGGdUGdUCGACGCAdCAC |
| 43 | NOX-D19001-6xDNA-026 | L-RNA/L-DNA | GCUGAUGdUGGUGGUdGdAAGGGU UGUUGGGdUGdUCGACGCAdCC |
| 44 | NOX-D19001-6xDNA-027 | L-RNA/L-DNA | GCUGAUGdUGGUGGUdGdAAGGGU UGUUGGGdUGdUCGACGCAdCdCA |
| 45 | NOX-D19001-6xDNA-028 | L-RNA/L-DNA | CGAUGdUGGUGGUdGdAAGGGUUG UUGGGdUGdUCGACGCAdCGC |
| 46 | NOX-D19001-6xDNA-029 | L-RNA/L-DNA | GAUGdUGGUGGUdGdAAGGGUUGU UGGGdUGdUCGACGCAdCGC |
| 47 | NOX-D19001-6xDNA-030 | L-RNA/L-DNA | GCGAUGdUGGUGGUdGdAAGGGUU GUUGGGdUGdUCGACGCAdCC |
| 48 | NOX-D19001-6XDNA-032 | L-RNA/L-DNA | GCGAUGdUGGUGGUdGdAAGGGUU GUUGGGdUGdUCGACGCAdC |
| 49 | NOX-D19001-6xDNA-033 | L-RNA/L-DNA | GGAUGdUGGUGGUdGdAAGGGUUG UUGGGdUGdUCGACGCAdCC |
| 50 | human C5a | L-protein | TLQKKIEEIAAKYKHSWKKCCYDGA CWNDETCEQRAARISLGPRCIKAF TECCWASQLRANISHKDMQLGR |
| 51 | rat C5a | L-protein | DLQLLHQKVEEQAAKYKHRVPKKCCY DGARENKYETCEQRVARVTIGPHCIR AFNECCTIADKIRKESHHKGMLLGR |
| 52 | mouse C5a | L-protein | NLHLLRQKIEEQAAKYKHSVPKKCCY DGARVNFYETCEERVARVTIGPLCIR AFNECCTIANKIRKESPHKPVQLGR |
| 53 | Human C5, alpha chain | L-protein | TLQKKIEEIAAKYKHSVVKKCCYDG ACVNNDETCEQRAARISLGPRCIKA FTECCVVASQLRANISHKDMQLGRL HMKTLLPVSKPEIRSYFPESWLWEV HLVPRRKQLQFALPDSLTTWEIQGI GISNTGICVADTVKAKVFKDVFLEM NIPYSVVRGEQIQLKGTVYNYRTSG MQFCVKMSAVEGICTSESPVIDHQG |

TABLE 1-continued

| SEQ ID NO. | Internal Reference | | Sequence |
|---|---|---|---|
| | | | TKSSKCVRQKVEGSSSHLVTFTVLP |
| | | | LEIGLHNINFSLETWFGKEILVKTL |
| | | | RVVPEGVKRESYSGVTLDPRGIYGT |
| | | | ISRRKEFPYRIPLDLVPKTEIKRIL |
| | | | SVKGLLVGEILSAVLSQEGINILTH |
| | | | LPKGSAEAELMSVVPVFYVFHYLET |
| | | | GNHWNIFHSDPLIEKQKLKKKLKEG |
| | | | MLSIMSYRNADYSYSVWKGGSASTW |
| | | | LTAFALRVLGQVNKYVEQNQNSICN |
| | | | SLLWLVENYQLDNGSFKENSQYQPI |
| | | | KLQGTLPVEARENSLYLTAFTVIGI |
| | | | RKAFDICPLVKIDTALIKADNFLLE |
| | | | NTLPAQSTFTLAISAYALSLGDKTH |
| | | | PQFRSIVSALKREALVKGNPPIYRF |
| | | | WKDNLQHKDSSVPNTGTARMVETTA |
| | | | YALLTSLNLKDINYVNPVIKWLSEE |
| | | | QRYGGGFYSTQDTINAIEGLTEYSL |
| | | | LVKQLRLSMDIDVSYKHKGALHNYK |
| | | | MTDKNFLGRPVEVLLNDDLIVSTGF |
| | | | GSGLATVHVTTVVHKTSTSEEVCSF |
| | | | YLKIDTQDIEASHYRGYGNSDYKRI |
| | | | VACASYKPSREESSSGSSHAVMDIS |
| | | | LPTGISANEEDLKALVEGVDQLFTD |
| | | | YQIKDGHVILQLNSIPSSDFLCVRF |
| | | | RIFELFEVGFLSPATFTVYEYHRPD |
| | | | KQCTMFYSTSNIKIQKVCEGAACKC |
| | | | VEADCGQMQEELDLTISAETRKQTA |
| | | | CKPEIAYAYKVSITSITVENVFVKY |
| | | | KATLLDIYKTGEAVAEKDSEITFIK |
| | | | KVTCTNAELVKGRQYLIMGKEALQI |
| | | | KYNFSFRYIYPLDSLTWIEYWPRDT |
| | | | TCSSCQAFLANLDEFAEDIFLNGC |
| 54 | Rhesus monkey C5a | | MLQEKIEEIAAKYKHLVVKKCCYDG VRINHDETCEQRAARISVGPRCVKA FTECCVVASQLRANNSHKDLQLGR |
| 55 | NOX-D19001-020 | | GCGAUGUGGUGGUGAAGGGUUGUU GGGUGUCGACGCACGC |
| 56 | NOX-D19001-1xDNA-020 | L-RNA/L-DNA | GCGAUGdUGGUGGUGAAGGGUUGU UGGGUGUCGACGCACGC |
| 57 | NOX-D19001-2xDNA-020 | L-RNA/L-DNA | GCGAUGdUGGUGGUGAAGGGUUGU UGGGdUGUCGACGCACGC |
| 58 | NOX-D19001-3xDNA-020 | L-RNA/L-DNA | GCGAUGdUGGUGGUGAAGGGUU GUUGGGdUGdUCGACGCACGC |
| 59 | NOX-D19001-2dU-1dC-020 (= NOX-D21001) | L-RNA/L-DNA | GCGAUGdUGGUGGUGAAGGGUU GUUGGGdUGUCGACGCAdCGC |
| 60 | NOX-D19001-3dU-1dC-020 | L-RNA/L-DNA | GCGAUGdUGGUGGUGAAGGGUU GUUGGGdUGdUCGACGCAdCGC |
| 61 | | L-RNA/L-DNA | AUGn$_1$GGUGKUn$_2$n$_3$RGGGHU GUKGGGn$_4$Gn$_5$CGACGCA wherein n$_1$ is U or dU, n$_2$ is G or dG, n$_3$ is A or dA, n$_4$ is U or dU, n$_5$ is U or dU |
| 62 | | L-RNA/L-DNA | AUGn$_1$GGUGUUn$_2$n$_3$AGGGUUG UGGGGn$_4$Gn$_5$CGACGCA wherein n$_1$ is U or dU, n$_2$ is G or dG, n$_3$ is A or dA, n$_4$ is U or dU, n$_5$ is U or dU |
| 63 | | L-RNA/L-DNA | AUGn$_1$GGUGUUn$_2$n$_3$GGGGUUG UGGGGn$_4$Gn$_5$CGACGCA wherein n$_1$ is U or dU, n$_2$ is G or dG, |

TABLE 1-continued

| SEQ ID NO. | Internal Reference | Sequence |
|---|---|---|
| | | $n_3$ is A or dA, |
| | | $n_4$ is U or dU, |
| | | $n_5$ is U or dU |
| 64 | L-RNA/L-DNA | AUGn$_1$GGUGUUn$_2$n$_3$AGGGUUGUUGGGn$_4$Gn$_5$CGACGCA wherein n$_1$ is U or dU, n$_2$ is G or dG, n$_3$ is A or dA, n$_4$ is U or dU, n$_5$ is U or dU |
| 65 | L-RNA/L-DNA | AUGn$_1$GGUGGUn$_2$n$_3$AGGGUUGUUGGGn$_4$Gn$_5$CGACGCA wherein n$_1$ is U or dU, n$_2$ is G or dG, n$_3$ is A or dA, n$_4$ is U or dU, n$_5$ is U or dU |
| 66 | L-RNA/L-DNA | AUGn$_1$GGUGGUn$_2$n$_3$GGGGUUGUGGGGn$_4$Gn$_5$CGACGCA wherein n$_1$ is U or dU, n$_2$ is G or dG, n$_3$ is A or dA, n$_4$ is U or dU, n$_5$ is U or dU |
| 67 | L-RNA/L-DNA | AUGn$_1$GGUGGUn$_2$n$_3$GGGGAUGUGGGGn$_4$Gn$_5$CGACGCA wherein n$_1$ is U or dU, n$_2$ is G or dG, n$_3$ is A or dA, n$_4$ is U or dU, n$_5$ is U or dU |
| 68 | L-RNA/L-DNA | AUGn$_1$GGUGUUn$_2$n$_3$GGGGCUGUGGGGn$_4$Gn$_5$CGACGCA wherein n$_1$ is U or dU, n$_2$ is G or dG, n$_3$ is A or dA, n$_4$ is U or dU, n$_5$ is U or dU |
| 69 | L-RNA/L-DNA | AUGUGGUGKUGARGGGHUGUKGGGUGUCGACGCA |
| 70 | L-RNA/L-DNA | AUGUGGUGUUGAAGGGUUGUUGGGUGUCGACGCA |
| 71 | L-RNA/L-DNA | AUGUGGUGGUGAAGGGUUGUUGGGUGUCGACGCA |
| 72 | L-RNA/L-DNA | AUGUGGUGGUGAGGGGUUGUGGGGUGUCGACGCA |
| 73 | L-RNA/L-DNA | AUGdUGGUGGUGAAGGGUUGUUGGGUGUCGACGCA |
| 74 | L-RNA/L-DNA | AUGUGGUGGUdGAAGGGUUGUUGGGUGUCGACGCA |
| 75 | L-RNA/L-DNA | AUGUGGUGGUGdAAGGGUUGUUGGGUGUCGACGCA |
| 76 | L-RNA/L-DNA | AUGUGGUGGUGAAGGGUUGUUGGGdUGUCGACGCA |
| 77 | L-RNA/L-DNA | AUGUGGUGGtJGAAGGGUUGUUGGGUGdUCGACGCA |
| 78 | L-RNA/L-DNA | AUGdUGGUGGUGAAGGGUUGUUGGGdUGUCGACGCA |
| 79 | L-RNA/L-DNA | AUGdUGGUGGUGAAGGGUUGUUGGGUGdUCGACGCA |

TABLE 1-continued

| SEQ ID NO. | Internal Reference | | Sequence |
|---|---|---|---|
| 80 | | L-RNA/L-DNA | AUGUGGUGGUGAAGGGUUGUUG GGdUGdUCGACGCA |
| 81 | | L-RNA/L-DNA | AUGdUGGUGGUGAAGGGUUGU UGGGdUGdUCGACGCA |
| 82 | | L-RNA/L-DNA | AUGdUGGUGGUdGAAGGGUUGU UGGGdUGdUCGACGCA |
| 83 | | L-RNA/L-DNA | AUGdUGGUGGUGdAAGGGUUGU UGGGdUGdUCGACGCA |
| 84 | | L-RNA/L-DNA | AUGdUGGUGGUdGdAAGGGUUG UUGGGdUGdUCGACGCA |
| 85 | 274-H6-002 | D-RNA | GCCUGAUGUGGUGUUGAGGGGC UGUGGGGUGUCGACGCACAGGC |
| 86 | 274-D5-002 | D-RNA | GCCUGAUGUGGUGUUGAGGGGU UGUGGGGUGUCGACGCACAGGC |
| 87 | revNOX-D19 | L-RNA/L-DNA | 40kDaPEG-CGGACACGCAGCUG UGGGUUGUUGGGAAGUGGUGGUG UAGUCCG |
| 88 | revNOX-D21 | L-RNA/L-DNA | 40kDaPEG--CGdCACGCAGCUG dUGGGUUGUUGGGAAGUGGUGGd UGUAGCG |
| 89 | Biotinylated mouse-D-C5a | D-protein | LLRQKIEEQAAKYKHSVPKKCCY DGARVNFYETCEERVARVTIGPL CIRAFNECCTIANKIRKESPHKP VQLGR- Biotin |
| 90 | NOX-D19001-5'40kDa-PEG (= NOX-D19) | L-RNA/L-DNAC | 40kDaPEG-GCCUGAUGUGGUGG UGAAGGGUUGUUGGGUGUCGACG ACAGGC |
| 91 | NOX-D19001-6xDNA-020-5'40kDa-PEG (= NOX-D20) | L-RNA/L-DNA | 40kDaPEG-GCGAUGdUGGUGG UdGdAAGGGUUGUUGGGdUGdU CGACGCAdCGC |
| 92 | NOX-D19001-2dU-1dC-020-5'40kDa-PEG (= NOX-D21) | L-RNA/L-DNA | 40kDaPEG-GCGAUGdUGGUGG UGAAGGGUUGUUGGGdUGUCGA CGCAdCGC |
| 93 | human des-ArgC5a | L-protein | TLQKKIEEIAAKYKHSVVKKCCYDG ACVNNDETCEQRAARISLGPRCIKA FTECCVVASQLRANISHKDMQLG |
| 94 | mouse des-ArgC5a | L-protein | NLHLLRQKIEEQAAKYKHSVPKKCCY DGARVNFYETCEERVARVTIGPLCI RAFNECCTIANKIRKESPHKPVQLG |

The present invention is further illustrated by the figures, examples and the sequence listing from which further features, embodiments and advantages may be taken, wherein FIG. 1 shows an alignment of sequences of nucleic acid molecules capable of binding human and mouse C5a including the $K_D$ value and relative binding activity to human and mouse C5a as determined by surface plasmon resonance measurement;

FIG. 2 shows derivatives of nucleic acid molecule NOX-D19001 with a single ribonucleotide to 2'-deoxyribonucleotide substitution including the $K_D$ value and relative binding activity to human C5a as determined by surface plasmon resonance measurement;

FIG. 3 shows derivatives of nucleic acid molecule NOX-D19001 with two, three, four, five or six ribonucleotide to 2'-deoxyribonucleotide substitutions including the $K_D$ value and relative binding activity to human C5a as determined by surface plasmon resonance measurement;

Figure 6:
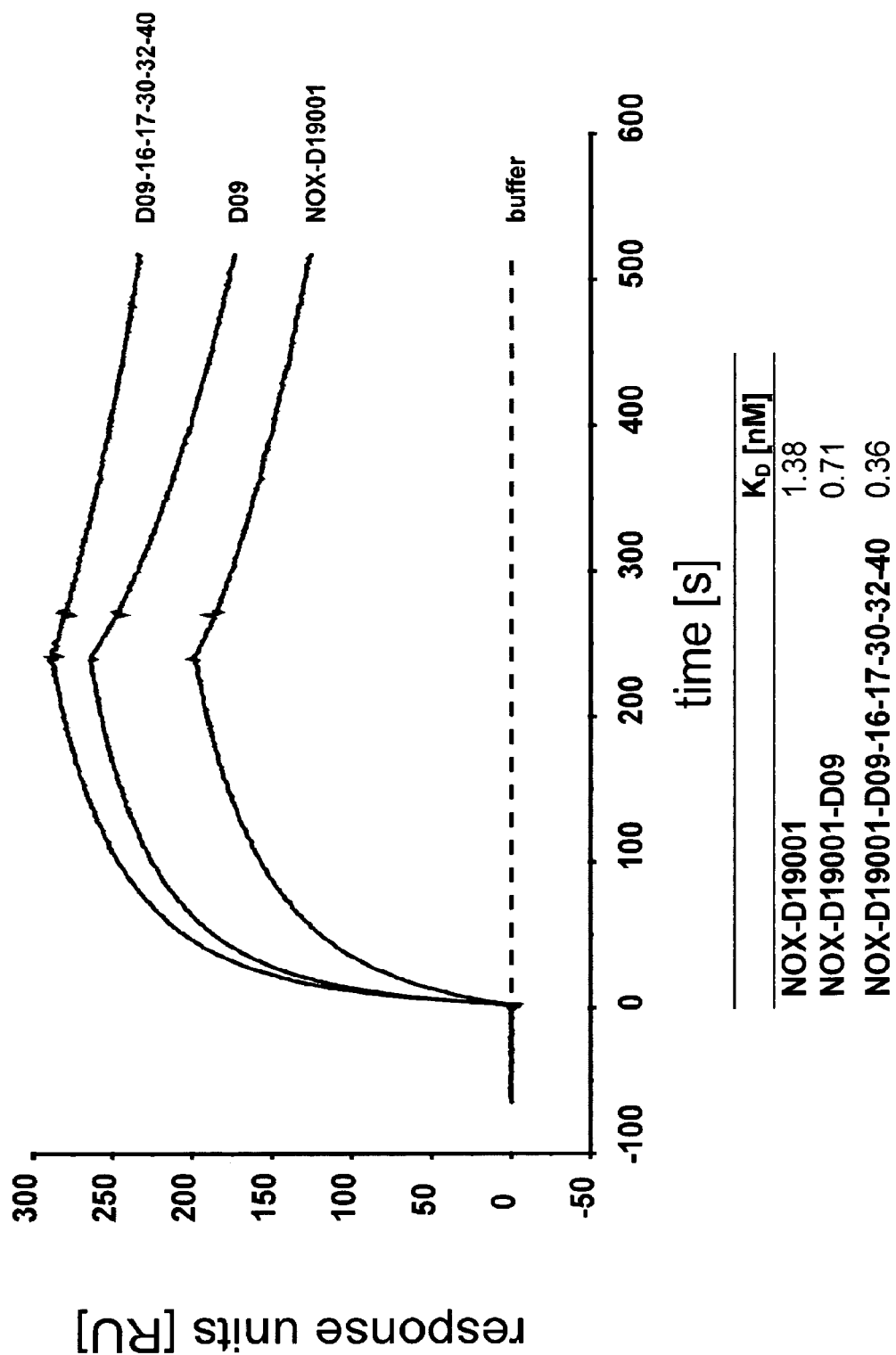
Figure 7:
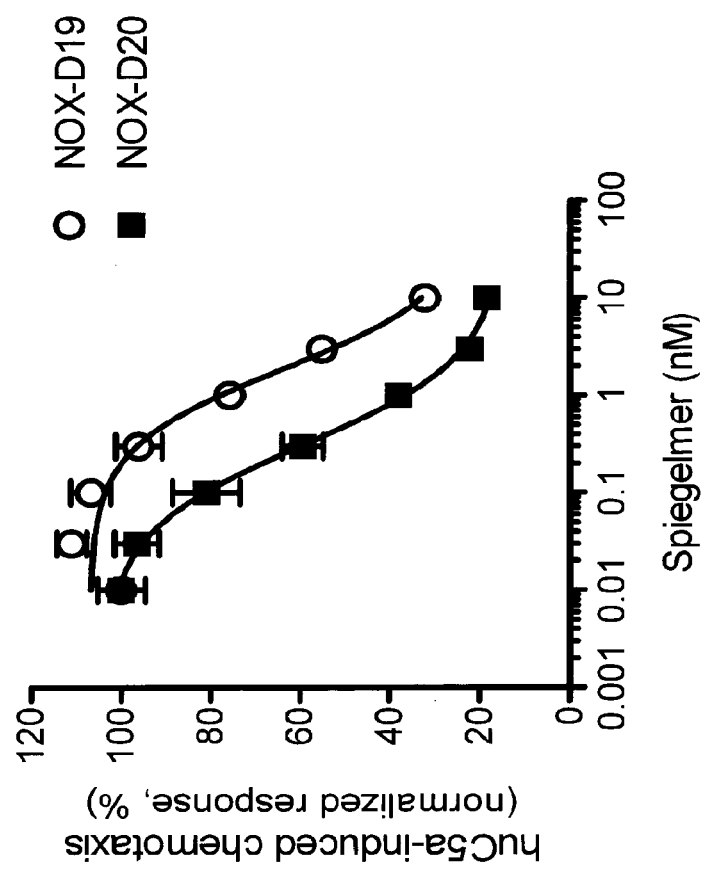
Figure 8:
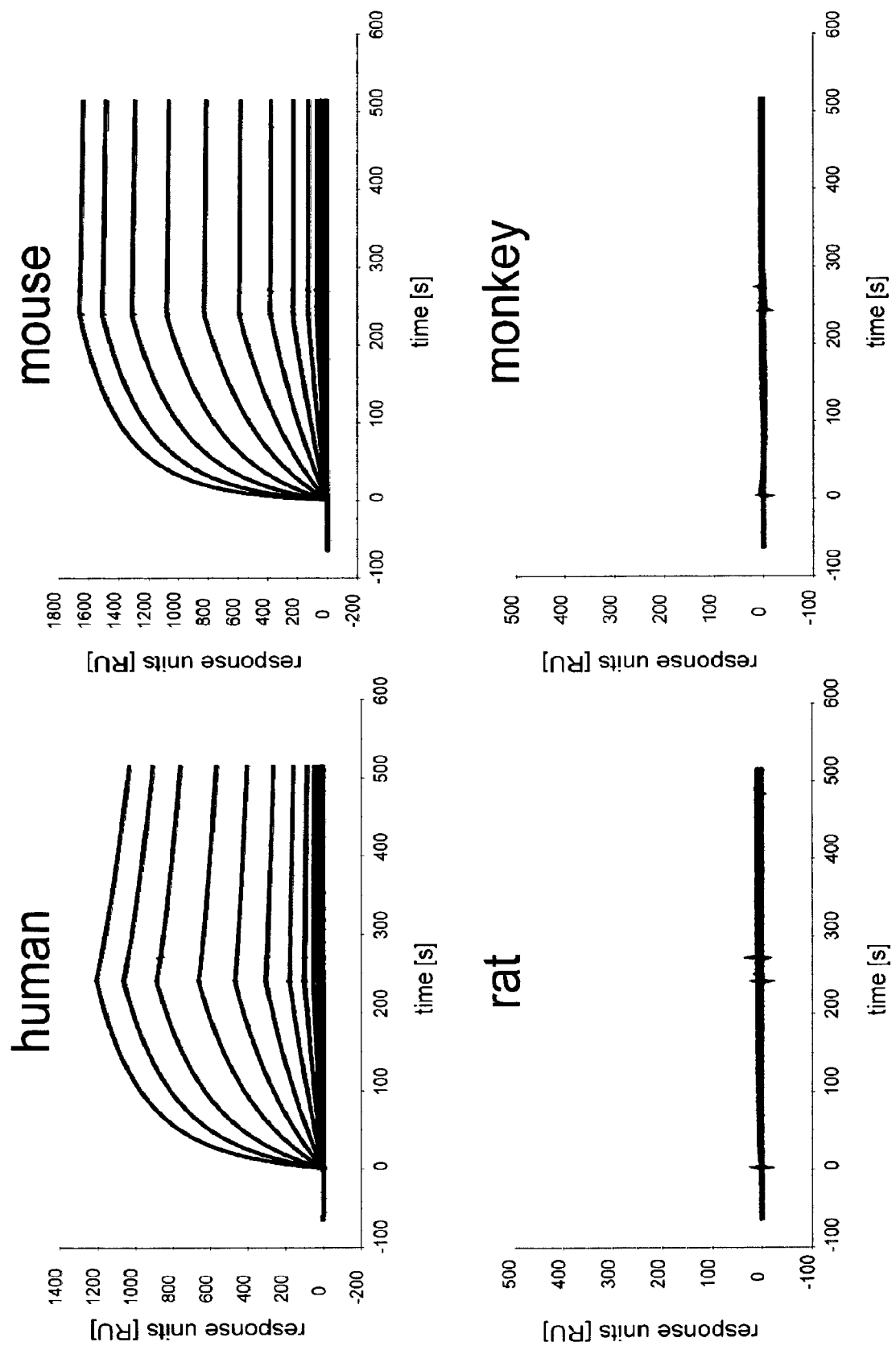
Figure 9:
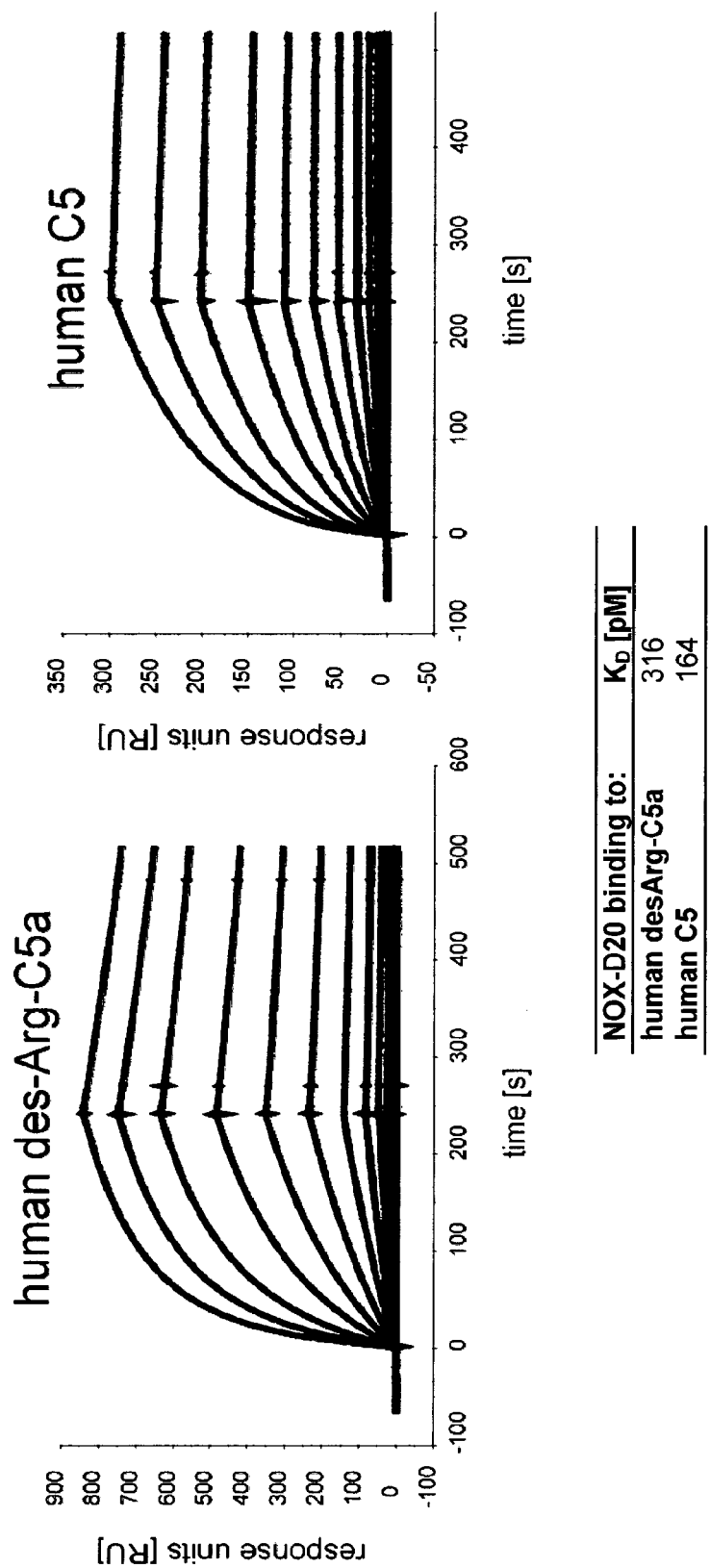
Figure 10:
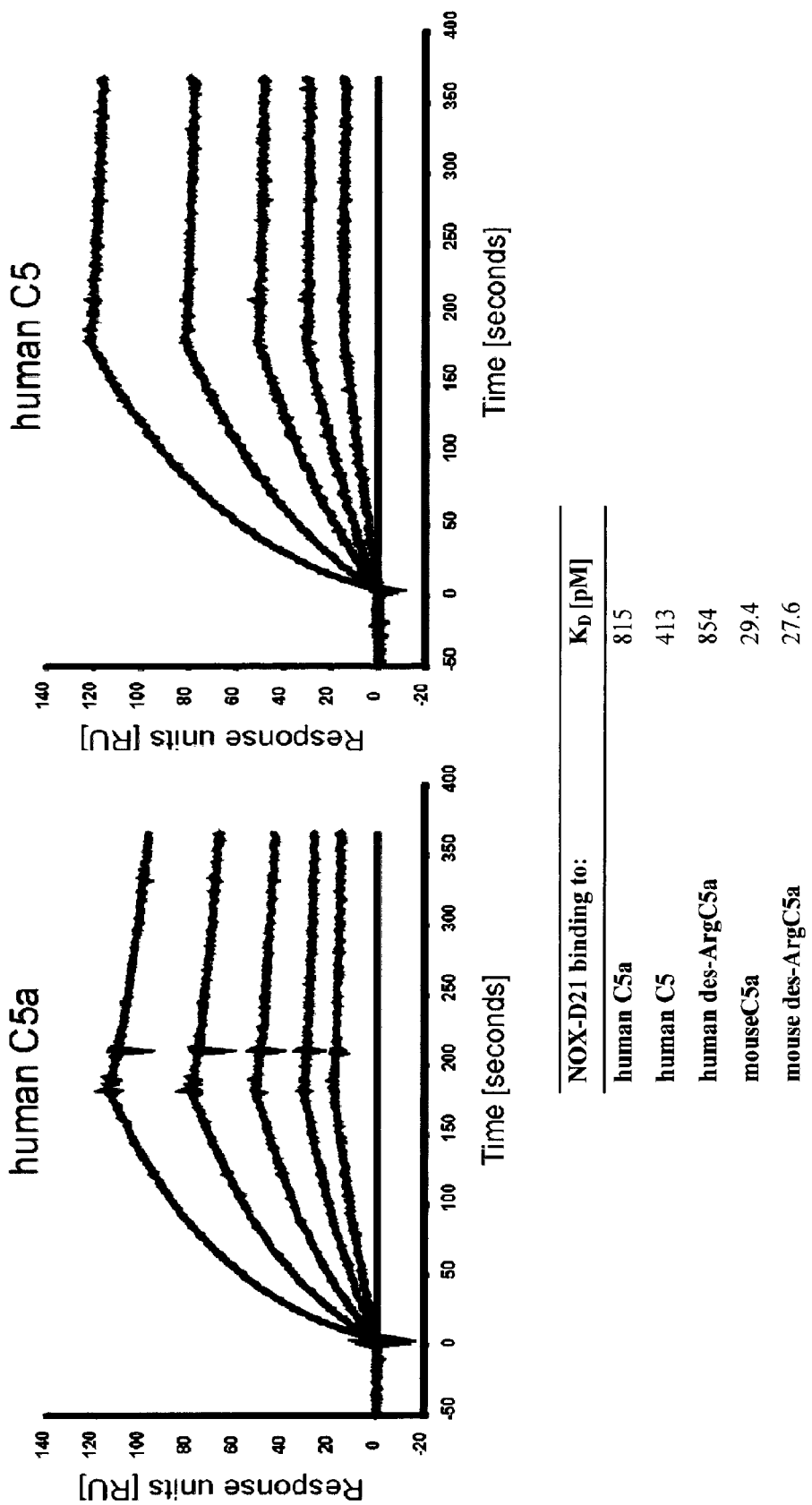
Figure 12A:
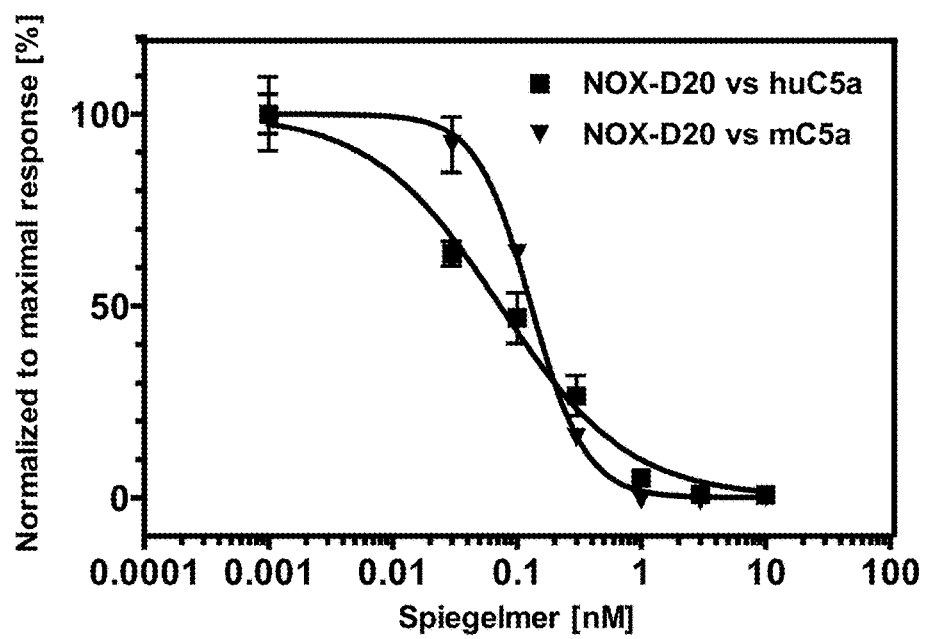
Figure 12B:
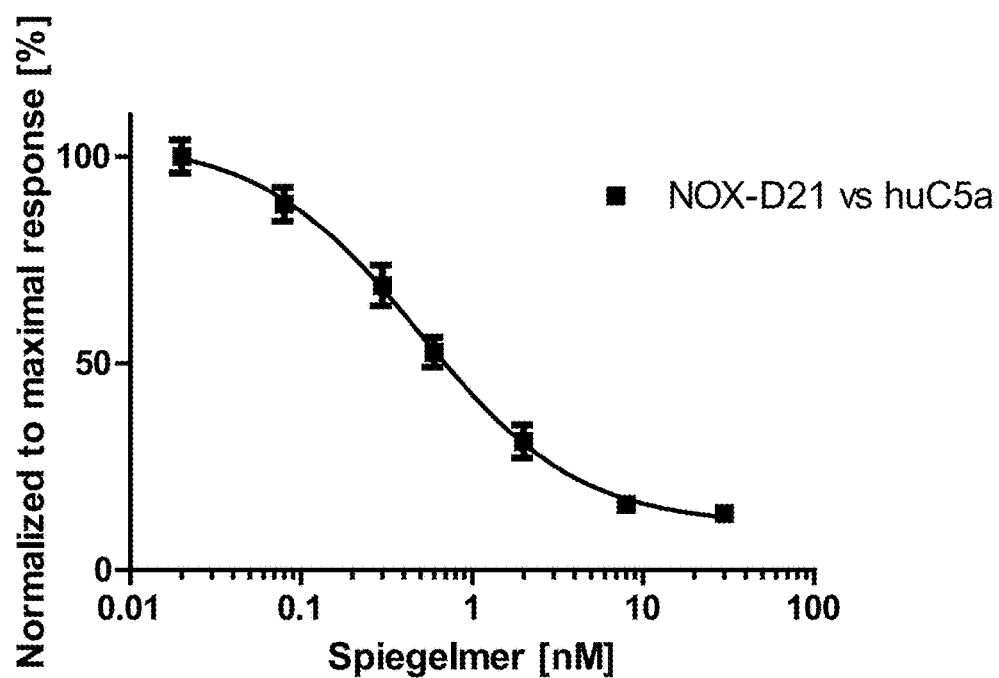
Figure 13A:
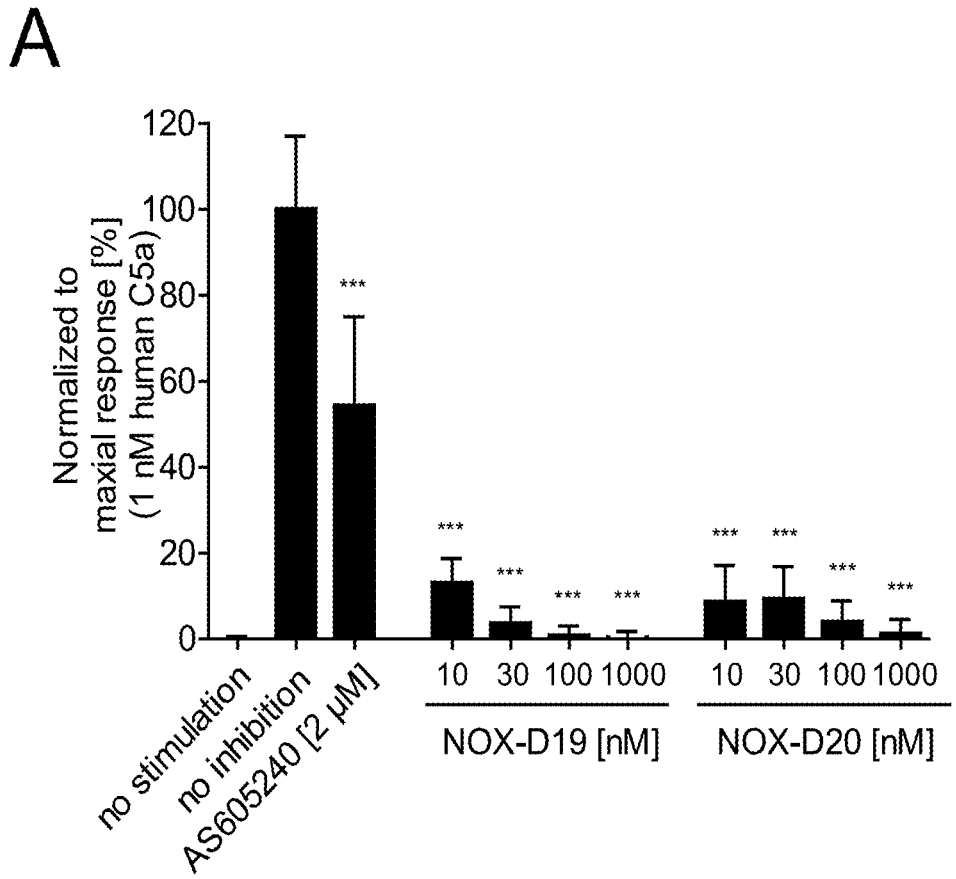
Figure 13B:
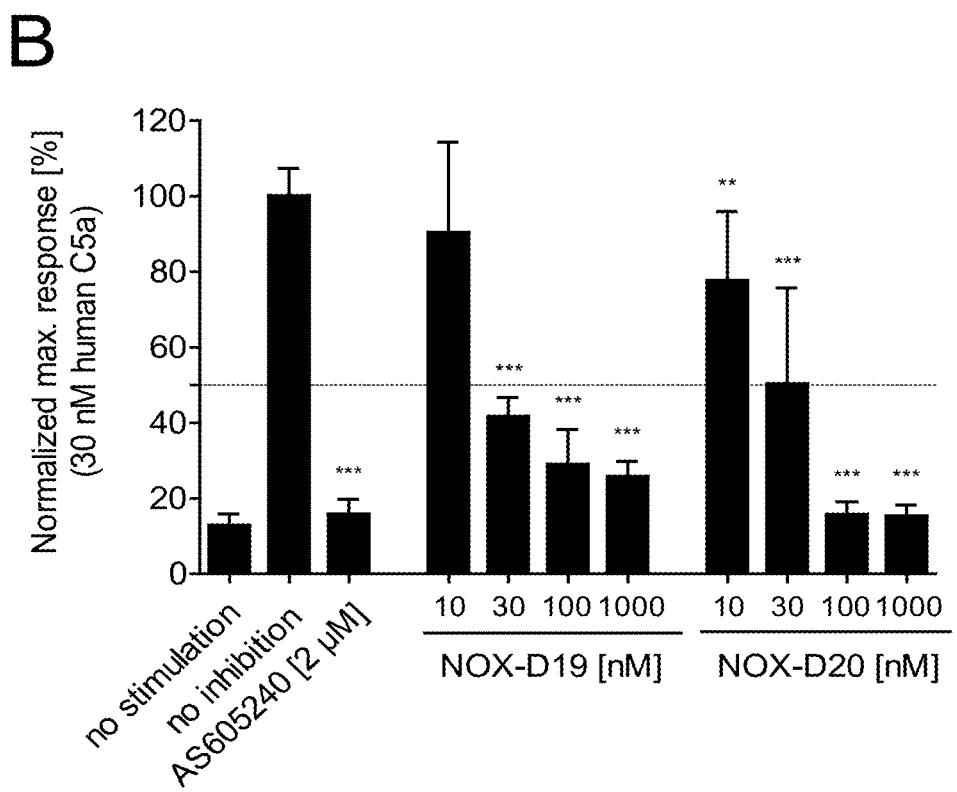
Figure 14A:
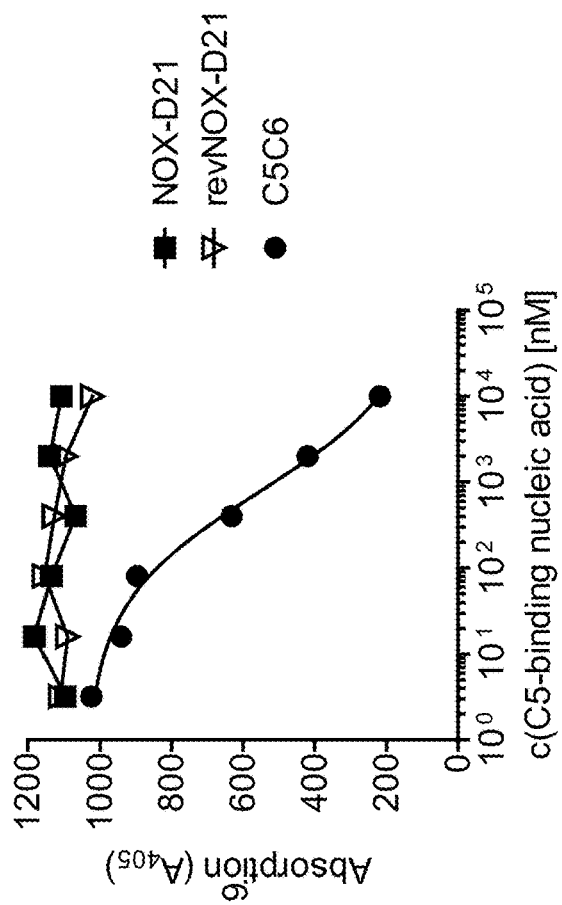
Figure 14B:
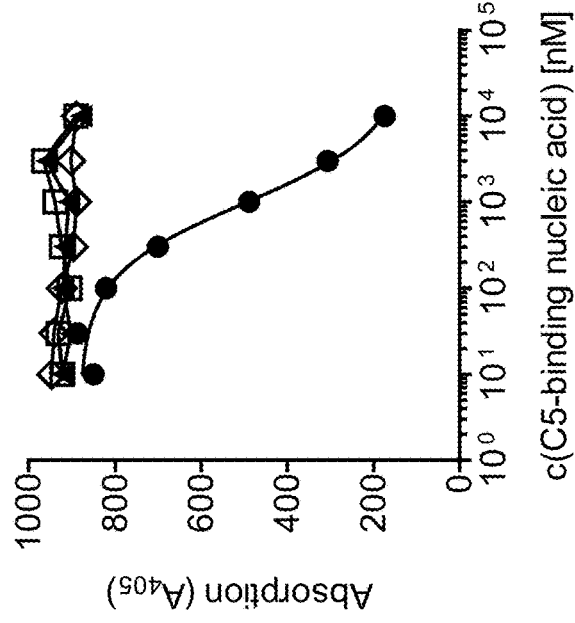
Figure 15:
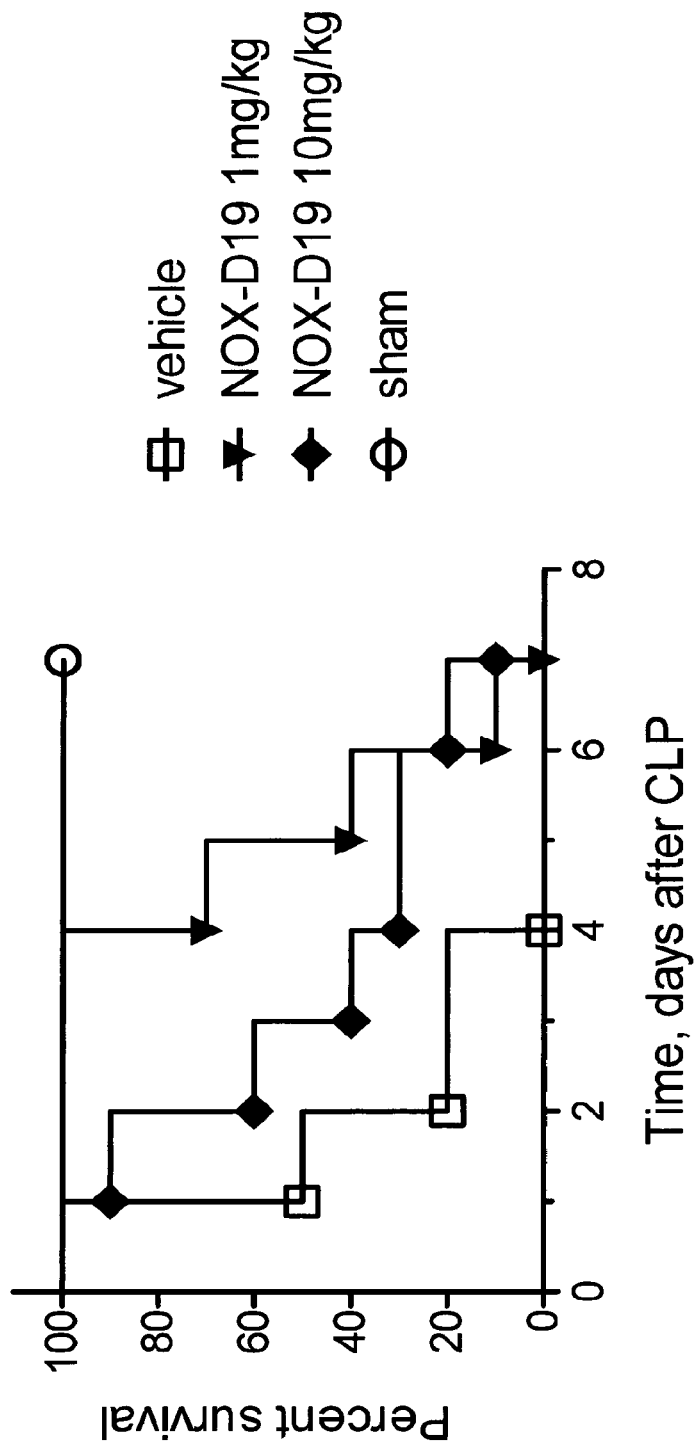
Figure 16A:
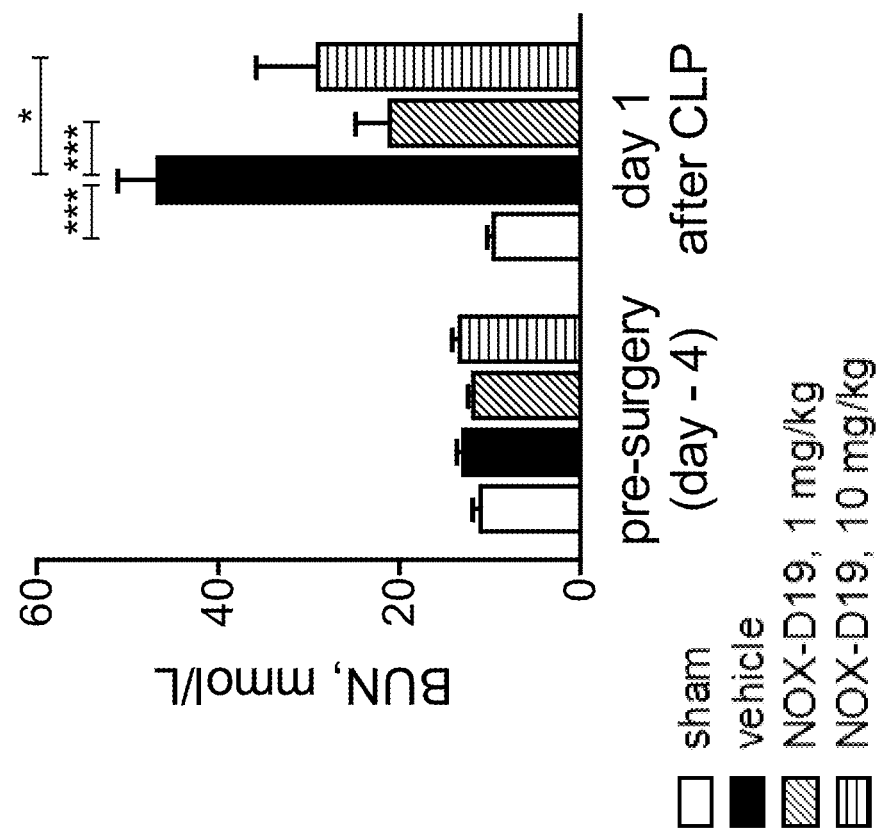
Figure 16B:
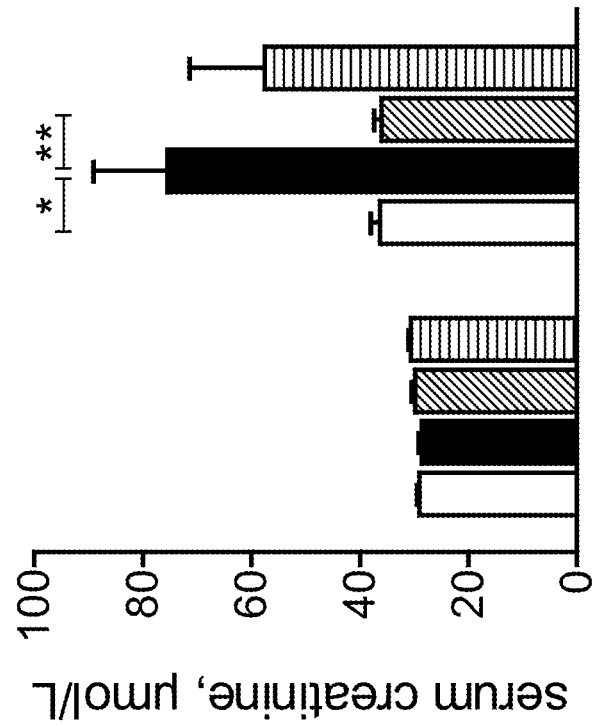
Figure 17B:
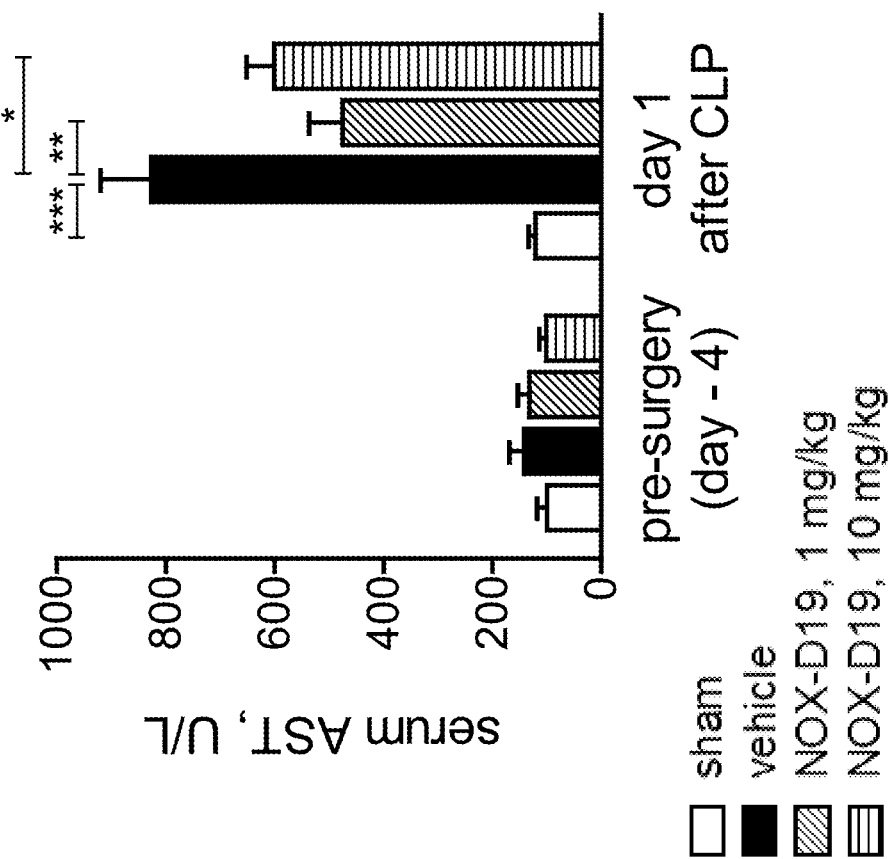
Figure 17A:
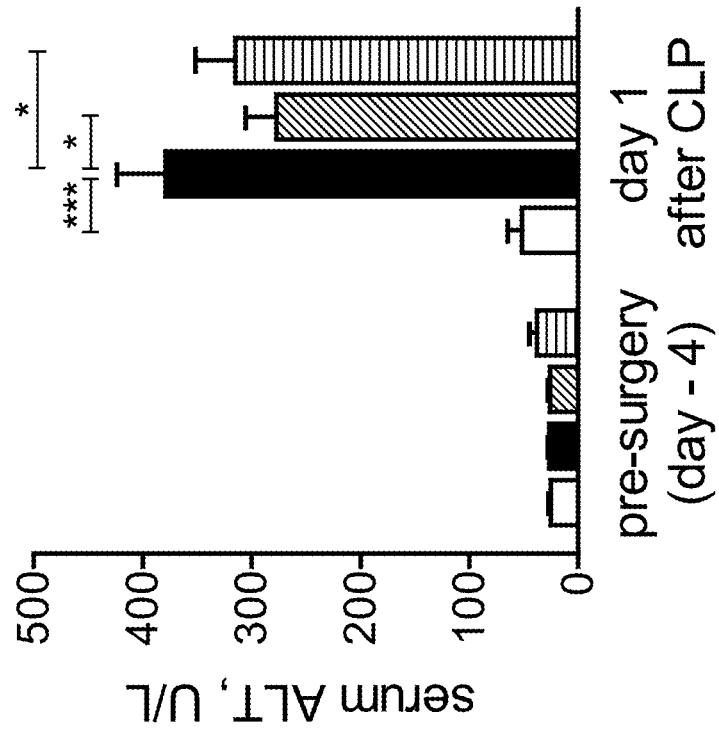
Figure 18:
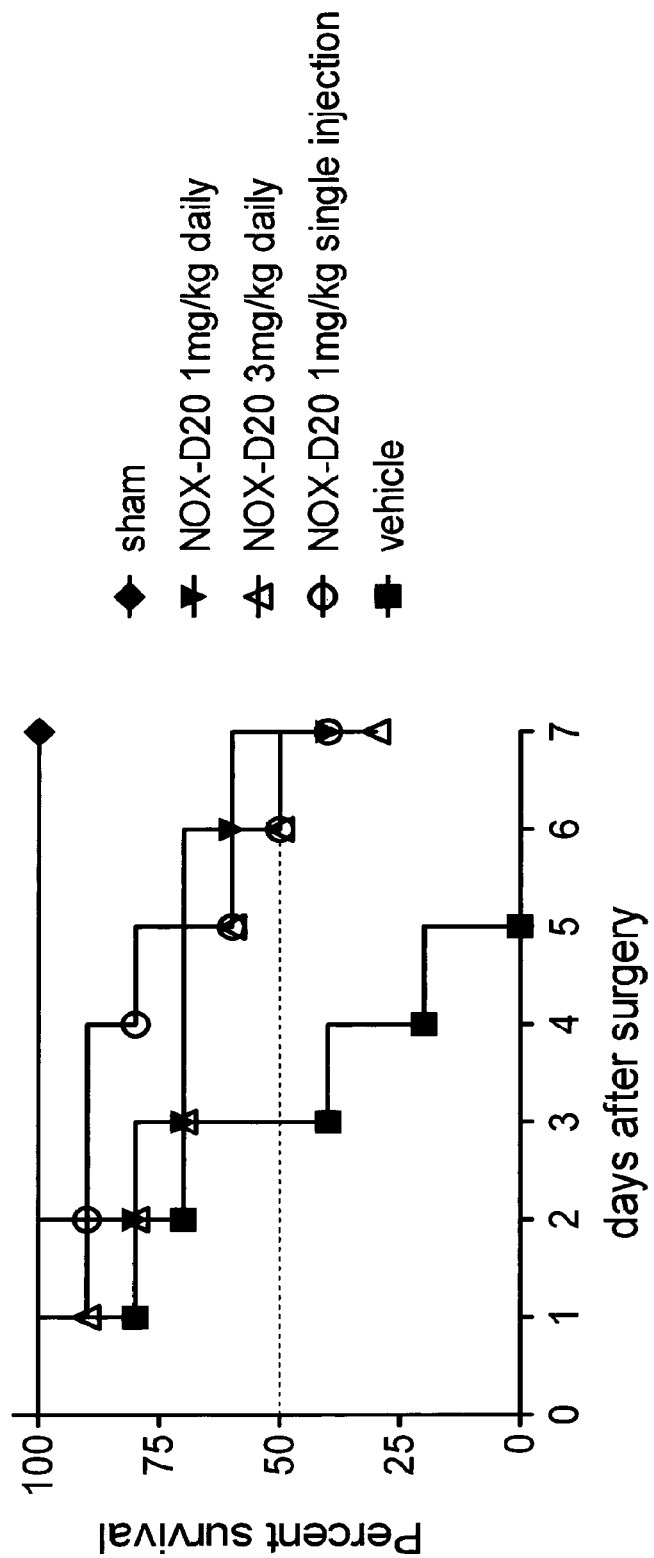

FIGS. 4 A+B show truncations of nucleic acid molecule NOX-D19001-6xDNA including the $K_D$ value and relative binding activity to human C5a as determined by surface plasmon resonance measurement;

FIG. 5 shows derivatives of nucleic acid molecule NOX-D20001 with none, one, two, three or four ribonucleotide to 2'-deoxyribonucleotide substitutions including the $K_D$ value and relative binding activity to human C5a as determined by surface plasmon resonance measurement;

FIG. 6 shows the kinetic evaluation by Biacore measurement of nucleic acid molecules NOX-D19001, NOX-D19001-D09 and NOX-D19001-D09-16-17-30-32-40 (also referred to as NOX-D19001-6×DNA) to human C5a whereby the data for 500 nM of Spiegelmer NOX-D19001, NOX-D19001-D09 (abbr. D09) and NOX-D19001-D09-16-17-30-32-40 (abbr. D09-16-17-30-32-40) are shown;

FIG. 7 is a diagram showing the efficacy of 5'-terminal 40 kDa PEGylated C5a binding Spiegelmers NOX-D19001-5'PEG (also referred as NOX-D19) NOX-D20 (also referred to as NOX-D19001-6×DNA-020-5'40 kDa PEG) in chemotaxis assays, wherein cells were allowed to migrate towards 0.1 nM huC5a preincubated at 37° C. with various amounts of Spiegelmers, FIG. 8 shows the kinetic evaluation by Biacore measurement of nucleic acid molecules NOX-D20 (also referred to as NOX-D19001-6×DNA-020-5'40 kDa PEG) to human C5a, rat C5a, mouse C5a, monkey C5a; whereby the data for 1000, 500, 250, 125, 62.5, 31.3, 15.6, 7.8, 3.9, and 1.95-0 nM of Spiegelmer NOX-D20 are shown;

FIG. 9 shows the kinetic evaluation by Biacore measurement of nucleic acid molecules NOX-D20 (also referred to as NOX-D19001-6×DNA-020-5'40 kDa PEG) to human C5, and human desArg-C5a; whereby the data for 1000, 500, 250, 125, 62.5, 31.3, 15.6, 7.8, 3.9, and 1.95-0 nM of Spiegelmer NOX-D20 are shown;

FIG. 10 shows the kinetic evaluation by Biacore measurement of nucleic acid molecules NOX-D21 (also referred to as NOX-D19001-2dU-1dC-020-5'40 kDa PEG) to human C5a, human C5, human desArg-C5a, mouse C5a and mouse desArg-C5a; whereby the data for 1000, 500, 250, 125, 62.5, 31.3, 15.6, 7.8, 3.9, and 1.95-0 nM of Spiegelmer NOX-D21 binding to human C5a and human C5 are shown;

FIG. 11 shows the polypeptide sequence alignment of C5a from human, rhesus monkey, mouse and rat;

FIG. 12A is a diagram showing the efficacy of C5a binding Spiegelmers NOX-D20 in chemotaxis assays with human C5a and mouse C5a, cells were allowed to migrate towards 0.1 nM huC5a or 0.3 nM mC5a preincubated at 37° C. with various amounts of Spiegelmer; wherein a) the cells counts were normalized to the largest value of each data set and depicted as percent count against Spiegelmer concentration, b) the Spiegelmer concentrations at which the chemotaxis is inhibited by 50% ($IC_{50}$) were calculated using nonlinear regression (four parameter fit) with Prism5 software;

FIG. 12B is a diagram showing the efficacy of C5a binding Spiegelmers NOX-D21 in chemotaxis assays with human C5a, cells were allowed to migrate towards 0.1 nM huC5a preincubated at 37° C. with various amounts of Spiegelmer; wherein a) the cells counts were normalized to the largest value of each data set and depicted as percent count against Spiegelmer concentration, b) the Spiegelmer concentrations at which the chemotaxis is inhibited by 50% (IC50) were calculated using nonlinear regression (four parameter fit) with Prism5 software;

FIGS. 13 A&B are diagrams showing the efficacy of C5a binding Spiegelmers NOX-D19 and NOX-D20 in chemotaxis assays (FIG. 13A), and elastase release assays (FIG. 13B) of primary human PMNs with human C5a; wherein cells were allowed to migrate towards 1 nM huC5a and elastase release was stimulated by 30 nM huC5a preincubated at 37° C. with various amounts of Spiegelmer;

FIGS. 14 A&B are diagrams showing evaluation of C5 cleavage inhibition using a sheep erythrocyte hemolysis assay with Spiegelmers NOX-19 and NOX-D20 (FIG. 14A), and NOX-D21 (FIG. 14B). A positive (C5C6) and negative controls (revNOX-D19 and revNOX-D21) are shown;

FIG. 15 is a diagram showing survival in the cecal ligation and puncture (CLP) mouse model of polymicrobial sepsis; NOX-D19 at the indicated doses or vehicle was injected intraperitoneally daily starting right after CLP surgery. Sham animals received surgery without CLP, followed by vehicle injections;

FIGS. 16 A&B are diagrams showing serum creatinine levels (FIG. 16A) and blood urea nitrogen (BUN) levels (FIG. 16B) pre-surgery (day −4) and 1 day after CLP surgery in mice treated with NOX-D19 at indicated doses, in vehicle treated mice and in sham animals. Serum creatinine and BUN are biomarkers for renal function;

FIGS. 17 A&B are diagrams showing serum levels of alanine aminotransferase (ALT) (FIG. 17A) and serum levels of aspartate aminotransferase (AST) (FIG. 17B) pre-surgery (day −4) and 1 day after CLP surgery in mice treated with NOX-D19 at indicated doses, in vehicle treated mice and in sham animals. Serum ALT is a biomarker for hepatocellular damage. Serum AST is a biomarker for multiorgan failure;

FIG. 18 is a diagram showing survival in the cecal ligation and puncture (CLP) mouse model of polymicrobial sepsis; NOX-D20 at the indicated doses or vehicle was injected intraperitoneally daily starting right after CLP surgery. One group received a single dose of 1 mg/kg NOX-D20 right after CLP surgery followed by daily vehicle injections. Sham animals received surgery without CLP, followed by vehicle injections.

Figures 19A, 19B, 19C:
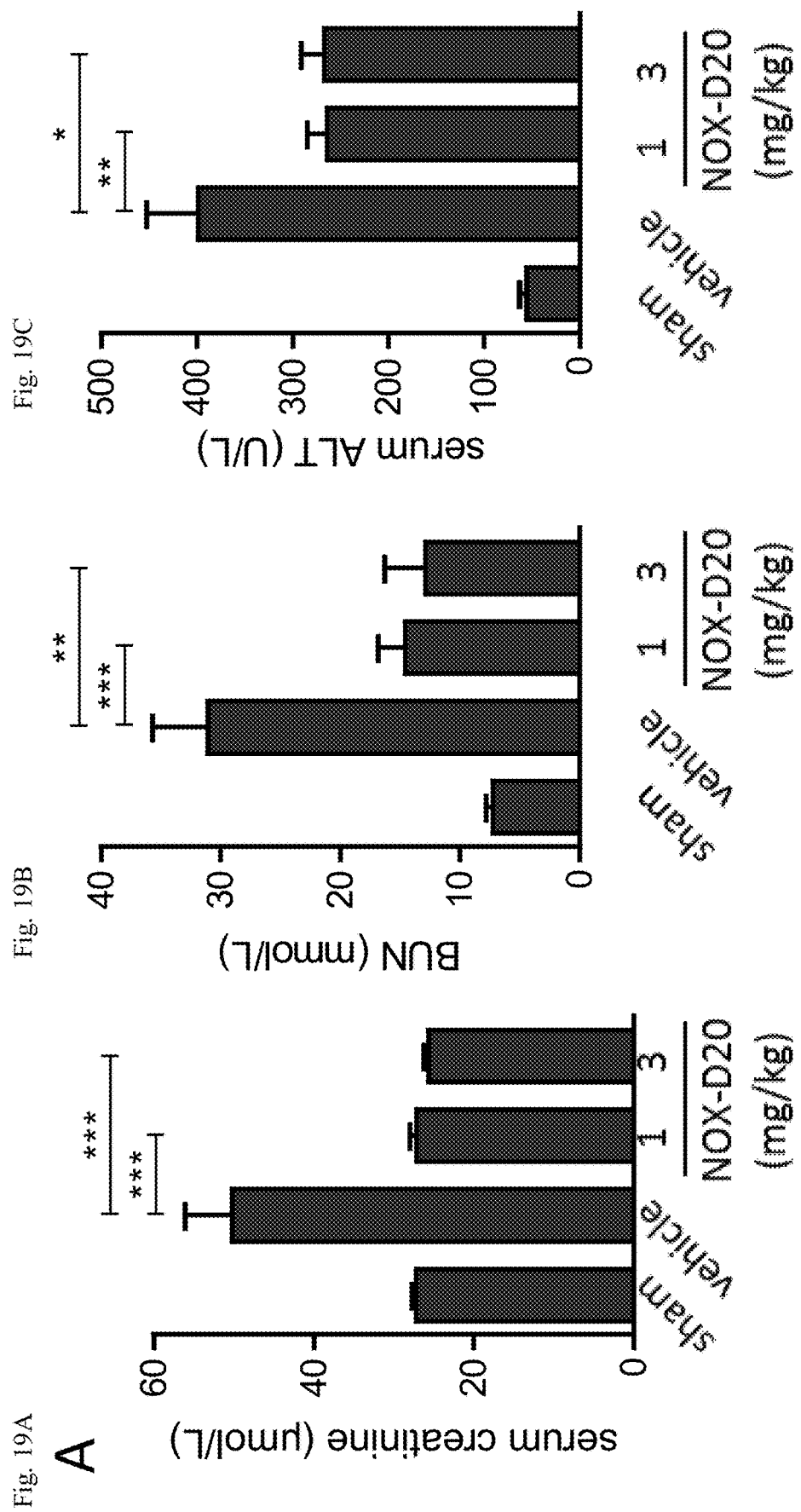
Figure 20A:
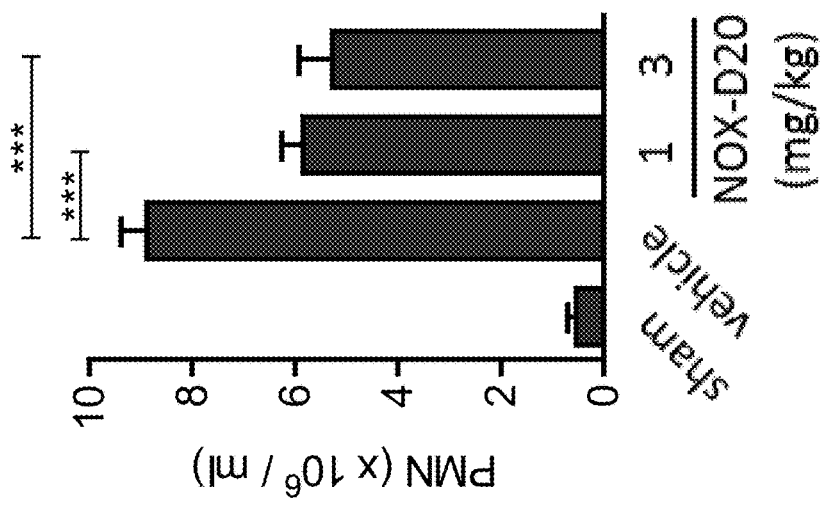
Figure 20B:
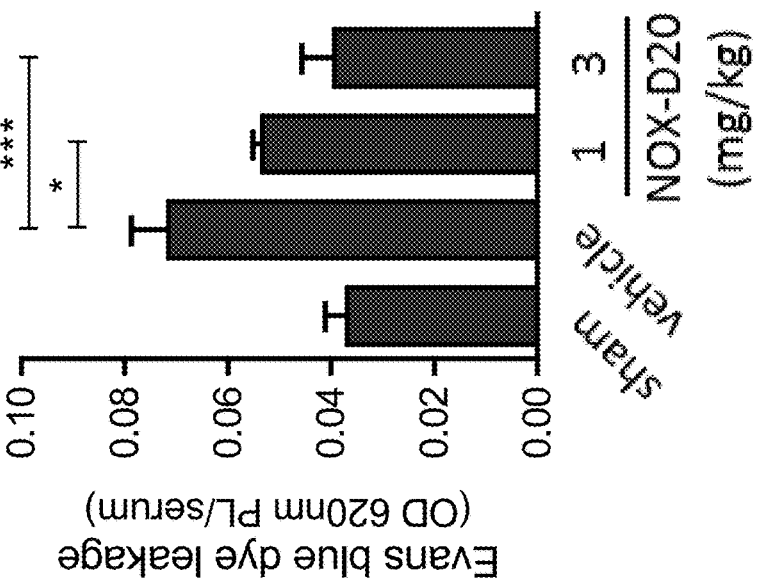
Figure 20C:
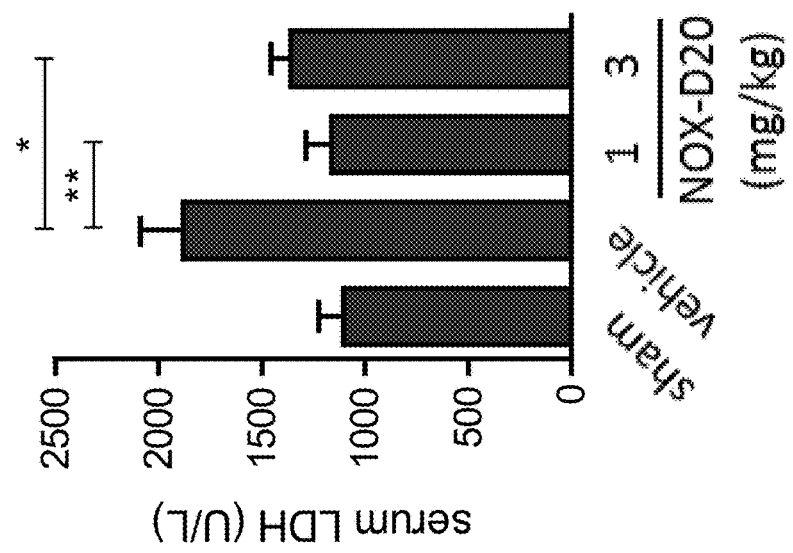
Figure 21:
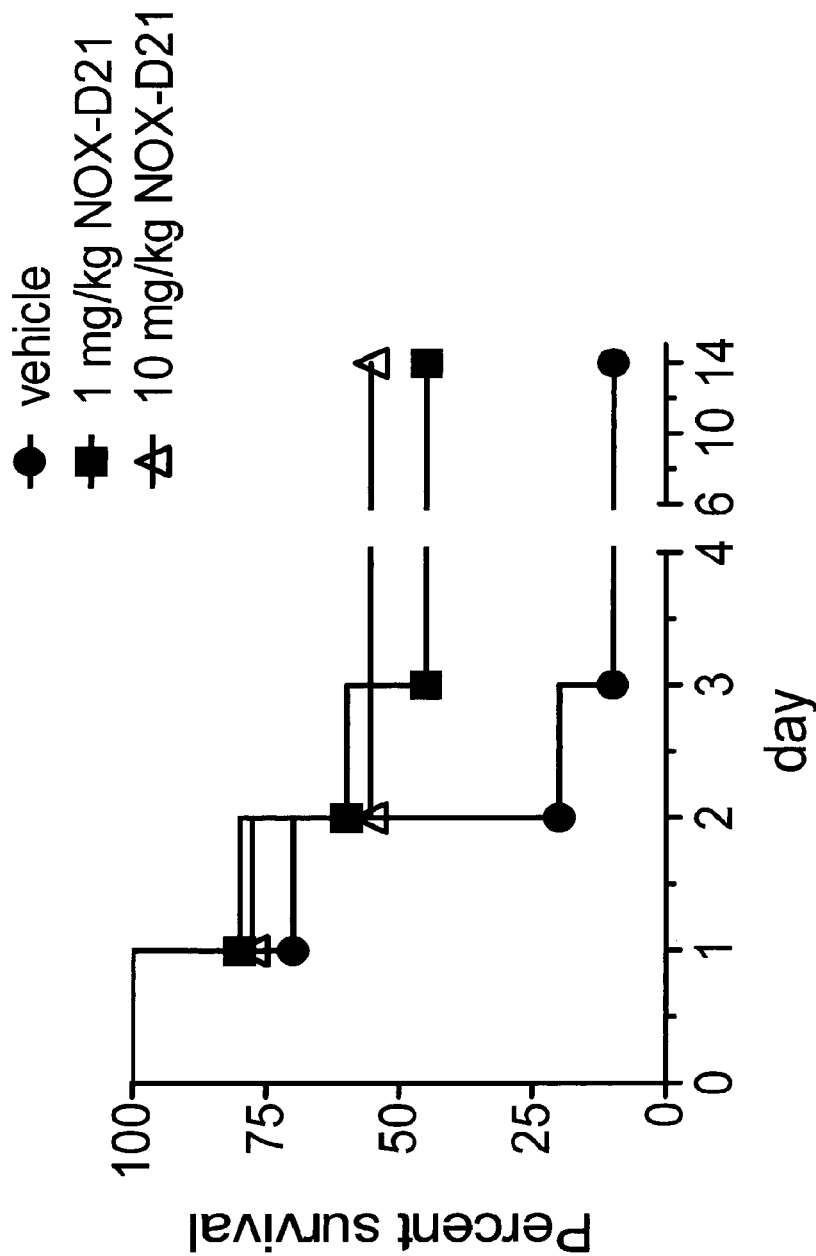
Figure 22:
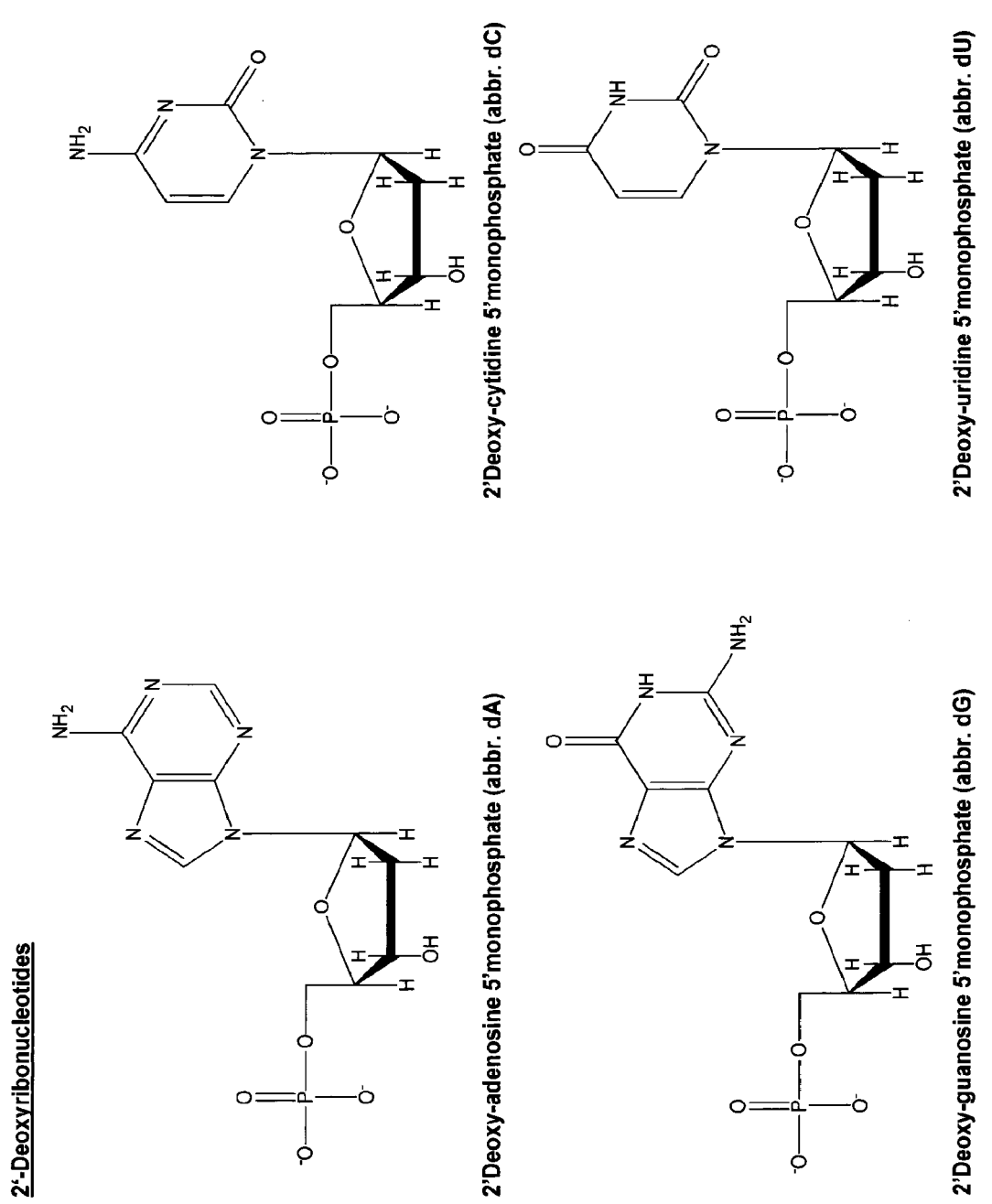
Figure 23:
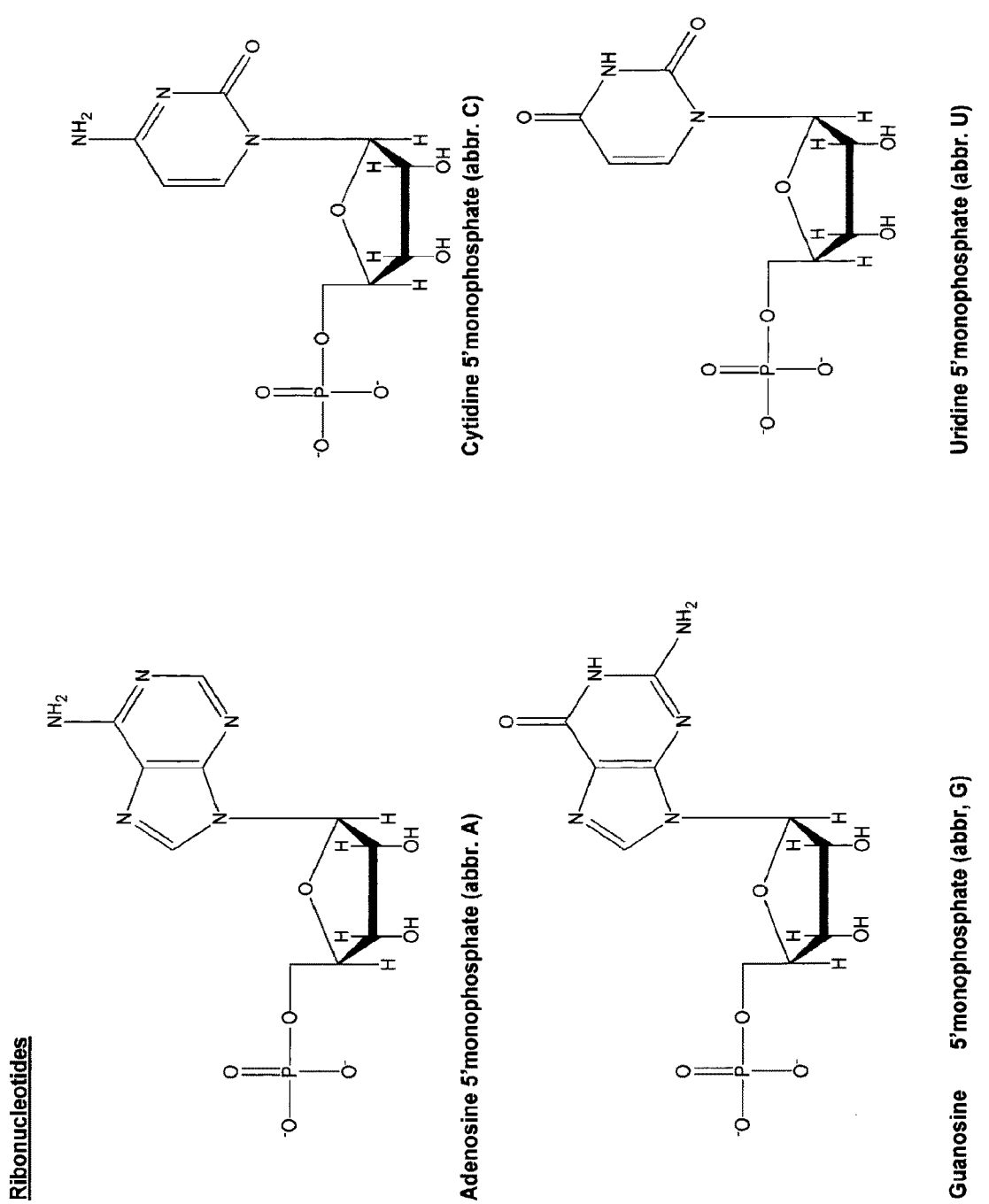

FIGS. 19A-C are diagrams showing serum creatinine levels (FIG. 19A), blood urea nitrogen (BUN) (FIG. 19B) and serum levels of alanine aminotransferase (ALT) (FIG. 19C) at day 1 after CLP surgery in mice treated with NOX-D20 at indicated doses, in vehicle treated mice and in sham animals. Serum creatinine and BUN are biomarkers for renal function. Serum ALT is a biomarker for hepatocellular damage;

FIGS. 20A-C are diagrams showing the effect of NOX-D20 treatment at indicated doses on serum lactate dehydrogenase (LDH) (FIG. 20A), a biomarker for tissue injury, vascular leakage (FIG. 20B), and PMN infiltration into the peritoneum (FIG. 20C) at day 1 after CLP surgery. Vehicle treated mice and in sham animals are shown as controls;

FIG. 21 is a diagram showing survival in a model of ischemia/reperfusion injury induced acute kidney injury; NOX-D21 at the indicated doses or vehicle was injected intravenously 1 h prior to surgery and subsequently intraperitoneally every 24 h for 3 days;

FIG. 22 shows the 2'deoxyribonucleotides that the nucleic acid molecules according to the present invention consist of;

FIG. 23 shows the ribonucleotides that the nucleic acid molecules according to the present invention consist of;

EXAMPLE 1: NUCLEIC ACID MOLECULES CAPABLE OF BINDING HUMAN AND MOUSE C5A

Several C5a binding nucleic acid molecules and derivatives thereof were identified: the nucleotide sequences of which are depicted in FIGS. 1 to 5. The C5a binding nucleic acid molecules were characterized as
   a) aptamers, i.e. D-nucleic acid molecules using a direct pull-down assay (Example 3) and/or a comparative competition pull-down assay (Example 3)
   b) Spiegelmers, i.e. L-nucleic acid molecules by surface plasmon resonance measurement (Example 4), and by an in vitro assay with cells expressing the human C5a receptor (Example 5). Moreover Spiegelmers were tested for the inhibition of C5a-induced activation of primary human neutrophils (Example 6) and in vivo (Example 8, 9 and 10). The Spiegelmers and aptamers were synthesized as described in Example 2.

The nucleic acid molecules thus generated exhibit slightly different sequences, whereby the sequences can be summarized or grouped as a sequence family.

For definition of ribonucleotide sequence motifs, the IUPAC abbreviations for ambiguous nucleotides are used:
S strong G or C;
W weak A or U;
R purine G or A;
Y pyrimidine C or U;
K keto G or U;
M imino A or C;
B not A C or U or G;
D not C A or G or U;
H not G A or C or U;
V not U A or C or G;
N all A or G or C or U If not indicated to the contrary, any nucleic acid sequence or sequence of stretches, respectively, is indicated in the 5'→3' direction.

For differentiation between the 2'-deoxyribonucleotides and the ribonucleotides the following abbreviations are used:

For 2'-deoxyribonucleotides: dG, dC, dT, dA and dU (see FIG. 22).

For ribonucleotides: G, C, T, U (see FIG. 23).

As depicted in FIG. 1 to FIG. 5 C5a binding nucleic acid molecules comprise one central stretch of nucleotides defining a potential C5a binding motif, whereby FIG. 1 shows the different sequences of the sequence family, the FIGS. 2 to 5 show derivatives of the nucleic acid molecule NOX-D19001 including NOX-D20001 (also referred to as NOX-D19001-6x-DNA-020, FIG. 4A) and NOX-D21001 (also referred to as NOX-D19001-2dU-1dC-020, FIG. 5).

In general, C5a binding nucleic acid molecules comprise at the 5'-end and the 3'-end terminal stretches of nucleotides: the first terminal stretch of nucleotides and the second terminal stretch of nucleotides. The first terminal stretch of nucleotides and the second terminal stretch of nucleotides can hybridize to each other, whereby upon hybridization a double-stranded structure is formed. However, such hybridization is not necessarily given in the molecule in vivo and in vitro.

The three stretches of nucleotides of C5a binding nucleic acid molecules—the first terminal stretch of nucleotides, the central stretch of nucleotides and the second terminal stretch of nucleotides—are arranged to each other in 5'→3'-direction: the first terminal stretch of nucleotides—the central stretch of nucleotides—the second terminal stretch of nucleotides. However, alternatively, the first terminal stretch of nucleotides, the central stretch of nucleotides and the second terminal stretch of nucleotides are arranged to each other in 5'→3'-direction: the second terminal stretch of nucleotides—the central stretch of nucleotides—the first terminal stretch of nucleotides.

The sequences of the defined stretches may be different between the C5a binding nucleic acid molecules which influences the binding affinity to C5a. Based on binding analysis of the different C5a binding nucleic acid molecules the central stretch of nucleotides and their nucleotide sequences as described in the following are individually and more preferably in their entirety essential for binding to human C5a.

The C5a binding nucleic acid molecules according to the present invention as shown in FIG. 1 consist of ribonucleotides and are shown in FIGS. 1 to 5. The C5a binding nucleic acid molecule 274-H6-002 was tested as aptamer in a comparative competition pull-down assays (for protocol see example 3) vs. C5a binding nucleic acid 274-D5-002. C5a binding nucleic acid molecule 274-H6-002 showed weaker binding affinity in comparison to C5a binding nucleic acid molecule 274-D5-002. The C5a binding nucleic acid molecules 274-B5-002, 274-D5-002, 274-C8-002, 274-C8-002-G14 (=NOX-D19001), 274-C5-002 and 274-G6-002 were tested as Spiegelmers for their ability to bind human and mouse C5a by plasmon resonance measurement (see Example 4, FIG. 1).

C5a binding nucleic acid molecule 274-C8-002-G14 (=NOX-D19001) shows the best binding affinity with a $K_D$ of 0.3 nM for mouse C5a and with a $K_D$ of 1.38 nM for human C5a (FIG. 1).

The C5a binding nucleic acid molecules 274-B5-002, 274-D5-002, 274-C8-002, 274-C8-002-G14 (=NOX-D19001), 274-C5-002, 274-G6-002 and 274-H6-002 share the sequence

[SEQ ID NO: 69]
5' AUGUGGUGKUGARGGGHUGUKGGGUGUCGACGCA 3', wherein G, A, U, C, H, K, and R are ribonucleotides.

The C5a binding nucleic acid molecules 274-C8-002, 274-C8-002-G14 (=NOX-D19001) and 274-C5-002 showed the best binding affinity to C5a and comprise the following sequences for the central stretch:

a) 274-C8-002:
[SEQ ID NO: 70]
5' AUGUGGUGUUGAAGGGUUGUUGGGUGUCGACGCA 3', b) 274-C8-002-G14:
[SEQ ID NO: 71]
5' AUGUGGUGGUGAAGGGUUGUUGGGUGUCGACGCA 3', c) 274-05-002:
[SEQ ID NO: 72]
5' AUGUGGUGGUGAGGGUUGUGGGGUGUCGACGCA 3', wherein d G, A, U and C are ribonucleotides.

The inventors surprisingly showed that the binding affinity of C5a binding nucleic acid molecule NOX-D19001 was improved by replacing ribonucleotides by 2'-deoxyribonucleotides within the sequence of the central stretch of nucleotides and the second terminal stretch of nucleotides. In particular replacing up to six ribonucleotides by 2'-deoxyribonucleotides in the C5a binding nucleic acid molecule NOX-D19001 resulted in improved binding affinity to human C5a by a factor of 3.5. In more detail, the inventors have surprisingly found that a) replacing one ribonucleotide by one 2'-deoxyribonucleotide at position 4, 11, 12, 25 or 27 in the central stretch of nucleotides of C5a binding nucleic acid molecule NOX-D19001 resulted in improved binding affinity to human C5a in comparison to the binding affinity of C5a binding nucleic acid molecule NOX-D19001 (see FIG. 2; Spiegelmers NOX-D19001-D09, NOX-D19001-D16, NOX-D19001-D17, NOX-D19001-D30, NOX-D19001-D32);

b) replacing one ribonucleotide by one 2'-deoxyribonucleotide at position 1 in the second terminal stretch of nucleotides of C5a binding nucleic acid molecule NOX-D19001 resulted in improved binding affinity to human C5a in comparison to the binding affinity of C5a binding nucleic acid molecule NOX-D19001 (see FIG. 2; Spiegelmers NOX-D19001-D40);

c) replacing two ribonucleotides by two 2'-deoxyribonucleotide at position 4/25, 4/27, or 25/27 in the central stretch of nucleotides of C5a binding nucleic acid molecule NOX-D19001 resulted in improved binding affinity to biotinylated C5a in comparison to the binding affinity of C5a binding nucleic acid molecule NOX-D19001 (see FIG. 3; Spiegelmers NOX-D19001-D09-30, NOX-D19001-D09-32, NOX-D19001-D30-32);

d) replacing two ribonucleotides, wherein one ribonucleotide was replaced by one 2'-deoxyribonucleotide at position 1 in the second terminal stretch of nucleotides of C5a binding nucleic acid molecule NOX-D19001 and one ribonucleotide was replaced by one 2'-deoxyribonucleotide at position 4, 25 or 27 in the central stretch of nucleotides of C5a binding nucleic acid molecule NOX-D19001, resulted in improved binding affinity to human C5a in comparison to the binding affinity of C5a binding nucleic acid molecule NOX-D19001 (see FIG. 3; Spiegelmers NOX-D19001-D09-40, NOX-D19001-D30-40, NOX-D19001-D32-40);

e) replacing three ribonucleotides, wherein one ribonucleotide was replaced by one 2'-deoxyribonucleotide at position 1 in the second terminal stretch of nucleotides of C5a binding nucleic acid molecule NOX-D19001 and two ribonucleotides were replaced by two 2'-deoxyribonucleotides at position 4/25, 4/27, 25/27 in the central stretch of nucleotides of C5a binding nucleic acid molecule NOX-D19001, resulted in improved binding affinity to human C5a in comparison to the binding affinity of C5a binding nucleic acid molecule NOX-D19001 (see FIG. 3; Spiegelmers, NOX-D19001-D09-30-40, NOX-D19001-D09-32-40, NOX-D19001-D30-32-40);

f) replacing three ribonucleotides by three 2'-deoxyribonucleotide at position 04/25/27 in the central stretch of nucleotides of C5a binding nucleic acid molecule NOX-D19001 resulted in improved binding affinity to biotinylated C5a in comparison to the binding affinity of C5a binding nucleic acid molecule NOX-D19001 (see FIG. 3; Spiegelmer NOX-D19001-D09-30-32);

g) replacing four ribonucleotides, wherein one ribonucleotide was replaced by one 2'-deoxyribonucleotide at position 1 in the second terminal stretch of nucleotides of C5a binding nucleic acid molecule NOX-D19001 and three ribonucleotides were replaced by three 2'-deoxyribonucleotides at position 04/25/27 in the central stretch of nucleotides of C5a binding nucleic acid molecule NOX-D19001, resulted in improved binding affinity to human C5a in comparison to the binding affinity of C5a binding nucleic acid molecule NOX-D19001 (see FIG. 3; Spiegelmer NOX-D19001-D09-30-32-40);

h) replacing five ribonucleotides, wherein one ribonucleotide was replaced by one 2'-deoxyribonucleotide at position 1 in the second terminal stretch of nucleotides of C5a binding nucleic acid molecule NOX-D19001 and four ribonucleotides were replaced by four 2'-deoxyribonucleotides at position 04/11/25/27 or 04/12/25/27 in the central stretch of nucleotides of C5a binding nucleic acid molecule NOX-D19001, resulted in improved binding affinity to human C5a in comparison to the binding affinity of C5a binding nucleic acid molecule NOX-D19001 (see FIG. 3; Spiegelmer NOX-D19001-D09-16-30-32-40, NOX-D19001-D09-17-30-32-40);

i) replacing six ribonucleotides, wherein one ribonucleotide was replaced by one 2'-deoxyribonucleotide at position 1 in the second terminal stretch of nucleotides of C5a binding nucleic acid molecule NOX-D19001 and five ribonucleotides were replaced by five 2'-deoxyribonucleotides at position 04/11/12/25/27 in the central stretch of nucleotides of C5a binding nucleic acid molecule NOX-D19001, resulted in improved binding affinity to human C5a in comparison to the binding affinity of C5a binding nucleic acid molecule NOX-D19001 (see FIG. 3; Spiegelmer NOX-D19001-D09-16-17-30-32-40=NOX-D19-001-6×DNA).

Based on the data shown that replacing ribonucleotides by 2'-deoxyribonucleotides at several positions of the central stretch of nucleotides of C5a binding nucleic acid molecules lead to improved binding to C5a the central stretch of all tested C5a binding nucleic acid molecules can be summarized in a the following formula 5'
AUGn$_1$GGUGKUn$_2$n$_3$RGGGHUGUKGGGn$_4$Gn$_5$CGACGCA 3' [SEQ ID NO: 61], wherein n$_1$ is U or dU, n$_2$ is G or dG, n$_3$ is A or dA, n$_4$ is U or dU, n$_5$ is U or dU and G, A, U, C, H, K, and R are ribonucleotides, and dU, dG and dA are 2'-deoxyribonucleotides, wherein
  a) in a preferred embodiment the central stretch of nucleotides comprise the sequence 5' AUGn$_1$GGUGUUn$_2$n$_3$AGGGUUGUGGGGn$_4$Gn$_5$CGACGCA 3' [SEQ ID NO: 62](see 274-B5-002); or
  b) in a preferred embodiment the central stretch of nucleotides comprise the sequence 5' AUGn$_1$GGUGUUn$_2$n$_3$GGGGUUGUGGGGn$_4$Gn$_5$CGACGCA 3' [SEQ ID NO: 63](see 274-D5-002); or
  c) in a preferred embodiment the central stretch of nucleotides comprise the sequence 5' AUGn$_1$GGUGUUn$_2$n$_3$AGGGUUGUUGGGn$_4$Gn$_5$CGACGCA 3' [SEQ ID NO: 64](see 274-C8-002); or
  d) in a preferred embodiment the central stretch of nucleotides comprise the sequence 5' AUGn$_1$GGUGGUn$_2$n$_3$AGGGUUGUUGGGn$_4$Gn$_5$CGACGCA 3' [SEQ ID NO: 65](see NOX-D19001); or
  e) in a preferred embodiment the central stretch of nucleotides comprise the sequence 5' AUGn$_1$GGUGGUn$_2$n$_3$GGGGUUGUGGGGn$_4$Gn$_5$CGACGCA 3' [SEQ ID NO: 66](see 274-C5-002); or
  f) in a preferred embodiment the central stretch of nucleotides comprise the sequence 5' AUGn$_1$GGUGGUn$_2$n$_3$GGGGAUGUGGGGn$_4$Gn$_5$CGACGCA 3' [SEQ ID NO: 67](see 274-G6-002); or
  g) in a preferred embodiment the central stretch of nucleotides comprise the sequence 5' AUGn$_1$GGUGUUn$_2$n$_3$GGGGCUGUGGGGn$_4$Gn$_5$CGACGCA 3' [SEQ ID NO: 68] (see 274-H6-002).

The C5a binding nucleic acid molecules NOX-D19001-D09, NOX-D19001-D16, NOX-D19001-D17, NOX-D19001-D30, NOX-D19001-D32, NOX-D19001-D09-30, NOX-D19001-D09-32, NOX-D19001-D09-40, NOX-D19001-D30-32, NOX-D19001-D30-40, NOX-D19001-D32-40, NOX-D19001-D09-30-32, NOX-D19001-D09-30-

40, NOX-D19001-D09-32-40, NOX-D19001-D30-32-40, NOX-D19001-D09-30-32-40, NOX-D19001-D09-16-30-32-40, NOX-D19001-D09-17-30-32-40, NOX-D19001-D09-16-17-30-32-40 (see FIGS. 2 and 3) showed the best binding affinity to C5a and comprise the following sequence for the central stretch of nucleotides:

a) 5' AUGdUGGUGGUGAAGGGUUGUUGGGUGUCGACGCA 3' [SEQ ID NO: 73]
(see NOX-D19001-D09, NOX-D19001-D09-40); or b) 5' AUGUGGUGGUdGAAGGGUUGUUGGGUGUCGACGCA 3' [SEQ ID NO: 74]
(see NOX-D19001-D16); or c) 5' AUGUGGUGGUGdAAGGGUUGUUGGGUGUCGACGCA 3' [SEQ ID NO: 75]
(see NOX-D19001-D17); or d) 5' AUGUGGUGGUGAAGGGUUGUUGGGdUGUCGACGCA 3' [SEQ ID NO: 76]
(see NOX-D19001-D30, NOX-D19001-D30-40); or e) 5' AUGUGGUGGUGAAGGGUUGUUGGGUGdUCGACGCA 3' [SEQ ID NO: 77]
(see NOX-D19001-D32, NOX-D19001-D32-40); or f) 5' AUGdUGGUGGUGAAGGGUUGUUGGGdUGUCGACGCA 3' [SEQ ID NO: 78]
(see NOX-D19001-D09-30, NOX-D19001-D09-30-40); or g) 5' AUGdUGGUGGUGAAGGGUUGUUGGGUGdUCGACGCA 3' [SEQ ID NO: 79]
(see NOX-D19001-D09-32, NOX-D19001-D09-32-40);

h) 5' AUGUGGUGGUGAAGGGUUGUUGGGdUGdUCGACGCA 3' [SEQ ID NO: 80]
(see NOX-D19001-D30-32, NOX-D19001-D30-32-40); or i) 5' AUGdUGGUGGUGAAGGGUUGUUGGGdUGdUCGACGCA 3' [SEQ ID NO: 81]
(NOX-D19001-D09-30-32, NOX-D19001-D09-30-32-40); or j) 5' AUGdUGGUGGUdGAAGGGUUGUUGGGdUGdUCGACGCA 3' [SEQ ID NO: 82]
(see NOX-D19001-D09-16-30-32-40); or k) AUGdUGGUGGUGdAAGGGUUGUUGGGdUGdUCGACGCA 3' [SEQ ID NO: 83]
(see NOX-D19001-D09-17-30-32-40); or l) 5' AUGdUGGUGGUdGdAAGGGUUGUUGGGdUGdUCGACGCA 3' [SEQ ID NO: 84]
(see NOX-D19001-D09-16-17-30-32-40 = NOX-D19001-6xDNA), wherein G, A, U and C are ribonucleotides, and dG, dA and dU are 2'-deoxyribonucleotides.

The binding affinity of C5a binding nucleic acid molecule NOX-D19001 was significantly improved by replacing one up to six ribonucleotides by 2'-deoxyribonucleotides as determined by surface plasmon resonance measurement and exemplarily shown for the C5a binding nucleic acids NOX-D19001-D09 and NOX-D19001-D09-16-17-30-32-40 (also referred to as NOX-D19001-6xDNA) (FIG. 6):

NOX-D19001: $K_D$ of 1.38 nM,
NOX-D19001-D09: $K_D$ of 709 pM,
NOX-D19001-D09-16-17-30-32-40: $K_D$ of 361 pM.

NOX-D19001-6xDNA comprises a central stretch of nucleotides with five 2'-deoxyribonucleotides instead of ribonucleotides, a first terminal stretch of nucleotides with five ribonucleotides and a second terminal stretch of nucleotides with four ribonucleotides and one 2'-deoxyribonucleotide. Surprisingly, the inventors could show that the first and the second terminal stretch of nucleotides can be truncated without reduction in affinity to four or three nucleotides.

As shown herein, the first and the second terminal stretch of nucleotides of NOX-D19001-6xDNA could be truncated from five to three nucleotides (see NOX-D19001-6xDNA-020 also referred to as NOX-D20001) while retaining affinity (FIG. 4A).

FIG. 4 demonstrates the successful combination of ribonucleotide-to-2'-deoxyribonucleotide substitution and truncation: The mother molecule of NOX-D19001-6xDNA and NOX-D19001-6xDNA-020 (also referred to as NOX-D20001), NOX-D19001, consisting of ribonucleotides and a first and a second terminal stretch of nucleotides with five nucleotides each has a binding affinity ($K_D$) of 1.38 nM. After six ribonucleotide-to-2'-deoxyribonucleotide substitutions (leading to NOX-D19001-6xDNA) and truncation to a first and a second terminal stretch of nucleotides with three nucleotides (leading to NOX-D19001-6xDNA-020, also referred to as NOX-D20001) the binding affinity for human C5a was improved by a more than factor four (NOX-D20001, $K_D$ of 0.3 nM). Truncation of the first or the second stretch of nucleotides to one nucleotide led to reduced activity, but such molecules still bind to C5a with $K_D$'s lower than 10 nM (see FIG. 4A, 4B) Another example for the successful substitution of ribonucleotides by 2'-deoxyribonucleotides is shown in FIG. 5. Molecule NOX-D19001-020 is a truncated derivative of NOX-D19001 and has a $K_D$ of 11.3 nM (see FIG. 5) instead of 1.38 nM as determined for NOX-D19001 (see FIGS. 1 and 2). Both molecules comprise the identical central stretch of ribonucleotides, but NOX-D19001-020 comprises of a first terminal stretch of only three instead of five ribonucleotides and a second terminal stretch of only three instead of five ribonucleotides. By substitution of two or three ribonucleotides by 2'-deoxyribonucleotides in the central stretch of nucleotides and optionally of one ribonucleotide by 2'-deoxyribonucleotide in the second terminal stretch of nucleotides the binding affinity of NOX-D19001-020 can be improved by a factor of more than 10 (see FIG. 5, NOX-D19001-2xDNA-020, NOX-D19001-3xDNA-020, NOX-D19001-2dU-1dC-020 also referred to as NOX-D21001, NOX-D19001-3dU-1dC-020).

Taken together, the first and the second terminal stretches of C5a binding nucleic acid molecules comprise one, two, three, four or five nucleotides (FIG. 1 to FIG. 5), whereby the stretches optionally hybridize with each other, whereby upon hybridization a double-stranded structure is formed. This double-stranded structure can consist of one to five basepairs. However, such hybridization is not necessarily given in the molecule.

Analyzing the first terminal stretch of nucleotides and the second terminal stretch of nucleotides of all tested C5a binding nucleic acid molecules the generic formula for the first terminal stretch of nucleotides is 5' $Z_1Z_2Z_3Z_4G$ 3' and the generic formula for the second terminal stretch of nucleotides is 5' $Z_5Z_6Z_7Z_8\ Z_9$ 3', wherein
$Z_1$ is G or absent, $Z_2$ is S or absent, $Z_3$ is S or absent, $Z_4$ is B or absent, $Z_5$ is C or dC, $Z_6$ is V or absent, $Z_7$ is S or absent, $Z_8$ is S or absent, $Z_9$ is C or absent, and
G, S, B, C, V are ribonucleotides, and dC is a 2'-deoxyribonucleotide, whereby in a first preferred embodiment
a) $Z_1$ is G, $Z_2$ is S, $Z_3$ is S, $Z_4$ is B, $Z_5$ is C or dC, $Z_6$ is V, $Z_7$ is S, $Z_8$ is S, $Z_9$ is C, or
b) $Z_1$ is absent, $Z_2$ is S, $Z_3$ is S, $Z_4$ is B, $Z_5$ is C or dC, $Z_6$ is V, $Z_7$ is S, $Z_8$ is S, $Z_9$ is absent, or
c) $Z_1$ is absent, $Z_2$ is absent, $Z_3$ is S, $Z_4$ is B, $Z_5$ is C or dC, $Z_6$ is V, $Z_7$ is S, $Z_8$ is absent, $Z_9$ is absent, or d) $Z_1$ is absent, $Z_2$ is absent, $Z_3$ is absent, $Z_4$ is B, $Z_5$ is C or dC, $Z_6$ is V, $Z_7$ is absent, $Z_8$ is absent, $Z_9$ is absent, or e) $Z_1$ is absent, $Z_2$ is S, $Z_3$ is S, $Z_4$ is B, $Z_5$ is C or dC, $Z_6$ is V, $Z_7$ is S, $Z_8$ is S, $Z_9$ is C, or f) $Z_1$ is absent, $Z_2$ is absent, $Z_3$ is S, $Z_4$ is B, $Z_5$ is C or dC, $Z_6$ is V, $Z_7$ is S, $Z_8$ is S, $Z_9$ is C, or g) $Z_1$ is absent, $Z_2$ is absent, $Z_3$ is absent, $Z_4$ is B, $Z_5$ is C or dC, $Z_6$ is V, $Z_7$ is S, $Z_8$ is S, $Z_9$ is C, or h) $Z_1$ is absent, $Z_2$ is absent, $Z_3$ is absent, $Z_4$ is absent, $Z_5$ is C or dC, $Z_6$ is V, $Z_7$ is S, $Z_8$ is S, $Z_9$ is C, or i) $Z_1$ is absent, $Z_2$ is absent, $Z_3$ is S, $Z_4$ is B, $Z_5$ is C or dC, $Z_6$ is V, $Z_7$ is S, $Z_8$ is S, $Z_9$ is absent, or j) $Z_1$ is absent, $Z_2$ is absent, $Z_3$ is absent, $Z_4$ is B, $Z_5$ is C or dC, $Z_6$ is V, $Z_7$ is S, $Z_8$ is S, $Z_9$ is absent, or k) $Z_1$ is absent, $Z_2$ is absent, $Z_3$ is absent, $Z_4$ is absent, $Z_5$ is C or dC, $Z_6$ is V, $Z_7$ is S, $Z_8$ is S, $Z_9$ is absent, or l) $Z_1$ is absent, $Z_2$ is S, $Z_3$ is S, $Z_4$ is B, $Z_5$ is C or dC, $Z_6$ is V, $Z_7$ is S, $Z_8$ is absent, $Z_9$ is absent, or m) $Z_1$ is absent, $Z_2$ is S, $Z_3$ is S, $Z_4$ is B, $Z_5$ is C or dC, $Z_6$ is V, $Z_7$ is absent, $Z_8$ is absent, $Z_9$ is absent, or n) $Z_1$ is absent, $Z_2$ is absent, $Z_3$ is absent, $Z_4$ is absent, $Z_5$ is C, $Z_6$ is V, $Z_7$ is S, $Z_8$ is absent, $Z_9$ is absent, or o) $Z_1$ is absent, $Z_2$ is absent, $Z_3$ is absent, $Z_4$ is B, $Z_5$ is C or dC, $Z_6$ is V, $Z_7$ is S, $Z_8$ is absent, $Z_9$ is absent, or p) $Z_1$ is absent, $Z_2$ is absent, $Z_3$ is S, $Z_4$ is B, $Z_5$ is C or dC, $Z_6$ is V, $Z_7$ is absent, $Z_8$ is absent, $Z_9$ is absent, or q) $Z_1$ is absent, $Z_2$ is absent, $Z_3$ is S, $Z_4$ is B, $Z_5$ is C or dC, $Z_6$ is absent, $Z_7$ is absent, $Z_8$ is absent, $Z_9$ is absent;

in a second preferred embodiment a) the first terminal stretch of nucleotides comprises a nucleotide sequence of 5' GCCUG 3' and the second terminal stretch of nucleotides comprises a nucleotide sequence 5' CAGGC, or b) the first terminal stretch of nucleotides comprises a nucleotide sequence of 5' GCCUG 3' and the second terminal stretch of nucleotides comprises a nucleotide sequence of 5' dCAGGC 3', or c) the first terminal stretch of nucleotides comprises a nucleotide sequence of 5' CCUG 3' or 5' CUG 3' or 5' UG 3' or 5' G 3', and the second terminal stretch of nucleotides comprises a nucleotide sequence of 5' dCAGGC 3', or d) the first terminal stretch of nucleotides comprises a nucleotide sequence of 5' GCUG 3' and the second terminal stretch of nucleotides comprises a nucleotide sequence of 5' dCAGC 3', or e) the first terminal stretch of nucleotides comprises a nucleotide sequence of 5' GCCG 3' and the second terminal stretch of nucleotides comprises a nucleotide sequence of 5' dCGGC 3', or f) the first terminal stretch of nucleotides comprises a nucleotide sequence of 5' GGCG 3' and the second terminal stretch of nucleotides comprises a nucleotide sequence of 5' dCGCC 3', or g) the first terminal stretch of nucleotides comprises a nucleotide sequence of 5' CUG 3' or 5' UG 3' or 5' CG 3' or 5' G 3', and the second terminal stretch of nucleotides comprises a nucleotide sequence of 5' dCAGC 3', or h) the first terminal stretch of nucleotides comprises a nucleotide sequence of 5' GCUG 3' and the second terminal stretch of nucleotides comprises a nucleotide sequence of 5' dCAC 3' or 5' dCC 3' or 5' dCA 3', or i) the first terminal stretch of nucleotides comprises a nucleotide sequence of 5' GUG 3' and the second terminal stretch of nucleotides comprises a nucleotide sequence of 5' dCAC 3', or j) the first terminal stretch of nucleotides comprises a nucleotide sequence of 5' UG 3' and the second terminal stretch of nucleotides comprises a nucleotide sequence of 5' dCA 3', or k) the first terminal stretch of nucleotides comprises a nucleotide sequence of 5' GCG 3' and the second terminal stretch of nucleotides comprises a nucleotide sequence of 5' dCGC 3', or l) the first terminal stretch of nucleotides comprises a nucleotide sequence of 5' CG 3' and the second terminal stretch of nucleotides comprises a nucleotide sequence of 5' dCGC 3', or m) the first terminal stretch of nucleotides comprises a nucleotide sequence of 5' G 3' and the second terminal stretch of nucleotides comprises a nucleotide sequence of 5' dCGC 3', or n) the first terminal stretch of nucleotides comprises a nucleotide sequence of 5' GCG 3' and the second terminal stretch of nucleotides comprises a nucleotide sequence of 5' dCC 3', or o) the first terminal stretch of nucleotides comprises a nucleotide sequence of 5' GCG 3' and the second terminal stretch of nucleotides comprises a nucleotide sequence of 5' dC 3', or p) the first terminal stretch of nucleotides comprises a nucleotide sequence of 5' GG 3' and the second terminal stretch of nucleotides comprises a nucleotide sequence of 5' dCC 3', or q) the first terminal stretch of nucleotides comprises a nucleotide sequence of 5' GCG 3' and the second terminal stretch of nucleotides comprises a nucleotide sequence of 5' CGC 3'.

In order to prove their functionality, the C5a binding nucleic acid molecules NOX-D19001, NOX-D20001 and NOX-D21001 were synthesized as a Spiegelmer comprising an amino-group at its 5'-end. To said amino-modified Spiegelmers a 40 kDa PEG-moiety was coupled leading to C5a binding Spiegelmers NOX-D19, NOX-D20 and NOX-D21. Synthesis and PEGylation of the Spiegelmer is described in Example 2.

The effect of improved binding affinity could be shown for the functionality of C5a binding nucleic acid molecules. As determined by a chemotaxis assay (Example 5), the C5a binding nucleic acid molecule NOX-D19 ($IC_{50}=1.9$ nM) exclusively consisting of ribonucleotides was less potent to inhibit the function of human C5a than the NOX-D20, a derivative C5a binding nucleic acid molecule of NOX-D19 comprising six ribonucleotide-to-2'-deoxyribonucleotide substitutions ($IC_{50}=0.28$ nM) (FIG. 7).

NOX-D20 showed a very high affinity binding to murine C5a with a dissociation constant $K_D$ of 19 pM, whereas for human C5a a $K_D$ of 299 pM was determined (Example 4, FIG. 8). NOX-D20 inhibits the function of human C5a with an inhibitory constant $IC_{50}$ of 275 pM as determined by a chemotaxis assay (Example 5, FIGS. 7 and 12 A). For stoichiometric reasons, the sensitivity of the chemotaxis assays for mouse C5a is limited to 150 pM due a stimulatory concentration of mouse C5a of 300 pM. Accordingly, for mouse C5a an $IC_{50}$ of 140 pM was measured for NOX-D20 (Example 5, FIG. 12 A).

NOX-D20 showed no binding to C5a from rat or rhesus monkey, indicating very high target specificity (FIG. 8). From the polypeptide sequence alignment of human, mouse, rat and rhesus monkey C5a and the determined specificity it is most likely that the residues Serine16 and Valine28 of human C5a are essential binding residues on C5a (FIG. 11). These are conserved in human and murine C5a but are different in rhesus monkey and rat C5a.

NOX-D21 contains the major affinity-improving sites of NOX-D20 and showed a high affinity to human and murine C5a as shown by Biacore measurement ($K_D$(murine C5a) =29 pM, $K_D$(human C5a)=815 pM, $K_D$(human C5)=413 pM, see FIG. 11). NOX-D21 inhibits the function of human C5a with an inhibitory constant $IC_{50}$ of 476 pM, as determined by a chemotaxis assay (Example 5, FIG. 12B).

In vivo a truncated version of C5a is generated by enzymatic cleavage of the C-terminal arginine residue, known as des-Arg-C5a (also referred to as $C5a_{des\text{-}Arg}$). The biological function of des-Arg-C5a is not fully understood but there is evidence that des-Arg-C5a retains leukocyte activating functions. Therefore it was investigated, whether NOX-D20 also bound to des-Arg-C5a. NOX-D20 showed a dose-dependent binding to immobilized recombinant human des-Arg-C5a (FIG. 9).

Detailed kinetic evaluation as described showed that human des-Arg-C5a is bound by NOX-20 with comparable affinity to the full-length human C5a with a dissociation constant of 316 pM and 299 pM, respectively. NOX-D21 bound to mouse and human des-Arg-C5a with dissociation constants of 28 pM and 854 pM, respectively (FIG. 10). Thus even after cleavage of C5a to des-Arg-C5a C5a binding nucleic acid molecules such as NOX-20 and NOX-D21 still bind to their target.

Surprisingly NOX-D20 and NOX-D21 also showed binding to C5 purified from human plasma with an affinity of 164 pM and 413 pM, respectively (FIGS. 9 and 10). This phenomenon could not be foreseen. However, it is plausible since C5a is a part of C5 that is cleaved off by the C5 convertase when the complement system is activated or by thrombin or other members of an activated coagulation system. Furthermore, the C5 purified from human plasma carries the native glycosylation structure on asparagine64. Glycosylation had not been present on the murine mirror image C5a polypeptide that was used for identification of NOX-D19, NOX-D20, NOX-D21 and other nucleic acid molecules according to the present invention.

Binding to C5 may influence pharmacokinetics due to the expected low clearance of the large C5 protein and a published plasma concentration of 350-390 nM. Binding to C5 may also influence pharmacodynamics. C5 is bound by C5a binding nucleic acid molecules such as NOX-20 and NOX-D21 and thus C5a is already blocked by the Spiegelmer before it is liberated and may lead to receptor signaling.

EXAMPLE 2: SYNTHESIS AND DERIVATIZATION OF APTAMERS AND SPIEGELMERS

Small Scale Synthesis

Aptamers (D-RNA nucleic acids) and Spiegelmers (L-RNA nucleic acids) were produced by solid-phase synthesis with an ABI 394 synthesizer (Applied Biosystems, Foster City, CA, USA) using 2'TBDMS RNA phosphoramidite chemistry (Damha and Ogilvie, 1993). rA(N-Bz)-, rC(Ac)-, rG(N-ibu)-, and rU-phosphoramidites in the D- and L-configuration were purchased from ChemGenes, Wilmington, MA. Aptamers and Spiegelmers were purified by gel electrophoresis.

Large Scale Synthesis Plus Modification

Spiegelmers were produced by solid-phase synthesis with an AktaPilot100 synthesizer (Amersham Biosciences; General Electric Healthcare, Freiburg) using 2'TBDMS RNA phosphoramidite chemistry (Damha and Ogilvie, 1993). L-rA(N-Bz)-, L-rC(Ac)-, L-rG(N-ibu)-, and L-rU-phosphoramidites were purchased from ChemGenes, Wilmington, MA. The 5'-amino-modifier was purchased from American International Chemicals Inc. (Framingham, MA, USA). Synthesis of the unmodified or 5'-Amino-modified Spiegelmer was started on L-riboG, L-riboC, L-riboA or L-riboU modified CPG pore size 1000 Å (Link Technology, Glasgow, UK. For coupling (15 min per cycle), 0.3 M benzylthiotetrazole (CMS-Chemicals, Abingdon, UK) in acetonitrile, and 3.5 equivalents of the respective 0.1 M phosphoramidite solution in acetonitrile was used. An oxidation-capping cycle was used. Further standard solvents and reagents for oligonucleotide synthesis were purchased from Biosolve (Valkenswaard, NL). The Spiegelmer was synthesized DMT-ON; after deprotection, it was purified via preparative RP-HPLC (Wincott et al., 1995) using Source15RPC medium (Amersham). The 5'DMT-group was removed with 80% acetic acid (30 min at RT). Subsequently, aqueous 2 M NaOAc solution was added and the Spiegelmer was desalted by tangential-flow filtration using a 5 K regenerated cellulose membrane (Millipore, Bedford, MA).

PEGylation of Spiegelmers

In order to prolong the Spiegelmer's plasma residence time in vivo, Spiegelmers was covalently coupled to a 40 kDa polyethylene glycol (PEG) moiety at 5'-end For PEGylation (for technical details of the method for PEGylation see European patent application EP 1 306 382), the purified 5'-amino modified Spiegelmer was dissolved in a mixture of $H_2O$ (2.5 ml), DMF (5 ml), and buffer A (5 ml; prepared by mixing citric acid·$H_2O$ [7 g], boric acid [3.54 g], phosphoric acid [2.26 ml], and 1 M NaOH [343 ml] and adding water to a final volume of 1l; pH=8.4 was adjusted with 1 M HCl).

The pH of the Spiegelmer solution was brought to 8.4 with 1 M NaOH. Then, 40 kDa PEG-NHS ester (Jenkem Technology, Allen, TX, USA) was added at 37° C. every 30 min in six portions of 0.25 equivalents until a maximal yield of 75 to 85% was reached. The pH of the reaction mixture was kept at 8-8.5 with 1 M NaOH during addition of the PEG-NHS ester.

The reaction mixture was blended with 4 ml urea solution (8 M), and 4 ml buffer B (0.1 M triethylammonium acetate in $H_2O$) and heated to 95° C. for 15 min. The PEGylated Spiegelmer was then purified by RP-HPLC with Source 15RPC medium (Amersham), using an acetonitrile gradient (buffer B; buffer C: 0.1 M triethylammonium acetate in acetonitrile). Excess PEG eluted at 5% buffer C, PEGylated Spiegelmer at 10-15% buffer C. Product fractions with a purity of >95% (as assessed by HPLC) were combined and mixed with 40 ml 3 M NaOAc. The PEGylated Spiegelmer was desalted by tangential-flow filtration (5 K regenerated cellulose membrane, Millipore, Bedford MA).

EXAMPLE 3: DETERMINATION OF BINDING CONSTANTS TO C5A FOR APTAMERS (PULL-DOWN ASSAY)

Direct Pull-Down Assay

The affinity of C5a binding nucleic acids was measured as binding of aptamers (D-RNA nucleic acids) to biotinylated mouse D-C5a (SEQ. ID. 89) in a pull down assay format at 37° C. Aptamers were 5'-phosphate labeled by T4 polynucleotide kinase (Invitrogen) using [$\gamma$-$^{32}$P]-labeled ATP (Hartmann Analytic, Braunschweig, Germany). The specific radioactivity of labeled aptamers was 200,000-800,000 cpm/pmol. Assays were carried out in selection buffer (20 mM Tris-HCl pH 7.4; 150 mM NaCl; 5 mM KCl; 1 mM MgCl$_2$; 1 mM CaCl$_2$; 4 U/ml RNase inhibitor (RNaseOUT, Invitrogen); 0.1% [w/vol] Tween-20 supplemented with 50 µg/ml bovine serum albumin (Sigma), and 10 µg/ml non-specific Spiegelmer in order to prevent adsorption of binding partners with surfaces of used plasticware or the immobilization matrix). Aptamers were incubated after de- and renaturation at 0.2-1 nM concentration at 37° C. in selection buffer together with varying amounts of biotinylated mouse D-C5a for 3-4 hours in order to reach equilibrium at low concentrations.

The concentration range of biotinylated mouse D-C5a was set from 640 pM to 10 µM; total reaction volume was 80-200 µl. Biotinylated mouse D-C5a and complexes of aptamer and biotinylated mouse D-C5a were immobilized on 5 µl NeutrAvidin Agarose Plus particles (Pierce Biotechnology) which had been preequilibrated with selection buffer. Particles were kept in suspension for 30 min at the 37° C. in a thermomixer. Immobilized radioactivity was quantitated in a scintillation counter after detaching the supernatant and appropriate washing. The percentage of binding was plotted against the concentration of biotinylated mouse D-C5a and dissociation constants were obtained by using software algorithms (GraphPad Prism) assuming a 1:1 stoichiometry.

Competitive Pull-Down Assay

In order to compare different D-C5a binding nucleic acids, a competitive ranking assay was performed. For this purpose the most affine aptamer available was radioactively labeled (see above) and served as reference. After de- and renaturation it was incubated in selection buffer at 37° C. with biotinylated mouse D-C5a at conditions that resulted in around 5-10% binding to the biotinylated mouse D-C5a after immobilization and washing on 4 µl NeutrAvidin Agarose Plus particles (Pierce Biotechnology) without competition. An excess of de- and renatured non-labeled D-RNA aptamer variants was added at concentrations ranging from 9 pM-400 nM with the labeled reference aptamer to parallel binding reactions; total reaction volume was 160-400 µl. After 3-4 hour incubation biotinylated mouse D-C5a and complexes of aptamer and biotinylated were immobilized and assays were analysed as described above. The aptamers to be tested competed with the reference aptamer for target binding, thus decreasing the binding signal in dependence of their binding characteristics. The aptamer that was found most active in this assay could then serve as anew reference for comparative analysis of further aptamer variants.

EXAMPLE 4: BIACORE MEASUREMENT OF SPIEGELMERS BINDING TO C5A And Related Peptides The instrument was set to an enduring temperature of 37° C. The Biacore 2000 instrument was cleaned using the DESORB method before the start of each experiment/immobilization of a new chip. After docking a maintenance chip, the instrument was consecutively primed with desorb solution 1 (0.5% sodium dodecyl sulphate, SDS), desorb solution 2 (50 mM glycine, pH 9.5) and HBS-EP buffer. Finally, the system was primed with HBS-EP buffer.

For Biacore experiments the C5a-binding Spiegelmers were prepared in sterile water and had a concentration of 100 µM.

The CM5 chip was primed with HBS-EP buffer and equilibrated until a stable baseline was observed. The flow cells were immobilized beginning from flow cell 4 to flow cell 1. 100 µl of a 1:1 mixture of 0.4 M EDC and 0.1 M NHS were injected using the QUICKINJECT command at a flow of 10 µl/min. Activation of the flow cell was monitored by an increase in RU after NHS/EDC injection (typically 150-500 RU for CM5 chips). Solutions of 0.1-1 µg/ml in 10 mM NaAc pH5.5 for C5a or 10 mM NaAc pH5.5 for human C5 were transferred to a vial and injected using the MANUALINJECT command at a flow of 10 µl/min. 1000-3000 RU were immobilized the chip. All flow cells were then blocked with an injection of 70 µl of 1 M ethanolamine hydrochloride, pH 8 at a flow of 10 µl/min. Injection of 30 µl of the regeneration solution (1 M NaCl) at a flow of 30 µl/min was performed to remove unspecifically bound protein from the chip surface.

Kinetic parameters and dissociation constants were evaluated by a series of Spiegelmer injections at concentrations of 2,000-1,000-500-200-125-62.5-31.3-15.6(2×)-7.8-3.9-1.95-0.98-0.48-0.24-0.12-0 nM diluted in running buffer, starting with the lowest concentration.

In all experiments, the analysis was performed at 37° C. using the Kinject command defining an association time of 240 and a dissociation time of 240 seconds at a flow of 30 µl/min. The assay was double referenced, whereas FC1 served as (blocked) surface control (bulk contribution of each Spiegelmer concentration) and a series of buffer injections without analyte determined the bulk contribution of the buffer itself. At least one Spiegelmer concentration was injected twice to monitor the regeneration efficiency and chip integrity during the experiments. Regeneration was performed by injecting 60 µl of 1M NaCl at a flow of 30 µl/min. Stabilization time of baseline after each regeneration cycle was set to 1 min at 30 µl/min.

Data analysis and calculation of dissociation constants (KD) was done with the BIAevaluation 3.1.1 software (BIACORE AB, Uppsala, Sweden) using a modified Langmuir 1:1 stoichiometric fitting algorithm, with a constant RI and mass transfer evaluation with a mass transport coefficient kt of 1×10$^7$ [RU/M*s].

EXAMPLE 5: DETERMINATION OF INHIBITORY CONCENTRATION IN A CHEMOTAXIS ASSAY

Generation of a Cell Line Expressing the Human Receptor for C5a

A stably transfected cell line expressing the human receptor for C5a was generated by transfecting BA/F3 mouse pro B cells with a plasmid coding for the human C5a receptor (NCBI accession NM_001736 in pcDNA3.1+). Cells expressing C5aR were selected by treatment with geneticin and tested for expression with RT-PCR and for functionality with chemotaxis assay.

Chemotaxis Assay

The day before the experiment, cells are seeded in anew flask at 0.3×10$^6$/ml. For the experiment, cells were centrifuged, washed once in HBH (HBSS, containing 1 mg/ml bovine serum albumin and 20 mM HEPES) and resuspended at 1.33×10$^6$ cells/ml. 75 µl of this suspension were added to the upper compartments of a 96 well Corning Transwell plate with 5 µm pores (Costar Corning, #3388; NY, USA). In the lower compartments recombinant human C5a (SEQ. ID. 50) or mouse C5a (SEQ. ID. 54) was pre-incubated together with Spiegelmers in various concentrations in 235 µl HBH at 37° C. for 20 to 30 min prior to addition of cells. Cells were allowed to migrate at 37° C. for 3 hours. Thereafter the insert plate (upper compartments) was removed and 30 µl of 440 µM resazurin (Sigma, Deisenhofen, Germany) in phosphate buffered saline was added to the lower compartments. After incubation at 37° C. for 2.5 hours, fluorescence was measured at an excitation wavelength of 544 nm and an emission wavelength of 590 nm.

Fluorescence values are corrected for background fluorescence (no C5a in well) and plotted against Spiegelmer concentration. The $IC_{50}$ values are determined with non-linear regression (4 parameter fit) using GraphPad Prism. Alternatively, the value for the sample without Spiegelmer (C5a only) is set 100% and the values for the samples with Spiegelmer are calculated as percent of this. The percent-values are plotted against Spiegelmer concentration and the $IC_{50}$-values are determined as described above.

Determination of the Half-Maximal Effective Concentration ($EC_{50}$) for Human and Mouse C5a After 3 hours migration of BA/F3/huC5aR cells towards various human C5a or mouse C5a concentrations, dose-response curves for human and mouse C5a were obtained, indicating half effective concentrations ($EC_{50}$) of 0.1 nM for huC5a and 0.3 nM for mC5a. For the experiments on inhibition of chemotaxis by Spiegelmers 0.1 nM human C5a and 0.3 nM mouse C5a were used.

EXAMPLE 6: INHIBITION OF C5A-Induced Activation Of Primary Human Neutrophils

Isolation of Human PMNs

Polymorphonuclear leukocytes (PMN) were isolated from whole blood by discontinuous gradient centrifugation at room temperature. Blood was collected in acid citrate dextrose containing blood collection tubes (Sarstedt). Dextran 500 (Accurate Chemical) was added to a final concentration of 2% w/v and the blood/dextran was layered on to Histopaque (1.077 g/ml, Sigma). After centrifugation all liquid and cells above the gradient interface were discarded. Pellet and circa 80% of remaining liquid above were collected and diluted 1:1 with a mixture of Voluven 80% v/v (Fresenius Kabi), PBS 16% v/v (Sigma) and ACD 4% v/v (Sigma). Mixture was centrifuged at 400 rpm for 15 minutes. Supernatant was collected and centrifuged at 1,000 rpm for 7 minutes. The pellet was gently re-suspended and remaining erythrocytes were removed by lysis.

Inhibition of C5a-Induced Chemotaxis of Human PMNs

Human C5a (1 nM) was preincubated with indicated concentrations of NOX-D19 or NOX-D20 in HBSS+0.01% BSA+25 mM HEPES in the lower chamber of a chemotaxis plate. Human neutrophils were added to the upper chambers of a chemotaxis plate and chemotaxis was performed over 25 min at 37° C. and 5% $CO_2$. Following incubation the upper chamber was fitted to a white luminescence plate containing Accutase to harvest cells bound to the underside of the chemotaxis mesh. Glo reagent (Promega) was added and equilibrated for 10 min. Luminescence was measured using a Biotek Synergy 2 plate reader.

Inhibition of C5a-Induced Elastase Release by Human PMNs

Human neutrophils were primed with TNFα (10 ng/ml) and cytochalasin B (5 µg/ml) for 30 minutes at 37° C., 5% $CO_2$. Cells were stimulated for 45 min with human C5a (30 nM) which had been pre-incubated with NOX-D19 or NOX-D20 at indicated concentrations. Cells were then separated by centrifugation and 25 µl of supernatant were incubated with elastase substrate (Calbiochem) in Tris-HCl 0.1 M pH 7.4 for 1 h at 37° C. with readings being taken at an absorbance of 405 nm every 5 minutes. The kinetic data was analysed to determine the $v_{max}$ for each sample. The mean percentage elastase activity relative to control was calculated for each sample (background not subtracted).

Results

NOX-D19 and NOX-D20 efficiently inhibit the activation of freshly isolated human peripheral blood PMN by C5a. 10 nM NOX-D19 or NOX-D20 were sufficient to block more than 85% of huC5a-induced chemotaxis of human PMN (FIG. 13A). HuC5a-induced release of antimicrobial elastase was efficiently inhibited by NOX-D19 and NOX-D20 (FIG. 13B). 30 nM NOX-D19 or NOX-D20 suppressed about 50% of C5a-induced elastase release. Of note, for stoichiometric reasons the sensitivity of this assay is limited to $IC_{50}$=15 nM, as elastase release is induced by 30 nM huC5a.

EXAMPLE 7: C5A BINDING NUCLEIC ACIDS DO NOT INTERFERE WITH COMPLEMENT-DEPENDENT HEMOLYSIS

The ultimate product of the complement cascade is the membrane attack complex (MAC), a pore consisting of C5b-9. MAC is believed to insert into the cytoplasmic membranes of pathogens and kill them by induction of cytoplasmic leakage.

The C5a binding nucleic acids (Spiegelmers) presented here have been shown to recognize C5a in the context of C5 (see Example 1, FIG. 9 and FIG. 10). Therefore it was investigated whether C5 cleavage to the anaphylatoxin C5a and C5b, which is part of the MAC is inhibited by these the Spiegelmers. This was achieved by using a complement-dependent sheep erythrocyte hemolysis test.

Methods

Reconstituted human lyophilized serum ('Human Complement Serum' (Sigma Aldrich, Germany) was pre-incubated with PEGylated Spiegelmers NOX-D19, NOX-D20 and NOX-D21 in the range of 10 nM to 10,000 nM in 96-well plates (Nunc-Immuno™ Plate, MaxiSorp Surface™). As a positive control the C5-binding aptamer C5C6 with maximal 2'OMe purine and 2'fluoro pyrimidine substitution (Biesecker et al. 1999) (synthesized in house) which inhibits C5 cleavage was used in the same concentration range. As a control for potential unspecific Spiegelmer effects on the assay PEGylated Spiegelmers with the reverse sequence of NOX-D19 and NOX-D21, revNOX-D19 and revNOX-D21 were included. revNOX-D19 and revNOX-D21 were earlier shown not to inhibit C5a in a Biacore and cell based assays. After 1 hour incubation at 37° C. sheep erythrocytes opsonized with rabbit anti-sheep erythrocyte antibodies, known as hemolytic system (Institut Virion/Serion GmbH, Germany) were added to the pre-incubated serum complement inhibitor mixture. Complement is activated via the classical pathway leading to the cleavage of C5 to C5a and C5b. C5b then associates with C6-C9 to form the lytic membrane attack complex (MAC). Sheep erythrocyte hemolysis due to MAC formation was determined 30 min later by a colorimetric measurement after spinning down intact cells. The higher the degree of hemolysis the higher the absorption at 405 nm (measured in a Fluo Star plate reader).

Results

The aptamer C5C6 inhibited complement-dependent lysis of the sheep erythrocytes with an $IC_{50}$ of approximately 1 µM (FIG. 14 A, B). The Spiegelmers tested, namely C5 and C5a binding nucleic acids NOX-D19 and NOX-D20 (FIG. 14 A) and NOX-D21 (FIG. 14 B) and the non-C5- or C5a-binding Spiegelmers revNOX-D19 (FIG. 14 A) and revNOX-D21 (FIG. 14 B) did not inhibit hemolysis.

DISCUSSION

The C5a binding Spiegelmers tested were shown not to inhibit MAC formation and are therefore selective antagonists of C5a only. If used as a medicine, this may be advantageous, since inhibition of MAC-formation can compromise the body's defense mechanism to invading pathogens, mainly Gram-negative bacteria.

EXAMPLE 8: THE C5A-BINDING NUCLEIC ACID NOX-D19 SHOWS EFFICACY IN THE MURINE CECAL LIGATION AND PUNCTURE MODEL FOR POLYMICROBIAL SEPSIS

The effect of intraperitoneal injections of NOX-D19 on the course of polymicrobial sepsis was tested in a rodent cecal ligation and puncture (CLP) model.

Methods

Animal Model 10-12 week old male C57BL/6 mice (Charles River Laboratories, Germany) were used for the study. Peritonitis was surgically induced under light isofluran anesthesia. Incisions were made into the left upper quadrant of the peritoneal cavity (normal location of the cecum). The cecum was exposed and a tight ligature was placed around the cecum with sutures distal to the insertion of the small bowel (75% were ligated). One puncture wound was made with a 24-gauge needle into the cecum and small amounts of cecal contents were expressed through the wound. The cecum was replaced into the peritoneal cavity and the laparotomy site was closed. 500 µl saline was given s.c. as fluid replacement. Sham animals underwent the same procedure except for ligation and puncture of the cecum. Finally, animals were returned to their cages with free access to food and water.

Study Groups 4 groups (n=6 mice for sham surgery and n=10 mice per group for CLP surgery) were tested: (1) sham surgery with vehicle (saline) treatment, (2) CLP surgery with vehicle treatment, (3) CLP surgery with low dose NOX-D19 (1 mg/kg) treatment and (4) CLP surgery with high dose NOX D19 (10 mg/kg) treatment. The investigators were blinded to the treatment strategy and did not know which compound contains vehicle or *verum*. Route of administration was i.p. every day for 6 days starting at time of the CLP surgery.

Survival

Follow up was 7 days in each group. Mice were monitored daily and Kaplan Meier survival curves were generated using GraphPad Prism 4 software.

Blood Drawing

Blood samples were obtained under light ether anaesthesia from the cavernous sinus with a capillary prior to surgery (baseline, day −4) and at day 1 after surgery to allow measurement of routine serum markers of acute kidney injury (serum creatinine, and blood urea nitrogen, BUN) and acute liver failure (serum alanin-aminotransferase, serum ALT). The level of aspartate aminotransferase (serum AST) was measured in serum as a marker of multiorgan failure. Measurement of clinical chemistry parameters was performed on an Olympus analyser (AU400).

Statistics

Statistical significance was calculated by Student's T-test. For survival Kaplan Meier curves were generated and log rank test for significance was performed. GraphPad Prism 4 software was used.

Results

Survival

As expected no mortality occurred in animals with sham surgery without CLP (FIG. 15). In mice that received CLP surgery and were treated with vehicle only, median survival was 1.5 days NOX-D19 treatment after CLP surgery improved median survival (FIG. 15). Mice treated with low dose NOX-D19 (1 mg/kg) showed the longest median survival (5 days, p<0.0001 vs. vehicle). Mice treated with high dose NOX-D19 (10 mg/kg) had a median survival of 3 days which was significantly longer than in vehicle treated mice (p=0.0401) but was not significantly different from low dose NOX-D19 treatment (p=0.4875). 100% of vehicle mice died within 4 days after CLP surgery. 100% and 90% mortality occurred not before 7 days in mice treated with low and high dose NOX-D19, respectively (FIG. 15).

Clinical Chemistry

Renalfunction

The serum creatinine and blood urea nitrogen (BUN) concentration are parameters for renal function. Renal function was assessed before the start of the study (day −4) and on day 1 after CLP surgery.

By day 1 CLP induced a significant increase in serum creatinine levels in vehicle treated mice. Low dose NOX-D19 treatment (1 mg/kg) prevented this increase (FIG. 16 A). In mice treated with high dose NOX-D19 (10 mg/kg) a moderate but statistically not significant increase in serum creatinine levels was observed (p=0.1873 vs. vehicle) (FIG. 16 A).

BUN (FIG. 16 B), which is a more sensitive parameter of renal function than creatinine, was significantly increased at day 1 after CLP surgery in vehicle treated mice. Treatment of mice with low and high dose NOX-D19 significantly suppressed the increase of BUN upon CLP (FIG. 16 B).

Liver Function

The most reliable marker of hepatocellular injury or necrosis is serum alanine aminotransferase (serum ALT). All groups showed an increase of serum ALT at day 1 after CLP surgery. However, both groups of NOX-D19 treated septic mice demonstrated improved liver function compared to vehicle treated mice (FIG. 17 A).

Multiorgan Failure

The serum level of aspartate aminotransferase (serum AST) (FIG. 17 B) was measured as a marker of multiorgan failure since AST has been shown to be elevated in diseases affecting other organs besides liver, such as myocardial infarction, acute pancreatitis, acute hemolytic anemia, severe burns, acute renal disease, musculoskeletal diseases, and trauma.

Similar to ALT, all groups showed an increase of AST levels at day 1 after CLP surgery (p<0.001 vs. sham). However, similar to liver function, both groups of NOX-D19 treated septic mice demonstrated less pronounced AST levels compared to vehicle treated mice (FIG. 17 B).

EXAMPLE 9: THE IMPROVED C5A-BINDING NUCLEIC ACID NOX-D20 SHOWS EFFICACY IN THE MURINE CECAL LIGATION AND PUNCTURE MODEL FOR POLYMICROBIAL SEPSIS

The effect of intraperitoneal injections of NOX-D20 on the course of polymicrobial sepsis was tested in a rodent cecal ligation and puncture (CLP) model.

Methods

Animal Model

Polymicrobial sepsis was induced in 10-12 week old male C57BL/6 mice (Charles River Laboratories, Germany) as described in Example 8 with 60-75% of the cecum being ligated.

Survival

Follow up was 7 days in each group. Mice were monitored daily and Kaplan Meier survival curves were generated using GraphPad Prism 4 software.

Study Groups 5 groups (n=5 mice for sham surgery and n=10 mice per group for CLP surgery) were tested: (1) sham surgery with vehicle (saline) treatment, (2) CLP surgery with vehicle treatment, (3) CLP surgery with daily low dose NOX-D20 (1 mg/kg) treatment, (4) CLP surgery with daily high dose NOX-D20 (3 mg/kg) treatment and (5) CLP surgery with a single low dose NOX-D20 (1 mg/kg) after surgery followed by daily vehicle treatment. The investigators were blinded to the treatment strategy and did not know which compound contains vehicle or *verum*. Route of administration was i.p.

Clinical Chemistry and Inflammatory Parameters

Blood samples were obtained as described in Example 8 under light ether anaesthesia from the cavernous sinus with a capillary at day 1 after surgery. Routine serum markers of acute kidney injury (serum creatinine, and blood urea nitrogen, BUN), acute liver failure (serum ALT) and endothelial injury (serum lactate dehydrogenase, serum LDH) were measured. Peritoneal lavage (PL) was performed using 3 ml PBS. The volume of the collected PL was measured in each sample, and the total cell count was assessed using a hemocytometer (Neubauer Zaehlkammer, Gehrden, Germany). Serum and PL levels of tumor necrosis factor alpha (TNF-α), interleukin-6 (IL-6), and CCL2 (=macrophage chemoattractant protein-1, MCP-1) were quantified by bead-based flow cytometry assay (CBA Kit, BD Biosciences, Heidelberg, Germany). Serum and PL concentrations of CXCL1 (=keratinocyte chemoattractant, KC) and CXCL2 (=macrophage inflammatory protein 2, MIP-2) were determined by ELISA (R&D Systems, Wiesbaden, Germany). Differential cell count in the PL was performed on hematoxylin and eosin (H&E) stained cytospins (cytospin4, Thermo Scientific).

Capillary Leakage

Immediately after CLP surgery, 0.25% w/v Evans blue (200 μl) was injected intravenously. After 18 h mice were sacrificed and PL was performed as described above. Concentrations of Evans Blue dye in serum and PL fluids was measured spectrophotometrically at 620 nm. The following formula was used to correct the optical densities for contamination with heme pigments: E620 (corrected)=E620 (raw)−(E405 (raw)×0.014). Plasma exudation was quantitated as the ratio of extinction in PL fluid to extinction in plasma.

Statistics

Statistical significance was calculated by one-way ANOVA and Dunnetts test. For survival long rank test for significance was performed. GraphPad Prism 4 software was used.

Results

Survival

As expected no mortality occurred in sham operated mice within 7 days after surgery (FIG. 18). In vehicle-treated CLP mice median survival was 3 days. Daily treatment of mice with 1 mg/kg NOX-D20 significantly prolonged median survival to 7 days (p=0.0043 vs. vehicle). An increase of the dosage to 3 mg/kg NOX-D20 had no additional protective effect with a similar median survival of 6.5 days (p=0.0092 vs. vehicle). Notably, a single injection of 1 mg/kg NOX-D20 after CLP surgery was as effective as daily treatment and significantly prolonged median survival to 6.5 days (FIG. 18). While 100% of vehicle treated mice dies within 5 days, 30-40% of NOX-D20 treated mice were still alive at the end of the experiment at day 7 (FIG. 18).

Organ Function

Systemic inflammation often causes multiple organ failure. Increased serum levels of creatinine and BUN are parameters for decreased glomerular filtration rate and kidney failure. Both parameters were significantly increased in vehicle treated mice one day after CLP surgery compared to sham mice. NOX-D20 treatment efficiently prevented the increase of both markers implying a protective effect of NOX-D20 on renal function (FIG. 19 A, B). Alanine aminotransferase (ALT) is a common marker of hepatocellular injury and necrosis and CLP-induced sepsis was associated with increased of ALT serum levels. NOX-D20 treated mice demonstrated significantly reduced levels of serum ALT compared to vehicle treated mice suggesting improved liver function (FIG. 19 C). Elevated serum levels of lactate dehydrogenase (LDH) occur after tissue injury and are therefore a general marker of organ failure. The increase in LDH levels provoked by CLP was effectively blocked by NOX-D20 (FIG. 20 A). Breakdown of the endothelial barrier and edema formation is a common fatal event in sepsis. Sepsis induction resulted in a two-fold increase in relative plasma protein extravasation into the peritoneal cavity in vehicle treated compared to sham operated mice. NOX-D20 treatment significantly inhibited capillary leakage (FIG. 20 B). For all parameters tested here 1 mg/kg NOX-D20 was sufficient to significantly improve organ function which is reflected in improved survival of NOX-D20 treated mice.

Inflammation

CLP resulted in a strong local and systemic upregulation of pro-inflammatory cytokines and chemokines. Blockade of C5a by NOX-D20 efficiently reduced the concentrations of TNFα, IL-6, CCL2, CXCL1 and CXCL2 in the peritoneum and in serum at day 1 after CLP. The up-regulation of these chemokines is associated with a recruitment of polymorphonuclear leukocytes (PMN) to the peritoneum. Accordingly, C5a-inhibition by NOX-D20 inhibited the accumulation of PMN in the peritoneal cavity (FIG. 20 C). Similarly, infiltration of monocytes was blocked by NOX-D20.

EXAMPLE 10: EFFICACY OF NOX-D21 IN A MODEL OF ISCHEMIA REPERFUSION-INDUCED ACUTE KIDNEY INJURY

The effect of NOX-D21 on acute kidney injury (AKI) was tested in a rodent model of renal ischemia/reperfusion injury (IRI).

Methods

Animal Model 12-15 week old male C57BL/6 mice (Charles River, Germany) were anaesthetized using isoflurane via a nose mask and placed supine on a heating table to maintain body temperature around 32° C. Midline incision was performed and the right and left renal pedicle were clipped with a micro-aneurysm clip for 30 min. After removal of the clip and suture of the skin mice were returned to the cages and monitored until fully awake.

Study Groups 3 groups (n=10 mice per group) were tested: (1) IRI surgery with vehicle treatment, (2) IRI surgery with low dose NOX-D21 (1 mg/kg) treatment, (3) IRI surgery with high dose NOX-D21 (10 mg/kg) treatment. The investigators were blinded to the treatment strategy and did not know which compound contains vehicle or verum. NOX-D21 was given i.v. 1 h prior to surgery at d0 and during the next 3 days (d1-d3) it was given i.p. once daily.

Survival

Mice were monitored daily for 14 days. Kaplan Meier survival curves were generated and significance was determined by log-rank test using GraphPad Prism 4 software.

Results

Survival was significantly improved by treatment with high NOX-D21 (FIG. 21). Low dose NOX-D21 treatment resulted in an evident yet not statistically significant improvement of survival.

In the control group treated with vehicle only one mouse survived until day 14. NOX-D21 treatment increased the percentage of surviving mice to 45-55% (FIG. 21).

REFERENCES

The complete bibliographic data of the documents recited herein the disclosure of which is incorporated by reference is, if not indicated to the contrary, as follows.

Altschul S F, Gish W, Miller W, Myers E W, Lipman D J (1990), Basic local alignment search tool. J Mol Biol. 215(3):403-10.

Altschul S F, Madden T L, Schaffer A A, Zhang J, Zhang Z, Miller W, Lipman D J (1997). Gapped BLAST and PSI-BLAST: a new generation of protein database search programs. Nucleic Acids Res. 25(17):3389-402.

Arumugam T V, Shiels I A, Strachan A J, Abbenante G, Fairlie D P, Taylor S M (2003) A small molecule C5a receptor antagonist protects kidneys from ischemia/reperfusion injury in rats. Kidney Int 63(1): 134-142

Arumugam T V, Woodruff T M, Stocks S Z, Proctor L M, Pollitt S, Shiels I A, Reid R C, Fairlie D P, Taylor SM (2004) Protective effect of a human C5a receptor antagonist against hepatic ischaemia-reperfusion injury in rats. J Hepatol 40(6): 934-941

Bergh K, Iversen O J, Lysvand H. (1993). Surprisingly high levels of anaphylatoxin C5a des Arg are extractable from psoriatic scales. Arch Dermatol Res 285(3):131-134.

Biesecker G, Dihel L, Enney K, Bendele R A (1999) Derivation of RNA aptamer inhibitors of human complement C5. Immunopharmacology 42(1-3): 219-230.

Bonifati D M, Kishore U. (2007) Role of complement in neurodegeneration and neuroinflammation. Mol Immunol 44(5): 999-1010.

Bosmann M, Ward P A (2012) Role of C3, C5 and anaphylatoxin receptors in acute lung injury and in sepsis. Adv Exp Med Biol 946: 147-159

Breivik T, Gundersen Y, Gjermo P, Taylor S M, Woodruff T M, Opstad P K (2011) Oral treatment with complement factor C5a receptor (CD88) antagonists inhibits experimental periodontitis in rats. J Periodontal Res 46(6): 643-647

Chen M, Daha M R, Kallenberg C G (2010) The complement system in systemic autoimmune disease. J Autoimmun 34(3): J276-286

Copland D A, Hussain K, Baalasubramanian S, Hughes T R, Morgan B P, Xu H, Dick A D, Nicholson L B (2010) Systemic and local anti-C5 therapy reduces the disease severity in experimental autoimmune uveoretinitis. Clin Exp Immunol 159(3): 303-314

Czermak B J, Sarma V, Pierson C L, Warner R L, Huber-Lang M, Bless N M, Schmal H, Friedl H P, Ward P A (1999) Protective effects of C5a blockade in sepsis. Nat Med 5(7): 788-792

Damha M J and Ogilvie K K, Methods in Molecular Biology, Vol. 20 Protocols for oligonucleotides and analogs, ed. S. Agrawal, p. 81-114, Humana Press Inc. (1993)

Ehrnthaller C, Ignatius A, Gebhard F, Huber-Lang M (2011) New Insights of an Old Defense System: Structure, Function, and Clinical Relevance of the Complement System. Mol Med 17(3-4): 317-329

Farkas I, Baranyi L, Liposits Z S, Yamamoto T, Okada H (1998) Complement C5a anaphylatoxin fragment causes apoptosis in TGW neuroblastoma cells. Neuroscience 86(3): 903-911

Fernandez H N, Hugh T E (1978) Primary structural analysis of the polypeptide portion of human C5a anaphylatoxin. Polypeptide sequence determination and assignment of the oligosaccharide attachment site in C5a. J Biol Chem 253(19): 6955-6964

Flierl M A, Rittirsch D, Nadeau B A, Day D E, Zetoune F S, Sarma J V, Huber-Lang M S, Ward P A (2008) Functions of the complement components C3 and C5 during sepsis. FASEB J 22(10): 3483-3490

Fonseca M I, Ager R R, Chu S H, Yazan O, Sanderson S D, LaFerla F M, Taylor S M, Woodruff T M, Tenner A J (2009) Treatment with a C5aR antagonist decreases pathology and enhances behavioral performance in murine models of Alzheimer's disease. J Immunol 183(2): 1375-1383

Gueler F, Rong S, Gwinner W, Mengel M, Brocker V, Schon S, Greten T F, Hawlisch H, Polakowski T, Schnatbaum K, Menne J, Haller H, Shushakova N (2008) Complement 5a receptor inhibition improves renal allograft survival. J Am Soc Nephrol 19(12): 2302-2312

Heller T, Hennecke M, Baumann U, Gessner J E, zu Vilsendorf A M, Baensch M, Boulay F, Kola A, Klos A, Bautsch W, Kohl J. (1999) Selection of a C5a receptor antagonist from phage libraries attenuating the inflammatory response in immune complex disease and ischemia/reperfusion injury. J Immunol 163(2):985-994.

Hillmen P, Muus P, Duhrsen U, Risitano A M, Schubert J, Luzzatto L, Schrezenmeier H, Szer J, Brodsky R A, Hill A, Socie G, Bessler M, Rollins S A, Bell L, Rother R P, Young N S (2007). Effect of the complement inhibitor eculizumab on thromboembolism in patients with paroxysmal nocturnal hemoglobinuria. Blood, 110(12):4123-8

Huber-Lang M, Sarma V J, Lu K T, McGuire S R, Padgaonkar V A, Guo R F, Younkin E M, Kunkel R G, Ding J, Erickson R, Cumutte J T, Ward P A (2001) Role of C5a in multiorgan failure during sepsis. J Immunol 166(2): 1193-1199

Huber-Lang M S, Younkin E M, Sarma J V, McGuire S R, Lu K T, Guo R F, Padgaonkar V A, Cumutte J T, Erickson R, Ward P A (2002) Complement-induced impairment of innate immunity during sepsis. J Immunol 169(6): 3223-3231

Jacob A, Hack B, Bai T, Brorson J R, Quigg R J, Alexander J J (2010a) Inhibition of C5a receptor alleviates experimental CNS lupus. J Neuroimmunol 221(1-2):46-52

Jacob A, Hack B, Chiang E, Garcia J G, Quigg R J, Alexander J J (2010b) C5a alters blood-brain barrier integrity in experimental lupus. FASEB J 24(6):1682-8

Kambas K, Markiewski M M, Pneumatikos I A, Rafail S S, Theodorou V, Konstantonis D, Kourtzelis I, Doumas M N, Magotti P, Deangelis R A, Lambris J D, Ritis K D (2008) C5a and TNF-alpha up-regulate the expression of tissue factor in intra-alveolar neutrophils of patients with the acute respiratory distress syndrome. J Immunol 180(11): 7368-7375

Khan M A, Jiang X, Dhillon G, Beilke J, Holers V M, Atkinson C, Tomlinson S, Nicolls M R (2011) CD4+ T cells and complement independently mediate graft ischemia in the rejection of mouse orthotopic tracheal transplants. Circ Res 109(11): 1290-1301 Kirschfink M. (1997) Controlling the complement system in inflammation. Immunopharmacology 38(1-2):51-62.

Klos A, Tenner A J, Johswich K O, Ager R R, Reis E S, Kohl J (2009) The role of the anaphylatoxins in health and disease. Mol Immunol 46(14): 2753-2766

Klussmann S. (2006). "The Aptamer Handbook—Functional Oligonucleotides and their Applications." Edited by S. Klussmann. WILEY-VCH, Weinheim, Germany, ISBN 3-527-31059-2

Kohl J. (2001) Anaphylatoxins and infectious and non-infectious inflammatory diseases. Mol Immunol 38(2-3): 175-187.

Kusser W (2000). J Biotechnol 74:27-38

Laudes I J, Chu J C, Sikranth S, Huber-Lang M, Guo R F, Riedemann N, Sarma J V, Schmaier A H, Ward P A (2002) Anti-c5a ameliorates coagulation/fibrinolytic protein changes in a rat model of sepsis. Am J Pathol 160(5): 1867-1875

Lewis A G, Kohl G, Ma Q, Devarajan P, Kohl J. (2008) Pharmacological targeting of C5a receptors during organ preservation improves kidney graft survival. Clin Exp Immunol 153(1): 117-126.

Li K, Wang N, Peng Q, Lu B, Ma L, Lambris J D, Sacks S, Zhou W (2012) C5a/C5aR signaling is an important negative regulator of murine nature killer cell homeostasis and effector function. Immunobiology 217(11): 1146

Makrides S C. (1998) Therapeutic inhibition of the complement system. Pharmacol Rev 50(1):59-87.

Manderson A P, Botto M, Walport M J. (2004) The role of complement in the development of systemic lupus erythematosus. Annu Rev Immunol 22: 431-456

Markiewski M M, DeAngelis R A, Benencia F, Ricklin-Lichtsteiner S K, Koutoulaki A, Gerard C, Coukos G, Lambris J D (2008) Modulation of the antitumor immune response by complement. Nat Immunol.(11): 1225-35

McGinnis S, Madden T L (2004) BLAST: at the core of a powerful and diverse set of sequence analysis tools. Nucleic Acids Res. 32(Web Server issue):W20-5.

Min X, Wei L, Li Z, Sacks S, Zhou W, Li K (2012) Negative regulation of human nature killer cells by complement. Immunobiology 217(11): 1189

Muller-Ladner U, Jones J L, Wetsel R A, Gay S, Raine C S, Barnum S R. (1996) Enhanced expression of chemotactic receptors in multiple sclerosis lesions. J Neurol Sci 144 (1-2):135-141.

Needleman & Wunsch (1970) A general method applicable to the search for similarities in the amino acid sequence of two proteins. J Mol Biol. 48(3):443-53.

Nozaki M, Raisler B J, Sakurai E, Sarma J V, Barnum S R, Lambris J D, Chen Y, Zhang K, Ambati B K, Baffi J Z, Ambati J. (2006) Drusen complement components C3a and C5a promote choroidal neovascularization. Proc Natl Acad Sci USA 103(7): 2328-2333 Ostrand-Rosenberg S (2008) Cancer and complement. Nat Biotechnol. 26(12): 1348-9.

Patel S N, Berghout J, Lovegrove F E, Ayi K, Conroy A, Serghides L, Min-oo G, Gowda D C, Sarma J V, Rittirsch D, Ward P A, Liles W C, Gros P, Kain K C (2008) C5 deficiency and C5a or C5aR blockade protects against cerebral malaria. J Exp Med 205(5): 1133-1143

Pearson & Lipman (1988) Improved tools for biological sequence comparison. Proc. Nat'l. Acad. Sci. USA 85: 2444

Piccolo M T, Wang Y, Sannomiya P, Piccolo N S, Piccolo M S, Hugh T E, Ward P A, Till G O. (1999) Chemotactic mediator requirements in lung injury following skin burns in rats. Exp Mol Pathol 66(3):220-226.

Ricklin D, Lambris J D. (2007) Complement-targeted therapeutics. Nat Biotechnol 25(11): 1265-1275

Riley R D, Sato H, Zhao Z Q, Thourani V H, Jordan J E, Fernandez A X, Ma X L, Hite D R, Rigel D F, Pellas T C, Peppard J, Bill K A, Lappe R W, Vinten-Johansen J. (2000) Recombinant human complement C5a receptor antagonist reduces infarct size after surgical revascularization. J Thorac Cardiovasc Surg 120(2):350-358.

Rittirsch D, Flierl M A, Nadeau B A, Day D E, Huber-Lang M, Mackay C R, Zetoune F S, Gerard N P, Cianflone K, Kohl J, Gerard C, Sarma J V, Ward P A (2008) Functional roles for C5a receptors in sepsis. Nat Med 14(5): 551-557

Sim R B, Laich A. (2000) Serine proteases of the complement system. Biochem Soc Trans 28(5):545-550.

Smith & Waterman (1981) Adv. Appl. Math. 2: 482

Sprong T, Brandtzaeg P, Fung M, Pharo A M, Hoiby E A, Michaelsen T E, Aase A, van der Meer J W, van Deuren M, Mollnes T E (2003) Inhibition of C5a-induced inflammation with preserved C5b-9-mediated bactericidal activity in a human whole blood model of meningococcal sepsis. Blood 102(10): 3702-3710

Tokodai K, Goto M, Inagaki A, Nakanishi W, Ogawa N, Satoh K, Kawagishi N, Sekiguchi S, Nilsson B, Okada N, Okada H, Satomi S (2010) Attenuation of cross-talk between the complement and coagulation cascades by C5a blockade improves early outcomes after intraportal islet transplantation. Transplantation 90(12): 1358-1365 van der Pals J, Koul S, Andersson P, Gotberg M, Ubachs J F, Kanski M, Arheden H, Olivecrona G K, Larsson B, Erlinge D (2010) Treatment with the C5a receptor antagonist ADC-1004 reduces myocardial infarction in a porcine ischemia-reperfusion model. BMC Cardiovasc Disord 10:45

Venkatesan N, Kim S J, Kim B H (2003) Novel phosphoramidite building blocks in synthesis and applications toward modified oligonucleotides. Curr Med Chem 10(19): 1973-1991

Wagner E, Frank M M (2010) Therapeutic potential of complement modulation. Nat Rev Drug Discov 9(1): 43-56

Walport M J. (2001a) Complement. First of two parts. N Engl J Med 344(14):1058-1066.

Walport M J. (2001b) Complement. Second of two parts. N Engl J Med 344(15):1140-1144.

Wang Y. (2006) Complementary therapies for inflammation. Nat Biotechnol 24(10): 1224-1226

Ward P A (2010a) The harmful role of c5a on innate immunity in sepsis. J Innate Immun 2(5): 439-445

Ward P A (2010b) Role of C5 activation products in sepsis. ScientificWorldJournal 10: 2395-2402

Wincott F, DiRenzo A, Shaffer C, Grimm S, Tracz D, Workman C, Sweedler D, Gonzalez C, Scaringe S, and Usman N (1995). Synthesis, deprotection, analysis and purification of RNA and ribosomes. Nucleic Acids Res. 23:2677-2684.

Woodruff T M, Arumugam T V, Shiels I A, Reid R C, Fairlie D P, Taylor S M. (2003) A potent human C5a receptor antagonist protects against disease pathology in a rat model of inflammatory bowel disease. J Immunol 171 (10):5514-5520.

Woodruff T M, Strachan A J, Dryburgh N, Shiels I A, Reid R C, Fairlie D P, Taylor S M. (2002) Antiarthritic activity of an orally active C5a receptor antagonist against antigen-induced monarticular arthritis in the rat. Arthritis Rheum 46(9):2476-2485.

Yao Y M, Redl H, Bahrami S, Schlag G. (1998) The inflammatory basis of trauma/shock-associated multiple organ failure. Inflamm Res 47(5): 201-210.

Zheng X, Zhang X, Feng B, Sun H, Suzuki M, Ichim T, Kubo N, Wong A, Min L R, Budohn M E, Garcia B, Jevnikar A M, Min W P (2008) Gene silencing of complement C5a receptor using siRNA for preventing ischemia/ reperfusion injury. Am J Pathol 173(4): 973-980

The features of the present invention disclosed in the specification, the claims, the sequence listing and/or the drawings may both separately and in any combination thereof be material for realizing the invention in various forms thereof

The invention claimed is:

1. A method comprising administering to a subject with a fibrotic disease, an inflammatory disease of the skin and/or an autoimmune disease of the skin, a nucleic acid molecule that binds human C5a, wherein the nucleic acid molecule comprises a 5'-terminal nucleotide, a central stretch of nucleotides and a 3'-terminal nucleotide, wherein the central stretch of nucleotides comprises a nucleotide sequence of 5' AUG$n_1$GGUGKU$n_2n_3$RGGGHUGUKGGG$n_4$G$n_5$CGACGC 3' (SEQ ID NO:61), wherein $n_1$ is U or dU, $n_2$ is G or dG, $n_3$ is A or dA, $n_4$ is U or dU, $n_5$ is U or dU, and G, A, U, C, H, K, and R are ribonucleotides, and dU, dG and dA are 2'-deoxyribonucleotides.

2. The method of claim 1, wherein the central stretch of nucleotides consists of ribonucleotides and 2'-deoxyribonucleotides.

3. The method of claim 1, wherein the nucleic acid molecule comprises in 5'→3' direction, a first terminal stretch of nucleotides, the central stretch of nucleotides and a second terminal stretch of nucleotides, wherein
the first terminal stretch of nucleotides comprises one to five nucleotides, and
the second terminal stretch of nucleotides comprises one to five nucleotides.

4. The method of claim 1, wherein the nucleic acid molecule binds human C5a and mouse C5a.

5. The method of claim 1, wherein the nucleic acid molecule comprises at least one binding moiety which binds human C5a and mouse C5a, wherein such binding moiety consists of L-nucleotides.

6. The method of claim 1, wherein the nucleic acid molecule is an L-nucleic acid molecule.

7. The method of claim 1, wherein the nucleic acid molecule is an antagonist of an activity mediated by human and/or mouse C5a.

8. The method of claim 1, wherein the nucleic acid molecule comprises a modification group.

9. The method of claim 8, wherein the modification group is polyethylene glycol, linear polyethylene glycol, branched polyethylene glycol, hydroxyethyl starch, a peptide, a protein, a polysaccharide, a sterol, polyoxypropylene, polyoxyamidate or poly (2-hydroxyethyl)-L-glutamine.

10. The method of claim 9, wherein said linear polyethylene glycol or said branched polyethylene glycol comprises a molecular weight of from about 20,000 to about 120,000 Da, from about 30,000 to about 80,000 Da or about 40,000 Da.

11. The method of claim 9, wherein said hydroxyethyl starch comprises a molecular weight of from about 50 to about 1000 kDa, from about 100 to about 700 kDa or from 200 to 500 kDa.

12. The method of claim 8, wherein said modification group is coupled to the nucleic acid molecule via a linker.

13. The method of claim 8, wherein the modification group is coupled to the 5'-terminal nucleotide and/or the 3'-terminal nucleotide of the nucleic acid molecule and/or to a nucleotide of the nucleic acid molecule between the 5'-terminal nucleotide of the nucleic acid molecule and the 3'-terminal nucleotide of the nucleic acid molecule.

14. The method of claim 1, wherein said subject is an animal or a human.

15. The method of claim 1, wherein said fibrotic disease comprises fibrosis of the lung, renal fibrosis, hepatic fibrosis and/or fibrosis after reperfusion injury or infarction of an organ.

16. The method of claim 15, wherein said fibrosis of the lung comprises idiopathic pulmonary fibrosis.

17. The method of claim 15, wherein said organ comprises heart, spleen, bladder, pancreas, stomach, lung, liver, kidney, limbs, brain or skeletal muscle.

18. The method of claim 1, wherein said inflammatory a disease of the skin and/or said autoimmune disease of the skin comprises psoriasis, urticaria, dermatomyositis, pemphigus vulgaris, pemphigus *foliaceus*, bullous pemphigoid, morphea/linear scleroderma, vitiligo, dermatitis herpetiformis, Duhring's disease, lichen sclerosis, diffuse scleroderma, systemic lupus erythematosus and manifestations thereof, diffuse scleroderma, ocular pemphigoid, keratoconjunctivitis, Stevens-Johnson syndrome, CREST syndrome, Morphea/linear scleroderma, conjunctivitis or vernal conjunctivitis.

19. The method of claim 1, wherein said inflammatory disease of the skin comprises damage of a transplanted skin, damage of skin to be transplanted or rejection of transplanted skin.

20. The method of claim 1, wherein said inflammatory disease of the skin comprises inflamed regional skin lesions.

21. The method of claim 1, wherein the method is to alleviate a symptom of said fibrotic disease, said inflammatory disease of the skin and/or said autoimmune disease of the skin.

22. The method of claim 1, wherein said fibrotic disease comprises acute respiratory distress syndrome, inflammatory bowel disease, Crohn's disease, colitis ulcerosa, Rheumatoid arthritis, ankylosing spondylitis, primary biliary cirrhosis, pancreatitis, psoriatic arthritis, sarcoidosis, Sjögren's Syndrome, and/or scleroderma.

\* \* \* \* \*

```
                        SEQUENCE LISTING

Sequence total quantity: 94
SEQ ID NO: 1            moltype = RNA   length = 44
FEATURE                 Location/Qualifiers
misc_feature            1..44
                        note = Synthetic
misc_feature            1..44
                        note = L-nucleic acid
source                  1..44
                        mol_type = other RNA
                        organism = synthetic construct
SEQUENCE: 1
gcctgatgtg gtgttgaagg gttgtggggt gtcgacgcac aggc                   44

SEQ ID NO: 2            moltype = RNA   length = 44
FEATURE                 Location/Qualifiers
misc_feature            1..44
                        note = Synthetic
misc_feature            1..44
                        note = L-nucleic acid
source                  1..44
                        mol_type = other RNA
                        organism = synthetic construct
SEQUENCE: 2
gcctgatgtg gtgttgaggg gttgtggggt gtcgacgcac aggc                   44

SEQ ID NO: 3            moltype = RNA   length = 44
FEATURE                 Location/Qualifiers
misc_feature            1..44
                        note = Synthetic
misc_feature            1..44
                        note = L-nucleic acid
source                  1..44
                        mol_type = other RNA
                        organism = synthetic construct
SEQUENCE: 3
gcctgatgtg gtgttgaagg gttgtgggt gtcgacgcac aggc                    44

SEQ ID NO: 4            moltype = RNA   length = 44
FEATURE                 Location/Qualifiers
misc_feature            1..44
                        note = Synthetic
misc_feature            1..44
                        note = L-nucleic acid
source                  1..44
                        mol_type = other RNA
                        organism = synthetic construct
SEQUENCE: 4
gcctgatgtg gtggtgaagg gttgttgggt gtcgacgcac aggc                   44

SEQ ID NO: 5            moltype = RNA   length = 44
FEATURE                 Location/Qualifiers
```

```
misc_feature              1..44
                          note = Synthetic
misc_feature              1..44
                          note = L-nucleic acid
source                    1..44
                          mol_type = other RNA
                          organism = synthetic construct
SEQUENCE: 5
gcctgatgtg gtggtgaggg gttgtggggt gtcgacgcac aggc          44

SEQ ID NO: 6              moltype = RNA  length = 44
FEATURE                   Location/Qualifiers
misc_feature              1..44
                          note = Synthetic
misc_feature              1..44
                          note = L-nucleic acid
source                    1..44
                          mol_type = other RNA
                          organism = synthetic construct
SEQUENCE: 6
gcctgatgtg gtggtgaggg gatgtggggt gtcgacgcac aggc          44

SEQ ID NO: 7              moltype = RNA  length = 44
FEATURE                   Location/Qualifiers
misc_feature              1..44
                          note = Synthetic
misc_feature              1..44
                          note = L-nucleic acid
source                    1..44
                          mol_type = other RNA
                          organism = synthetic construct
SEQUENCE: 7
gcctgatgtg gtgttgaggg gctgtggggt gtcgacgcac aggc          44

SEQ ID NO: 8              moltype = DNA  length = 44
FEATURE                   Location/Qualifiers
misc_feature              1..44
                          note = Synthetic
misc_feature              1..44
                          note = L-nucleic acid
misc_feature              1..8
                          note = RNA
misc_feature              9
                          note = DNA
misc_feature              10..44
                          note = RNA
source                    1..44
                          mol_type = other DNA
                          organism = synthetic construct
SEQUENCE: 8
gcctgatgtg gtggtgaagg gttgttgggt gtcgacgcac aggc          44

SEQ ID NO: 9              moltype = DNA  length = 44
FEATURE                   Location/Qualifiers
misc_feature              1..44
                          note = Synthetic
misc_feature              1..44
                          note = L-nucleic acid
misc_feature              1..15
                          note = RNA
misc_feature              16
                          note = DNA
misc_feature              17..44
                          note = RNA
source                    1..44
                          mol_type = other DNA
                          organism = synthetic construct
SEQUENCE: 9
gcctgatgtg gtggtgaagg gttgttgggt gtcgacgcac aggc          44

SEQ ID NO: 10             moltype = DNA  length = 44
FEATURE                   Location/Qualifiers
misc_feature              1..44
                          note = Synthetic
misc_feature              1..44
                          note = L-nucleic acid
misc_feature              1..16
                          note = RNA
misc_feature              17
```

```
                          note = DNA
misc_feature              18..44
                          note = RNA
source                    1..44
                          mol_type = other DNA
                          organism = synthetic construct
SEQUENCE: 10
gcctgatgtg gtggtgaagg gttgttgggt gtcgacgcac aggc            44

SEQ ID NO: 11             moltype = DNA   length = 44
FEATURE                   Location/Qualifiers
misc_feature              1..44
                          note = Synthetic
misc_feature              1..44
                          note = L-nucleic acid
misc_feature              1..29
                          note = RNA
misc_feature              30
                          note = DNA
misc_feature              31..44
                          note = RNA
source                    1..44
                          mol_type = other DNA
                          organism = synthetic construct
SEQUENCE: 11
gcctgatgtg gtggtgaagg gttgttgggt gtcgacgcac aggc            44

SEQ ID NO: 12             moltype = DNA   length = 44
FEATURE                   Location/Qualifiers
misc_feature              1..44
                          note = Synthetic
misc_feature              1..44
                          note = L-nucleic acid
misc_feature              1..31
                          note = RNA
misc_feature              32
                          note = DNA
misc_feature              33..44
                          note = RNA
source                    1..44
                          mol_type = other DNA
                          organism = synthetic construct
SEQUENCE: 12
gcctgatgtg gtggtgaagg gttgttgggt gtcgacgcac aggc            44

SEQ ID NO: 13             moltype = DNA   length = 44
FEATURE                   Location/Qualifiers
misc_feature              1..44
                          note = Synthetic
misc_feature              1..44
                          note = L-nucleic acid
misc_feature              1..39
                          note = RNA
misc_feature              40
                          note = DNA
misc_feature              41..44
                          note = RNA
source                    1..44
                          mol_type = other DNA
                          organism = synthetic construct
SEQUENCE: 13
gcctgatgtg gtggtgaagg gttgttgggt gtcgacgcac aggc            44

SEQ ID NO: 14             moltype = DNA   length = 44
FEATURE                   Location/Qualifiers
misc_feature              1..44
                          note = Synthetic
misc_feature              1..44
                          note = L-nucleic acid
misc_feature              1..8
                          note = RNA
misc_feature              9
                          note = DNA
misc_feature              10..29
                          note = RNA
misc_feature              30
                          note = DNA
misc_feature              31..44
                          note = RNA
```

```
source                  1..44
                        mol_type = other DNA
                        organism = synthetic construct
SEQUENCE: 14
gcctgatgtg gtggtgaagg gttgttgggt gtcgacgcac aggc                          44

SEQ ID NO: 15           moltype = DNA   length = 44
FEATURE                 Location/Qualifiers
misc_feature            1..44
                        note = Synthetic
misc_feature            1..44
                        note = L-nucleic acid
misc_feature            1..8
                        note = RNA
misc_feature            9
                        note = DNA
misc_feature            10..31
                        note = RNA
misc_feature            32
                        note = DNA
misc_feature            33..44
                        note = RNA
source                  1..44
                        mol_type = other DNA
                        organism = synthetic construct
SEQUENCE: 15
gcctgatgtg gtggtgaagg gttgttgggt gtcgacgcac aggc                          44

SEQ ID NO: 16           moltype = DNA   length = 44
FEATURE                 Location/Qualifiers
misc_feature            1..44
                        note = Synthetic
misc_feature            1..44
                        note = L-nucleic acid
misc_feature            1..8
                        note = RNA
misc_feature            9
                        note = DNA
misc_feature            10..39
                        note = RNA
misc_feature            40
                        note = DNA
misc_feature            41..44
                        note = RNA
source                  1..44
                        mol_type = other DNA
                        organism = synthetic construct
SEQUENCE: 16
gcctgatgtg gtggtgaagg gttgttgggt gtcgacgcac aggc                          44

SEQ ID NO: 17           moltype = DNA   length = 44
FEATURE                 Location/Qualifiers
misc_feature            1..44
                        note = Synthetic
misc_feature            1..44
                        note = L-nucleic acid
misc_feature            1..29
                        note = RNA
misc_feature            30
                        note = DNA
misc_feature            31
                        note = RNA
misc_feature            32
                        note = DNA
misc_feature            33..44
                        note = RNA
source                  1..44
                        mol_type = other DNA
                        organism = synthetic construct
SEQUENCE: 17
gcctgatgtg gtggtgaagg gttgttgggt gtcgacgcac aggc                          44

SEQ ID NO: 18           moltype = DNA   length = 44
FEATURE                 Location/Qualifiers
misc_feature            1..44
                        note = Synthetic
misc_feature            1..44
                        note = L-nucleic acid
misc_feature            1..29
```

```
                          note = RNA
misc_feature              30
                          note = DNA
misc_feature              31..39
                          note = RNA
misc_feature              40
                          note = DNA
misc_feature              41..44
                          note = RNA
source                    1..44
                          mol_type = other DNA
                          organism = synthetic construct
SEQUENCE: 18
gcctgatgtg gtggtgaagg gttgttgggt gtcgacgcac aggc              44

SEQ ID NO: 19             moltype = DNA  length = 44
FEATURE                   Location/Qualifiers
misc_feature              1..44
                          note = Synthetic
misc_feature              1..44
                          note = L-nucleic acid
misc_feature              1..31
                          note = RNA
misc_feature              32
                          note = DNA
misc_feature              33..39
                          note = RNA
misc_feature              40
                          note = DNA
misc_feature              41..44
                          note = RNA
source                    1..44
                          mol_type = other DNA
                          organism = synthetic construct
SEQUENCE: 19
gcctgatgtg gtggtgaagg gttgttgggt gtcgacgcac aggc              44

SEQ ID NO: 20             moltype = DNA  length = 44
FEATURE                   Location/Qualifiers
misc_feature              1..44
                          note = Synthetic
misc_feature              1..44
                          note = L-nucleic acid
misc_feature              1..8
                          note = RNA
misc_feature              9
                          note = DNA
misc_feature              10..29
                          note = RNA
misc_feature              30
                          note = DNA
misc_feature              31
                          note = RNA
misc_feature              32
                          note = DNA
misc_feature              33..44
                          note = RNA
source                    1..44
                          mol_type = other DNA
                          organism = synthetic construct
SEQUENCE: 20
gcctgatgtg gtggtgaagg gttgttgggt gtcgacgcac aggc              44

SEQ ID NO: 21             moltype = DNA  length = 44
FEATURE                   Location/Qualifiers
misc_feature              1..44
                          note = Synthetic
misc_feature              1..44
                          note = L-nucleic acid
misc_feature              1..8
                          note = RNA
misc_feature              9
                          note = DNA
misc_feature              10..29
                          note = RNA
misc_feature              30
                          note = DNA
misc_feature              31..39
                          note = RNA
```

```
                    misc_feature           40
                                           note = DNA
                    misc_feature           41..44
                                           note = RNA
                    source                 1..44
                                           mol_type = other DNA
                                           organism = synthetic construct
SEQUENCE: 21
gcctgatgtg gtggtgaagg gttgttgggt gtcgacgcac aggc                          44

SEQ ID NO: 22          moltype = DNA  length = 44
                    FEATURE                Location/Qualifiers
                    misc_feature           1..44
                                           note = Synthetic
                    misc_feature           1..44
                                           note = L-nucleic acid
                    misc_feature           1..8
                                           note = RNA
                    misc_feature           9
                                           note = DNA
                    misc_feature           10..31
                                           note = RNA
                    misc_feature           32
                                           note = DNA
                    misc_feature           33..39
                                           note = RNA
                    misc_feature           40
                                           note = DNA
                    misc_feature           41..44
                                           note = RNA
                    source                 1..44
                                           mol_type = other DNA
                                           organism = synthetic construct
SEQUENCE: 22
gcctgatgtg gtggtgaagg gttgttgggt gtcgacgcac aggc                          44

SEQ ID NO: 23          moltype = DNA  length = 44
                    FEATURE                Location/Qualifiers
                    misc_feature           1..44
                                           note = Synthetic
                    misc_feature           1..44
                                           note = L-nucleic acid
                    misc_feature           1..29
                                           note = RNA
                    misc_feature           30
                                           note = DNA
                    misc_feature           31
                                           note = RNA
                    misc_feature           32
                                           note = DNA
                    misc_feature           33..39
                                           note = RNA
                    misc_feature           40
                                           note = DNA
                    misc_feature           41..44
                                           note = RNA
                    source                 1..44
                                           mol_type = other DNA
                                           organism = synthetic construct
SEQUENCE: 23
gcctgatgtg gtggtgaagg gttgttgggt gtcgacgcac aggc                          44

SEQ ID NO: 24          moltype = DNA  length = 44
                    FEATURE                Location/Qualifiers
                    misc_feature           1..44
                                           note = Synthetic
                    misc_feature           1..44
                                           note = L-nucleic acid
                    misc_feature           1..8
                                           note = RNA
                    misc_feature           9
                                           note = DNA
                    misc_feature           10..29
                                           note = RNA
                    misc_feature           30
                                           note = DNA
                    misc_feature           31
                                           note = RNA
                    misc_feature           32
```

```
                        note = DNA
misc_feature            33..39
                        note = RNA
misc_feature            40
                        note = DNA
misc_feature            41..44
                        note = RNA
source                  1..44
                        mol_type = other DNA
                        organism = synthetic construct
SEQUENCE: 24
gcctgatgtg gtggtgaagg gttgttgggt gtcgacgcac aggc              44

SEQ ID NO: 25           moltype = DNA  length = 44
FEATURE                 Location/Qualifiers
misc_feature            1..44
                        note = Synthetic
misc_feature            1..44
                        note = L-nucleic acid
misc_feature            1..8
                        note = RNA
misc_feature            9
                        note = DNA
misc_feature            10..15
                        note = RNA
misc_feature            16
                        note = DNA
misc_feature            17..29
                        note = RNA
misc_feature            30
                        note = DNA
misc_feature            31
                        note = RNA
misc_feature            32
                        note = DNA
misc_feature            33..39
                        note = RNA
misc_feature            40
                        note = DNA
misc_feature            41..44
                        note = RNA
source                  1..44
                        mol_type = other DNA
                        organism = synthetic construct
SEQUENCE: 25
gcctgatgtg gtggtgaagg gttgttgggt gtcgacgcac aggc              44

SEQ ID NO: 26           moltype = DNA  length = 44
FEATURE                 Location/Qualifiers
misc_feature            1..44
                        note = Synthetic
misc_feature            1..44
                        note = L-nucleic acid
misc_feature            1..8
                        note = RNA
misc_feature            9
                        note = DNA
misc_feature            10..16
                        note = RNA
misc_feature            17
                        note = DNA
misc_feature            18..29
                        note = RNA
misc_feature            30
                        note = DNA
misc_feature            31
                        note = RNA
misc_feature            32
                        note = DNA
misc_feature            33..39
                        note = RNA
misc_feature            40
                        note = DNA
misc_feature            41..44
                        note = RNA
source                  1..44
                        mol_type = other DNA
                        organism = synthetic construct
SEQUENCE: 26
```

```
gcctgatgtg gtggtgaagg gttgttgggt gtcgacgcac aggc                      44

SEQ ID NO: 27           moltype = DNA   length = 44
FEATURE                 Location/Qualifiers
misc_feature            1..44
                        note = Synthetic
misc_feature            1..44
                        note = L-nucleic acid
misc_feature            1..8
                        note = RNA
misc_feature            9
                        note = DNA
misc_feature            10..15
                        note = RNA
misc_feature            16
                        note = DNA
misc_feature            17
                        note = DNA
misc_feature            18..29
                        note = RNA
misc_feature            30
                        note = DNA
misc_feature            31
                        note = RNA
misc_feature            32
                        note = DNA
misc_feature            33..39
                        note = RNA
misc_feature            40
                        note = DNA
misc_feature            41..44
                        note = RNA
source                  1..44
                        mol_type = other DNA
                        organism = synthetic construct
SEQUENCE: 27
gcctgatgtg gtggtgaagg gttgttgggt gtcgacgcac aggc                      44

SEQ ID NO: 28           moltype = DNA   length = 43
FEATURE                 Location/Qualifiers
misc_feature            1..43
                        note = Synthetic
misc_feature            1..43
                        note = L-nucleic acid
misc_feature            1..7
                        note = RNA
misc_feature            8
                        note = DNA
misc_feature            9..14
                        note = RNA
misc_feature            15
                        note = DNA
misc_feature            16
                        note = DNA
misc_feature            17..28
                        note = RNA
misc_feature            29
                        note = DNA
misc_feature            30
                        note = RNA
misc_feature            31
                        note = DNA
misc_feature            32..38
                        note = RNA
misc_feature            39
                        note = DNA
misc_feature            40..43
                        note = RNA
source                  1..43
                        mol_type = other DNA
                        organism = synthetic construct
SEQUENCE: 28
cctgatgtgg tggtgaaggg ttgttgggtg tcgacgcaca ggc                       43

SEQ ID NO: 29           moltype = DNA   length = 42
FEATURE                 Location/Qualifiers
misc_feature            1..42
                        note = Synthetic
misc_feature            1..42
```

```
                        note = L-nucleic acid
misc_feature            1..6
                        note = RNA
misc_feature            7
                        note = DNA
misc_feature            8..13
                        note = RNA
misc_feature            14
                        note = DNA
misc_feature            15
                        note = DNA
misc_feature            16..27
                        note = RNA
misc_feature            28
                        note = DNA
misc_feature            29
                        note = RNA
misc_feature            30
                        note = DNA
misc_feature            31..37
                        note = RNA
misc_feature            38
                        note = DNA
misc_feature            39..42
                        note = RNA
source                  1..42
                        mol_type = other DNA
                        organism = synthetic construct
SEQUENCE: 29
ctgatgtggt ggtgaagggt tgttgggtgt cgacgcacag gc                    42

SEQ ID NO: 31           moltype = DNA   length = 41
FEATURE                 Location/Qualifiers
misc_feature            1..41
                        note = Synthetic
misc_feature            1..41
                        note = L-nucleic acid
misc_feature            1..5
                        note = RNA
misc_feature            6
                        note = DNA
misc_feature            7..12
                        note = RNA
misc_feature            13
                        note = DNA
misc_feature            14
                        note = DNA
misc_feature            15..26
                        note = RNA
misc_feature            27
                        note = DNA
misc_feature            28
                        note = RNA
misc_feature            29
                        note = DNA
misc_feature            30..36
                        note = RNA
misc_feature            37
                        note = DNA
misc_feature            38..41
                        note = RNA
source                  1..41
                        mol_type = other DNA
                        organism = synthetic construct
SEQUENCE: 30
tgatgtggtg gtgaagggtt gttgggtgtc gacgcacagg c                      41

SEQ ID NO: 31           moltype = DNA   length = 40
FEATURE                 Location/Qualifiers
misc_feature            1..40
                        note = Synthetic
misc_feature            1..40
                        note = L-nucleic acid
misc_feature            1..4
                        note = RNA
misc_feature            5
                        note = DNA
misc_feature            6..11
                        note = RNA
```

```
misc_feature            12
                        note = DNA
misc_feature            13
                        note = DNA
misc_feature            14..25
                        note = RNA
misc_feature            26
                        note = DNA
misc_feature            27
                        note = RNA
misc_feature            28
                        note = DNA
misc_feature            29..35
                        note = RNA
misc_feature            36
                        note = DNA
misc_feature            37..40
                        note = RNA
source                  1..40
                        mol_type = other DNA
                        organism = synthetic construct
SEQUENCE: 31
gatgtggtgg tgaagggttg ttgggtgtcg acgcacaggc                              40

SEQ ID NO: 32           moltype = DNA   length = 42
FEATURE                 Location/Qualifiers
misc_feature            1..42
                        note = Synthetic
misc_feature            1..42
                        note = L-nucleic acid
misc_feature            1..7
                        note = RNA
misc_feature            8
                        note = DNA
misc_feature            9..14
                        note = RNA
misc_feature            15
                        note = DNA
misc_feature            16
                        note = DNA
misc_feature            17..28
                        note = RNA
misc_feature            29
                        note = DNA
misc_feature            30
                        note = RNA
misc_feature            31
                        note = DNA
misc_feature            32..38
                        note = RNA
misc_feature            39
                        note = DNA
misc_feature            40..42
                        note = RNA
source                  1..42
                        mol_type = other DNA
                        organism = synthetic construct
SEQUENCE: 32
gctgatgtgt tggtgaaggg ttgttgggtg tcgacgcaca gc                           42

SEQ ID NO: 33           moltype = DNA   length = 40
FEATURE                 Location/Qualifiers
misc_feature            1..40
                        note = Synthetic
misc_feature            1..40
                        note = L-nucleic acid
misc_feature            1..6
                        note = RNA
misc_feature            7
                        note = DNA
misc_feature            8..13
                        note = RNA
misc_feature            14
                        note = DNA
misc_feature            15
                        note = DNA
misc_feature            16..27
                        note = RNA
misc_feature            28
```

```
                       note = DNA
misc_feature           29
                       note = RNA
misc_feature           30
                       note = DNA
misc_feature           31..37
                       note = RNA
misc_feature           38
                       note = DNA
misc_feature           39..40
                       note = RNA
source                 1..40
                       mol_type = other DNA
                       organism = synthetic construct
SEQUENCE: 33
gtgatgtggt ggtgaagggt tgttgggtgt cgacgcacac                              40

SEQ ID NO: 34          moltype = DNA   length = 38
FEATURE                Location/Qualifiers
misc_feature           1..38
                       note = Synthetic
misc_feature           1..38
                       note = L-nucleic acid
misc_feature           1..5
                       note = RNA
misc_feature           6
                       note = DNA
misc_feature           7..12
                       note = RNA
misc_feature           13
                       note = DNA
misc_feature           14
                       note = DNA
misc_feature           15..26
                       note = RNA
misc_feature           27
                       note = DNA
misc_feature           28
                       note = RNA
misc_feature           29
                       note = DNA
misc_feature           30..36
                       note = RNA
misc_feature           37
                       note = DNA
misc_feature           38
                       note = RNA
source                 1..38
                       mol_type = other DNA
                       organism = synthetic construct
SEQUENCE: 34
tgatgtggtg gtgaagggtt gttgggtgtc gacgcaca                                38

SEQ ID NO: 35          moltype = DNA   length = 42
FEATURE                Location/Qualifiers
misc_feature           1..42
                       note = Synthetic
misc_feature           1..42
                       note = L-nucleic acid
misc_feature           1..7
                       note = RNA
misc_feature           8
                       note = DNA
misc_feature           9..14
                       note = RNA
misc_feature           15
                       note = DNA
misc_feature           16
                       note = DNA
misc_feature           17..28
                       note = RNA
misc_feature           29
                       note = DNA
misc_feature           30
                       note = RNA
misc_feature           31
                       note = DNA
misc_feature           32..38
                       note = RNA
```

|          |                              |
|----------|------------------------------|
| misc_feature | 39 |
|  | note = DNA |
| misc_feature | 40..42 |
|  | note = RNA |
| source | 1..42 |
|  | mol_type = other DNA |
|  | organism = synthetic construct |

SEQUENCE: 35
gccgatgtgg tggtgaaggg ttgttgggtg tcgacgcacg gc                42

| SEQ ID NO: 36 | moltype = DNA  length = 42 |
|---|---|
| FEATURE | Location/Qualifiers |
| misc_feature | 1..42 |
|  | note = Synthetic |
| misc_feature | 1..42 |
|  | note = L-nucleic acid |
| misc_feature | 1..7 |
|  | note = RNA |
| misc_feature | 8 |
|  | note = DNA |
| misc_feature | 9..14 |
|  | note = RNA |
| misc_feature | 15 |
|  | note = DNA |
| misc_feature | 16 |
|  | note = DNA |
| misc_feature | 17..28 |
|  | note = RNA |
| misc_feature | 29 |
|  | note = DNA |
| misc_feature | 30 |
|  | note = RNA |
| misc_feature | 31 |
|  | note = DNA |
| misc_feature | 32..38 |
|  | note = RNA |
| misc_feature | 39 |
|  | note = DNA |
| misc_feature | 40..42 |
|  | note = RNA |
| source | 1..42 |
|  | mol_type = other DNA |
|  | organism = synthetic construct |

SEQUENCE: 36
ggcgatgtgg tggtgaaggg ttgttgggtg tcgacgcacg cc                42

| SEQ ID NO: 37 | moltype = DNA  length = 40 |
|---|---|
| FEATURE | Location/Qualifiers |
| misc_feature | 1..40 |
|  | note = Synthetic |
| misc_feature | 1..40 |
|  | note = L-nucleic acid |
| misc_feature | 1..6 |
|  | note = RNA |
| misc_feature | 7 |
|  | note = DNA |
| misc_feature | 8..13 |
|  | note = RNA |
| misc_feature | 14 |
|  | note = DNA |
| misc_feature | 15 |
|  | note = DNA |
| misc_feature | 16..27 |
|  | note = RNA |
| misc_feature | 28 |
|  | note = DNA |
| misc_feature | 29 |
|  | note = RNA |
| misc_feature | 30 |
|  | note = DNA |
| misc_feature | 31..37 |
|  | note = RNA |
| misc_feature | 38 |
|  | note = DNA |
| misc_feature | 39..40 |
|  | note = RNA |
| source | 1..40 |
|  | mol_type = other DNA |
|  | organism = synthetic construct |

```
SEQUENCE: 37
gcgatgtggt ggtgaagggt tgttgggtgt cgacgcacgc                              40

SEQ ID NO: 38           moltype = DNA  length = 41
FEATURE                 Location/Qualifiers
misc_feature            1..41
                        note = Synthetic
misc_feature            1..41
                        note = L-nucleic acid
misc_feature            1..6
                        note = RNA
misc_feature            7
                        note = DNA
misc_feature            8..13
                        note = RNA
misc_feature            14
                        note = DNA
misc_feature            15
                        note = DNA
misc_feature            16..27
                        note = RNA
misc_feature            28
                        note = DNA
misc_feature            29
                        note = RNA
misc_feature            30
                        note = DNA
misc_feature            31..37
                        note = RNA
misc_feature            38
                        note = DNA
misc_feature            39..41
                        note = RNA
source                  1..41
                        mol_type = other DNA
                        organism = synthetic construct
SEQUENCE: 38
ctgatgtggt ggtgaagggt tgttgggtgt cgacgcacag c                            41

SEQ ID NO: 39           moltype = DNA  length = 40
FEATURE                 Location/Qualifiers
misc_feature            1..40
                        note = Synthetic
misc_feature            1..40
                        note = L-nucleic acid
misc_feature            1..5
                        note = RNA
misc_feature            6
                        note = DNA
misc_feature            7..12
                        note = RNA
misc_feature            13
                        note = DNA
misc_feature            14
                        note = DNA
misc_feature            15..26
                        note = RNA
misc_feature            27
                        note = DNA
misc_feature            28
                        note = RNA
misc_feature            29
                        note = DNA
misc_feature            30..36
                        note = RNA
misc_feature            37
                        note = DNA
misc_feature            38..40
                        note = RNA
source                  1..40
                        mol_type = other DNA
                        organism = synthetic construct
SEQUENCE: 39
tgatgtggtg gtgaagggtt gttgggtgtc gacgcacagc                              40

SEQ ID NO: 40           moltype = DNA  length = 40
FEATURE                 Location/Qualifiers
misc_feature            1..40
                        note = Synthetic
```

| | |
|---|---|
| misc_feature | 1..40 |
| | note = L-nucleic acid |
| misc_feature | 1..5 |
| | note = RNA |
| misc_feature | 6 |
| | note = DNA |
| misc_feature | 7..12 |
| | note = RNA |
| misc_feature | 13 |
| | note = DNA |
| misc_feature | 14 |
| | note = DNA |
| misc_feature | 15..26 |
| | note = RNA |
| misc_feature | 27 |
| | note = DNA |
| misc_feature | 28 |
| | note = RNA |
| misc_feature | 29 |
| | note = DNA |
| misc_feature | 30..36 |
| | note = RNA |
| misc_feature | 37 |
| | note = DNA |
| misc_feature | 38..40 |
| | note = RNA |
| source | 1..40 |
| | mol_type = other DNA |
| | organism = synthetic construct |

SEQUENCE: 40
cgatgtggtg gtgaagggtt gttgggtgtc gacgcacagc    40

| | |
|---|---|
| SEQ ID NO: 41 | moltype = DNA  length = 39 |
| FEATURE | Location/Qualifiers |
| misc_feature | 1..39 |
| | note = Synthetic |
| misc_feature | 1..39 |
| | note = L-nucleic acid |
| misc_feature | 1..4 |
| | note = RNA |
| misc_feature | 5 |
| | note = DNA |
| misc_feature | 6..11 |
| | note = RNA |
| misc_feature | 12 |
| | note = DNA |
| misc_feature | 13 |
| | note = DNA |
| misc_feature | 14..25 |
| | note = RNA |
| misc_feature | 26 |
| | note = DNA |
| misc_feature | 27 |
| | note = RNA |
| misc_feature | 28 |
| | note = DNA |
| misc_feature | 29..35 |
| | note = RNA |
| misc_feature | 36 |
| | note = DNA |
| misc_feature | 37..39 |
| | note = RNA |
| source | 1..39 |
| | mol_type = other DNA |
| | organism = synthetic construct |

SEQUENCE: 41
gatgtggtgg tgaagggttg ttgggtgtcg acgcacagc    39

| | |
|---|---|
| SEQ ID NO: 42 | moltype = DNA  length = 41 |
| FEATURE | Location/Qualifiers |
| misc_feature | 1..41 |
| | note = Synthetic |
| misc_feature | 1..41 |
| | note = L-nucleic acid |
| misc_feature | 1..7 |
| | note = RNA |
| misc_feature | 8 |
| | note = DNA |
| misc_feature | 9..14 |

```
misc_feature         note = RNA
                     15
                     note = DNA
misc_feature         16
                     note = DNA
misc_feature         17..28
                     note = RNA
misc_feature         29
                     note = DNA
misc_feature         30
                     note = RNA
misc_feature         31
                     note = DNA
misc_feature         32..38
                     note = RNA
misc_feature         39
                     note = DNA
misc_feature         40..41
                     note = RNA
source               1..41
                     mol_type = other DNA
                     organism = synthetic construct
SEQUENCE: 42
gctgatgtgg tggtgaaggg ttgttgggtg tcgacgcaca c                    41

SEQ ID NO: 43        moltype = DNA   length = 40
FEATURE              Location/Qualifiers
misc_feature         1..40
                     note = Synthetic
misc_feature         1..40
                     note = L-nucleic acid
misc_feature         1..7
                     note = RNA
misc_feature         8
                     note = DNA
misc_feature         9..14
                     note = RNA
misc_feature         15
                     note = DNA
misc_feature         16
                     note = DNA
misc_feature         17..28
                     note = RNA
misc_feature         29
                     note = DNA
misc_feature         30
                     note = RNA
misc_feature         31
                     note = DNA
misc_feature         32..38
                     note = RNA
misc_feature         39
                     note = DNA
misc_feature         40
                     note = RNA
source               1..40
                     mol_type = other DNA
                     organism = synthetic construct
SEQUENCE: 43
gctgatgtgg tggtgaaggg ttgttgggtg tcgacgcacc                      40

SEQ ID NO: 44        moltype = DNA   length = 40
FEATURE              Location/Qualifiers
misc_feature         1..40
                     note = Synthetic
misc_feature         1..40
                     note = L-nucleic acid
misc_feature         1..7
                     note = RNA
misc_feature         8
                     note = DNA
misc_feature         9..14
                     note = RNA
misc_feature         15
                     note = DNA
misc_feature         16
                     note = DNA
misc_feature         17..28
                     note = RNA
```

```
misc_feature        29
                    note = DNA
misc_feature        30
                    note = RNA
misc_feature        31
                    note = DNA
misc_feature        32..38
                    note = RNA
misc_feature        39
                    note = DNA
misc_feature        40
                    note = RNA
source              1..40
                    mol_type = other DNA
                    organism = synthetic construct
SEQUENCE: 44
gctgatgtgg tggtgaaggg ttgttgggtg tcgacgcaca                    40

SEQ ID NO: 45       moltype = DNA  length = 39
FEATURE             Location/Qualifiers
misc_feature        1..39
                    note = Synthetic
misc_feature        1..39
                    note = L-nucleic acid
misc_feature        1..5
                    note = RNA
misc_feature        6
                    note = DNA
misc_feature        7..12
                    note = RNA
misc_feature        13
                    note = DNA
misc_feature        14
                    note = DNA
misc_feature        15..26
                    note = RNA
misc_feature        27
                    note = DNA
misc_feature        28
                    note = RNA
misc_feature        29
                    note = DNA
misc_feature        30..36
                    note = RNA
misc_feature        37
                    note = DNA
misc_feature        38..39
                    note = RNA
source              1..39
                    mol_type = other DNA
                    organism = synthetic construct
SEQUENCE: 45
cgatgtggtg gtgaagggtt gttgggtgtc gacgcacgc                     39

SEQ ID NO: 46       moltype = DNA  length = 38
FEATURE             Location/Qualifiers
misc_feature        1..38
                    note = Synthetic
misc_feature        1..38
                    note = L-nucleic acid
misc_feature        1..4
                    note = RNA
misc_feature        5
                    note = DNA
misc_feature        6..11
                    note = RNA
misc_feature        12
                    note = DNA
misc_feature        13
                    note = DNA
misc_feature        14..25
                    note = RNA
misc_feature        26
                    note = DNA
misc_feature        27
                    note = RNA
misc_feature        28
                    note = DNA
misc_feature        29..35
```

```
                              note = RNA
misc_feature                  36
                              note = DNA
misc_feature                  37..38
                              note = RNA
source                        1..38
                              mol_type = other DNA
                              organism = synthetic construct
SEQUENCE: 46
gatgtggtgg tgaagggttg ttgggtgtcg acgcacgc                              38

SEQ ID NO: 47                 moltype = DNA   length = 39
FEATURE                       Location/Qualifiers
misc_feature                  1..39
                              note = Synthetic
misc_feature                  1..39
                              note = L-nucleic acid
misc_feature                  1..6
                              note = RNA
misc_feature                  7
                              note = DNA
misc_feature                  8..13
                              note = RNA
misc_feature                  14
                              note = DNA
misc_feature                  15
                              note = DNA
misc_feature                  16..27
                              note = RNA
misc_feature                  28
                              note = DNA
misc_feature                  29
                              note = RNA
misc_feature                  30
                              note = DNA
misc_feature                  31..37
                              note = RNA
misc_feature                  38
                              note = DNA
misc_feature                  39
                              note = RNA
source                        1..39
                              mol_type = other DNA
                              organism = synthetic construct
SEQUENCE: 47
gcgatgtggt ggtgaagggt tgttgggtgt cgacgcacc                             39

SEQ ID NO: 48                 moltype = DNA   length = 38
FEATURE                       Location/Qualifiers
misc_feature                  1..38
                              note = Synthetic
misc_feature                  1..38
                              note = L-nucleic acid
misc_feature                  1..6
                              note = RNA
misc_feature                  7
                              note = DNA
misc_feature                  8..13
                              note = RNA
misc_feature                  14
                              note = DNA
misc_feature                  15
                              note = DNA
misc_feature                  16..27
                              note = RNA
misc_feature                  28
                              note = DNA
misc_feature                  29
                              note = RNA
misc_feature                  30
                              note = DNA
misc_feature                  31..37
                              note = RNA
misc_feature                  38
                              note = DNA
source                        1..38
                              mol_type = other DNA
                              organism = synthetic construct
SEQUENCE: 48
```

```
gcgatgtggt ggtgaagggt tgttgggtgt cgacgcac                                    38

SEQ ID NO: 49           moltype = DNA   length = 38
FEATURE                 Location/Qualifiers
misc_feature            1..38
                        note = Synthetic
misc_feature            1..38
                        note = L-nucleic acid
misc_feature            1..5
                        note = RNA
misc_feature            6
                        note = DNA
misc_feature            7..12
                        note = RNA
misc_feature            13
                        note = DNA
misc_feature            14
                        note = DNA
misc_feature            15..26
                        note = RNA
misc_feature            27
                        note = DNA
misc_feature            28
                        note = RNA
misc_feature            29
                        note = DNA
misc_feature            30..36
                        note = RNA
misc_feature            37
                        note = DNA
misc_feature            38
                        note = RNA
source                  1..38
                        mol_type = other DNA
                        organism = synthetic construct
SEQUENCE: 49
ggatgtggtg gtgaagggtt gttgggtgtc gacgcacc                                    38

SEQ ID NO: 50           moltype = AA    length = 74
FEATURE                 Location/Qualifiers
source                  1..74
                        mol_type = protein
                        organism = Homo sapiens
SEQUENCE: 50
TLQKKIEEIA AKYKHSVVKK CCYDGACVNN DETCEQRAAR ISLGPRCIKA FTECCVVASQ            60
LRANISHKDM QLGR                                                              74

SEQ ID NO: 51           moltype = AA    length = 77
FEATURE                 Location/Qualifiers
source                  1..77
                        mol_type = protein
                        organism = Rattus norvegicus
SEQUENCE: 51
DLQLLHQKVE EQAAKYKHRV PKKCCYDGAR ENKYETCEQR VARVTIGPHC IRAFNECCTI            60
ADKIRKESHH KGMLLGR                                                           77

SEQ ID NO: 52           moltype = AA    length = 77
FEATURE                 Location/Qualifiers
source                  1..77
                        mol_type = protein
                        organism = Mus musculus
SEQUENCE: 52
NLHLLRQKIE EQAAKYKHSV PKKCCYDGAR VNFYETCEER VARVTIGPLC IRAFNECCTI            60
ANKIRKESPH KPVQLGR                                                           77

SEQ ID NO: 53           moltype = AA    length = 999
FEATURE                 Location/Qualifiers
source                  1..999
                        mol_type = protein
                        organism = Homo sapiens
SEQUENCE: 53
TLQKKIEEIA AKYKHSVVKK CCYDGACVNN DETCEQRAAR ISLGPRCIKA FTECCVVASQ            60
LRANISHKDM QLGRLHMKTL LPVSKPEIRS YFPESWLWEV HLVPRRKQLQ FALPDSLTTW           120
EIQGIGISNT GICVADTVKA KVFKDVFLEM NIPYSVVRGE QIQLKGTVYN YRTSGMQFCV           180
KMSAVEGICT SESPVIDHQG TKSSKCVRQK VEGSSSHLVT FTVLPLEIGL HNINFSLETW           240
FGKEILVKTL RVVPEGVKRE SYSGVTLDPR GIYGTISRRK EFPYRIPLDL VPKTEIKRIL           300
SVKGLLVGEI LSAVLSQEGI NILTHLPKGS AEAELMSVVP VFYVFHYLET GNHWNIFHSD           360
PLIEKQKLKK KLKEGMLSIM SYRNADYSYS VWKGGSASTW LTAFALRVLG QVNKYVEQNQ           420
NSICNSLLWL VENYQLDNGS FKENSYQPI  KLQGTLPVEA RENSLYLTAF TVIGIRKAFD           480
```

```
ICPLVKIDTA LIKADNFLLE NTLPAQSTFT LAISAYALSL GDKTHPQFRS IVSALKREAL   540
VKGNPPIYRF WKDNLQHKDS SVPNTGTARM VETTAYALLT SLNLKDINYV NPVIKWLSEE   600
QRYGGGFYST QDTINAIEGL TEYSLLVKQL RLSMDIDVSY KHKGALHNYK MTDKNFLGRP   660
VEVLLNDDLI VSTGFGSGLA TVHVTTVVHK TSTSEEVCSF YLKIDTQDIE ASHYRGYGNS   720
DYKRIVACAS YKPSREESSS GSSHAVMDIS LPTGISANEE DLKALVEGVD QLFTDYQIKD   780
GHVILQLNSI PSSDFLCVRF RIFELFEVGF LSPATFTVYE YHRPDKQCTM FYSTSNIKIQ   840
KVCEGAACKC VEADCGQMQE ELDLTISAET RKQTACKPEI AYAYKVSITS ITVENVFVKY   900
KATLLDIYKT GEAVAEKDSE ITFIKKVTCT NAELVKGRQY LIMGKEALQI KYNFSFRYIY   960
PLDSLTWIEY WPRDTTCSSC QAFLANLDEF AEDIFLNGC                         999

SEQ ID NO: 54           moltype = AA  length = 74
FEATURE                 Location/Qualifiers
source                  1..74
                        mol_type = protein
                        organism = Macaca mulatta
SEQUENCE: 54
MLQEKIEEIA AKYKHLVVKK CCYDGVRINH DETCEQRAAR ISVGPRCVKA FTECCVVASQ   60
LRANNSHKDL QLGR                                                    74

SEQ ID NO: 55           moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 55
gcgatgtggt ggtgaagggt tgttgggtgt cgacgcacgc                         40

SEQ ID NO: 56           moltype = DNA  length = 40
FEATURE                 Location/Qualifiers
misc_feature            1..40
                        note = Synthetic
misc_feature            1..40
                        note = L-nucleic acid
misc_feature            1..6
                        note = RNA
misc_feature            7
                        note = DNA
misc_feature            8..40
                        note = RNA
source                  1..40
                        mol_type = other DNA
                        organism = synthetic construct
SEQUENCE: 56
gcgatgtggt ggtgaagggt tgttgggtgt cgacgcacgc                         40

SEQ ID NO: 57           moltype = DNA  length = 40
FEATURE                 Location/Qualifiers
misc_feature            1..40
                        note = Synthetic
misc_feature            1..40
                        note = L-nucleic acid
misc_feature            1..6
                        note = RNA
misc_feature            7
                        note = DNA
misc_feature            8..27
                        note = RNA
misc_feature            28
                        note = DNA
misc_feature            29..40
                        note = RNA
source                  1..40
                        mol_type = other DNA
                        organism = synthetic construct
SEQUENCE: 57
gcgatgtggt ggtgaagggt tgttgggtgt cgacgcacgc                         40

SEQ ID NO: 58           moltype = DNA  length = 40
FEATURE                 Location/Qualifiers
misc_feature            1..40
                        note = Synthetic
misc_feature            1..40
                        note = L-nucleic acid
misc_feature            1..6
                        note = RNA
misc_feature            7
                        note = DNA
```

-continued

```
misc_feature            8..27
                        note = RNA
misc_feature            28
                        note = DNA
misc_feature            29
                        note = RNA
misc_feature            30
                        note = DNA
misc_feature            31..40
                        note = RNA
source                  1..40
                        mol_type = other DNA
                        organism = synthetic construct
SEQUENCE: 58
gcgatgtggt ggtgaagggt tgttgggtgt cgacgcacgc                        40

SEQ ID NO: 59           moltype = DNA   length = 40
FEATURE                 Location/Qualifiers
misc_feature            1..40
                        note = Synthetic
misc_feature            1..40
                        note = L-nucleic acid
misc_feature            1..6
                        note = RNA
misc_feature            7
                        note = DNA
misc_feature            8..27
                        note = RNA
misc_feature            28
                        note = DNA
misc_feature            29..37
                        note = RNA
misc_feature            38
                        note = DNA
misc_feature            39..40
                        note = RNA
source                  1..40
                        mol_type = other DNA
                        organism = synthetic construct
SEQUENCE: 59
gcgatgtggt ggtgaagggt tgttgggtgt cgacgcacgc                        40

SEQ ID NO: 60           moltype = DNA   length = 40
FEATURE                 Location/Qualifiers
misc_feature            1..40
                        note = Synthetic
misc_feature            1..40
                        note = L-nucleic acid
misc_feature            1..6
                        note = RNA
misc_feature            7
                        note = DNA
misc_feature            8..27
                        note = RNA
misc_feature            28
                        note = DNA
misc_feature            29
                        note = RNA
misc_feature            30
                        note = DNA
misc_feature            31..37
                        note = RNA
misc_feature            38
                        note = DNA
misc_feature            39..40
                        note = RNA
source                  1..40
                        mol_type = other DNA
                        organism = synthetic construct
SEQUENCE: 60
gcgatgtggt ggtgaagggt tgttgggtgt cgacgcacgc                        40

SEQ ID NO: 61           moltype = RNA   length = 34
FEATURE                 Location/Qualifiers
misc_feature            1..34
                        note = Synthetic
misc_feature            1..34
                        note = L-nucleic acid
variation               4
```

```
                        note = n is U or dU
variation               11
                        note = n is G or dG
variation               12
                        note = n is A or dA
variation               25
                        note = n is U or dU
variation               27
                        note = n is U or dU
source                  1..34
                        mol_type = other RNA
                        organism = synthetic construct
SEQUENCE: 61
atgnggtgkt nnrggghtgt kgggngncga cgca                                     34

SEQ ID NO: 62           moltype = RNA   length = 34
FEATURE                 Location/Qualifiers
misc_feature            1..34
                        note = Synthetic
misc_feature            1..34
                        note = L-nucleic acid
variation               4
                        note = n is U or dU
variation               11
                        note = n is G or dG
variation               12
                        note = n is A or dA
variation               25
                        note = n is U or dU
variation               27
                        note = n is U or dU
source                  1..34
                        mol_type = other RNA
                        organism = synthetic construct
SEQUENCE: 62
atgnggtgtt nnagggttgt ggggngncga cgca                                     34

SEQ ID NO: 63           moltype = RNA   length = 34
FEATURE                 Location/Qualifiers
misc_feature            1..34
                        note = Synthetic
misc_feature            1..34
                        note = L-nucleic acid
variation               4
                        note = n is U or dU
variation               11
                        note = n is G or dG
variation               12
                        note = n is A or dA
variation               25
                        note = n is U or dU
variation               27
                        note = n is U or dU
source                  1..34
                        mol_type = other RNA
                        organism = synthetic construct
SEQUENCE: 63
atgnggtgtt nngggggttgt ggggngncga cgca                                    34

SEQ ID NO: 64           moltype = RNA   length = 34
FEATURE                 Location/Qualifiers
misc_feature            1..34
                        note = Synthetic
misc_feature            1..34
                        note = L-nucleic acid
variation               4
                        note = n is U or dU
variation               11
                        note = n is G or dG
variation               12
                        note = n is A or dA
variation               25
                        note = n is U or dU
variation               27
                        note = n is U or dU
source                  1..34
                        mol_type = other RNA
                        organism = synthetic construct
SEQUENCE: 64
```

```
atgnggtgtt nnagggttgt tgggngncga cgca                                          34

SEQ ID NO: 65           moltype = RNA   length = 34
FEATURE                 Location/Qualifiers
misc_feature            1..34
                        note = Synthetic
misc_feature            1..34
                        note = L-nucleic acid
variation               4
                        note = n is U or dU
variation               11
                        note = n is G or dG
variation               12
                        note = n is A or dA
variation               25
                        note = n is U or dU
variation               27
                        note = n is U or dU
source                  1..34
                        mol_type = other RNA
                        organism = synthetic construct
SEQUENCE: 65
atgnggtggt nnagggttgt tgggngncga cgca                                          34

SEQ ID NO: 66           moltype = RNA   length = 34
FEATURE                 Location/Qualifiers
misc_feature            1..34
                        note = Synthetic
misc_feature            1..34
                        note = L-nucleic acid
variation               4
                        note = n is U or dU
variation               11
                        note = n is G or dG
variation               12
                        note = n is A or dA
variation               25
                        note = n is U or dU
variation               27
                        note = n is U or dU
source                  1..34
                        mol_type = other RNA
                        organism = synthetic construct
SEQUENCE: 66
atgnggtggt nngggttgt ggggngncga cgca                                           34

SEQ ID NO: 67           moltype = RNA   length = 34
FEATURE                 Location/Qualifiers
misc_feature            1..34
                        note = Synthetic
misc_feature            1..34
                        note = L-nucleic acid
variation               4
                        note = n is U or dU
variation               11
                        note = n is G or dG
variation               12
                        note = n is A or dA
variation               25
                        note = n is U or dU
variation               27
                        note = n is U or dU
source                  1..34
                        mol_type = other RNA
                        organism = synthetic construct
SEQUENCE: 67
atgnggtggt nngggatgt ggggngncga cgca                                           34

SEQ ID NO: 68           moltype = RNA   length = 34
FEATURE                 Location/Qualifiers
misc_feature            1..34
                        note = Synthetic
misc_feature            1..34
                        note = L-nucleic acid
variation               4
                        note = n is U or dU
variation               11
                        note = n is G or dG
variation               12
```

```
                        note = n is A or dA
variation               25
                        note = n is U or dU
variation               27
                        note = n is U or dU
source                  1..34
                        mol_type = other RNA
                        organism = synthetic construct
SEQUENCE: 68
atgnggtgtt nngggctgt ggggngncga cgca                                34

SEQ ID NO: 69           moltype = RNA   length = 34
FEATURE                 Location/Qualifiers
misc_feature            1..34
                        note = Synthetic
misc_feature            1..34
                        note = L-nucleic acid
source                  1..34
                        mol_type = other RNA
                        organism = synthetic construct
SEQUENCE: 69
atgtggtgkt gargghtgt kgggtgtcga cgca                                34

SEQ ID NO: 70           moltype = RNA   length = 34
FEATURE                 Location/Qualifiers
misc_feature            1..34
                        note = Synthetic
misc_feature            1..34
                        note = L-nucleic acid
source                  1..34
                        mol_type = other RNA
                        organism = synthetic construct
SEQUENCE: 70
atgtggtgtt gaagggttgt tgggtgtcga cgca                               34

SEQ ID NO: 71           moltype = RNA   length = 34
FEATURE                 Location/Qualifiers
misc_feature            1..34
                        note = Synthetic
misc_feature            1..34
                        note = L-nucleic acid
source                  1..34
                        mol_type = other RNA
                        organism = synthetic construct
SEQUENCE: 71
atgtggtggt gaagggttgt tgggtgtcga cgca                               34

SEQ ID NO: 72           moltype = RNA   length = 34
FEATURE                 Location/Qualifiers
misc_feature            1..34
                        note = Synthetic
misc_feature            1..34
                        note = L-nucleic acid
source                  1..34
                        mol_type = other RNA
                        organism = synthetic construct
SEQUENCE: 72
atgtggtggt gaggggttgt ggggtgtcga cgca                               34

SEQ ID NO: 73           moltype = DNA   length = 34
FEATURE                 Location/Qualifiers
misc_feature            1..34
                        note = Synthetic
misc_feature            1..34
                        note = L-nucleic acid
misc_feature            1..3
                        note = RNA
misc_feature            4
                        note = DNA
misc_feature            5..34
                        note = RNA
source                  1..34
                        mol_type = other DNA
                        organism = synthetic construct
SEQUENCE: 73
atgtggtggt gaagggttgt tgggtgtcga cgca                               34

SEQ ID NO: 74           moltype = DNA   length = 34
FEATURE                 Location/Qualifiers
```

```
misc_feature       1..34
                   note = Synthetic
misc_feature       1..34
                   note = L-nucleic acid
misc_feature       1..10
                   note = RNA
misc_feature       11
                   note = DNA
misc_feature       12..34
                   note = RNA
source             1..34
                   mol_type = other DNA
                   organism = synthetic construct
SEQUENCE: 74
atgtggtggt gaagggttgt tgggtgtcga cgca                                34

SEQ ID NO: 75      moltype = DNA  length = 34
FEATURE            Location/Qualifiers
misc_feature       1..34
                   note = Synthetic
misc_feature       1..34
                   note = L-nucleic acid
misc_feature       1..11
                   note = RNA
misc_feature       12
                   note = DNA
misc_feature       13..34
                   note = RNA
source             1..34
                   mol_type = other DNA
                   organism = synthetic construct
SEQUENCE: 75
atgtggtggt gaagggttgt tgggtgtcga cgca                                34

SEQ ID NO: 76      moltype = DNA  length = 34
FEATURE            Location/Qualifiers
misc_feature       1..34
                   note = Synthetic
misc_feature       1..34
                   note = L-nucleic acid
misc_feature       1..24
                   note = RNA
misc_feature       25
                   note = DNA
misc_feature       26..34
                   note = RNA
source             1..34
                   mol_type = other DNA
                   organism = synthetic construct
SEQUENCE: 76
atgtggtggt gaagggttgt tgggtgtcga cgca                                34

SEQ ID NO: 77      moltype = DNA  length = 34
FEATURE            Location/Qualifiers
misc_feature       1..34
                   note = Synthetic
misc_feature       1..34
                   note = L-nucleic acid
misc_feature       1..26
                   note = RNA
misc_feature       27
                   note = DNA
misc_feature       28..34
                   note = RNA
source             1..34
                   mol_type = other DNA
                   organism = synthetic construct
SEQUENCE: 77
atgtggtggt gaagggttgt tgggtgtcga cgca                                34

SEQ ID NO: 78      moltype = DNA  length = 34
FEATURE            Location/Qualifiers
misc_feature       1..34
                   note = Synthetic
misc_feature       1..34
                   note = L-nucleic acid
misc_feature       1..3
                   note = RNA
misc_feature       4
```

```
                        note = DNA
misc_feature            5..24
                        note = RNA
misc_feature            25
                        note = DNA
misc_feature            26..34
                        note = RNA
source                  1..34
                        mol_type = other DNA
                        organism = synthetic construct
SEQUENCE: 78
atgtggtggt gaagggttgt tgggtgtcga cgca                                   34

SEQ ID NO: 79           moltype = DNA  length = 34
FEATURE                 Location/Qualifiers
misc_feature            1..34
                        note = Synthetic
misc_feature            1..34
                        note = L-nucleic acid
misc_feature            1..3
                        note = RNA
misc_feature            4
                        note = DNA
misc_feature            5..26
                        note = RNA
misc_feature            27
                        note = DNA
misc_feature            28..34
                        note = RNA
source                  1..34
                        mol_type = other DNA
                        organism = synthetic construct
SEQUENCE: 79
atgtggtggt gaagggttgt tgggtgtcga cgca                                   34

SEQ ID NO: 80           moltype = DNA  length = 34
FEATURE                 Location/Qualifiers
misc_feature            1..34
                        note = Synthetic
misc_feature            1..34
                        note = L-nucleic acid
misc_feature            1..24
                        note = RNA
misc_feature            25
                        note = DNA
misc_feature            26
                        note = RNA
misc_feature            27
                        note = DNA
misc_feature            28..34
                        note = RNA
source                  1..34
                        mol_type = other DNA
                        organism = synthetic construct
SEQUENCE: 80
atgtggtggt gaagggttgt tgggtgtcga cgca                                   34

SEQ ID NO: 81           moltype = DNA  length = 34
FEATURE                 Location/Qualifiers
misc_feature            1..34
                        note = Synthetic
misc_feature            1..34
                        note = L-nucleic acid
misc_feature            1..3
                        note = RNA
misc_feature            4
                        note = DNA
misc_feature            5..24
                        note = RNA
misc_feature            25
                        note = DNA
misc_feature            26
                        note = RNA
misc_feature            27
                        note = DNA
misc_feature            28..34
                        note = RNA
source                  1..34
                        mol_type = other DNA
```

```
                            organism = synthetic construct
SEQUENCE: 81
atgtggtggt gaagggttgt tgggtgtcga cgca                               34

SEQ ID NO: 82           moltype = DNA   length = 34
FEATURE                 Location/Qualifiers
misc_feature            1..34
                        note = Synthetic
misc_feature            1..34
                        note = L-nucleic acid
misc_feature            1..3
                        note = RNA
misc_feature            4
                        note = DNA
misc_feature            5..10
                        note = RNA
misc_feature            11
                        note = DNA
misc_feature            12..24
                        note = RNA
misc_feature            25
                        note = DNA
misc_feature            26
                        note = RNA
misc_feature            27
                        note = DNA
misc_feature            28..34
                        note = RNA
source                  1..34
                        mol_type = other DNA
                        organism = synthetic construct
SEQUENCE: 82
atgtggtggt gaagggttgt tgggtgtcga cgca                               34

SEQ ID NO: 83           moltype = DNA   length = 34
FEATURE                 Location/Qualifiers
misc_feature            1..34
                        note = Synthetic
misc_feature            1..34
                        note = L-nucleic acid
misc_feature            1..3
                        note = RNA
misc_feature            4
                        note = DNA
misc_feature            5..11
                        note = RNA
misc_feature            12
                        note = DNA
misc_feature            13..24
                        note = RNA
misc_feature            25
                        note = DNA
misc_feature            26
                        note = RNA
misc_feature            27
                        note = DNA
misc_feature            28..34
                        note = RNA
source                  1..34
                        mol_type = other DNA
                        organism = synthetic construct
SEQUENCE: 83
atgtggtggt gaagggttgt tgggtgtcga cgca                               34

SEQ ID NO: 84           moltype = DNA   length = 34
FEATURE                 Location/Qualifiers
misc_feature            1..34
                        note = Synthetic
misc_feature            1..34
                        note = L-nucleic acid
misc_feature            1..3
                        note = RNA
misc_feature            4
                        note = DNA
misc_feature            5..10
                        note = RNA
misc_feature            11
                        note = DNA
misc_feature            12
```

```
                          note = DNA
misc_feature              13..24
                          note = RNA
misc_feature              25
                          note = DNA
misc_feature              26
                          note = RNA
misc_feature              27
                          note = DNA
misc_feature              28..34
                          note = RNA
source                    1..34
                          mol_type = other DNA
                          organism = synthetic construct
SEQUENCE: 84
atgtggtggt gaagggttgt tgggtgtcga cgca                              34

SEQ ID NO: 85             moltype = DNA  length = 44
FEATURE                   Location/Qualifiers
misc_feature              1..44
                          note = Synthetic
misc_feature              1..44
                          note = D-RNA
source                    1..44
                          mol_type = other DNA
                          organism = synthetic construct
SEQUENCE: 85
gcctgatgtg gtgttgaggg gctgtggggt gtcgacgcac aggc                   44

SEQ ID NO: 86             moltype = DNA  length = 44
FEATURE                   Location/Qualifiers
misc_feature              1..44
                          note = Synthetic
misc_feature              1..44
                          note = D-RNA
source                    1..44
                          mol_type = other DNA
                          organism = synthetic construct
SEQUENCE: 86
gcctgatgtg gtgttgaggg gttgtggggt gtcgacgcac aggc                   44

SEQ ID NO: 87             moltype = RNA  length = 44
FEATURE                   Location/Qualifiers
misc_feature              1..44
                          note = Synthetic
modified_base             1
                          mod_base = OTHER
                          note = Polyethylene glycol (PEG) attached
misc_feature              1..44
                          note = L-nucleic acid
source                    1..44
                          mol_type = other RNA
                          organism = synthetic construct
SEQUENCE: 87
cggacacgca gctgtgggtt gttgggaagt ggtggtgtag tccg                   44

SEQ ID NO: 88             moltype = DNA  length = 40
FEATURE                   Location/Qualifiers
misc_feature              1..40
                          note = Synthetic
modified_base             1
                          mod_base = OTHER
                          note = Polyethylene glycol (PEG) attached
misc_feature              1..40
                          note = L-nucleic acid
misc_feature              1..2
                          note = RNA
misc_feature              3
                          note = DNA
misc_feature              4..12
                          note = RNA
misc_feature              13
                          note = DNA
misc_feature              14..33
                          note = RNA
misc_feature              34
                          note = DNA
misc_feature              35..40
                          note = RNA
```

```
source                      1..40
                            mol_type = other DNA
                            organism = synthetic construct
SEQUENCE: 88
cgcacgcagc tgtgggttgt tgggaagtgg tggtgtagcg                              40

SEQ ID NO: 89               moltype = AA  length = 74
FEATURE                     Location/Qualifiers
SITE                        74
                            note = modified_base - Biotin attached
source                      1..74
                            mol_type = protein
                            organism = Mus musculus
SEQUENCE: 89
LLRQKIEEQA AKYKHSVPKK CCYDGARVNF YETCEERVAR VTIGPLCIRA FNECCTIANK        60
IRKESPHKPV QLGR                                                         74

SEQ ID NO: 90               moltype = RNA  length = 44
FEATURE                     Location/Qualifiers
misc_feature                1..44
                            note = Synthetic
modified_base               1
                            mod_base = OTHER
                            note = Polyethylene glycol (PEG) attached
misc_feature                1..44
                            note = L-nucleic acid
source                      1..44
                            mol_type = other RNA
                            organism = synthetic construct
SEQUENCE: 90
gcctgatgtg gtggtgaagg gttgttgggt gtcgacgcac aggc                         44

SEQ ID NO: 91               moltype = DNA  length = 40
FEATURE                     Location/Qualifiers
misc_feature                1..40
                            note = Synthetic
modified_base               1
                            mod_base = OTHER
                            note = Polyethylene glycol (PEG) attached
misc_feature                1..40
                            note = L-nucleic acid
misc_feature                1..6
                            note = RNA
misc_feature                7
                            note = DNA
misc_feature                8..13
                            note = RNA
misc_feature                14
                            note = DNA
misc_feature                15
                            note = DNA
misc_feature                16..27
                            note = RNA
misc_feature                28
                            note = DNA
misc_feature                29
                            note = RNA
misc_feature                30
                            note = DNA
misc_feature                31..37
                            note = RNA
misc_feature                38
                            note = DNA
misc_feature                39..40
                            note = RNA
source                      1..40
                            mol_type = other DNA
                            organism = synthetic construct
SEQUENCE: 91
gcgatgtggt ggtgaagggt tgttgggtgt cgacgcacgc                              40

SEQ ID NO: 92               moltype = DNA  length = 41
FEATURE                     Location/Qualifiers
misc_feature                1..41
                            note = Synthetic
modified_base               1
                            mod_base = OTHER
                            note = Polyethylene glycol (PEG) attached
misc_feature                1..40
```

```
                          note = L-nucleic acid
misc_feature              1..6
                          note = RNA
misc_feature              7
                          note = DNA
misc_feature              8..27
                          note = RNA
misc_feature              28
                          note = DNA
misc_feature              29..37
                          note = RNA
misc_feature              38
                          note = DNA
misc_feature              39..40
                          note = RNA
source                    1..41
                          mol_type = other DNA
                          organism = synthetic construct
SEQUENCE: 92
gcgatgtggt ggtgaagggt tgttgggtgt cgacgcacgc d                       41

SEQ ID NO: 93             moltype = AA  length = 73
FEATURE                   Location/Qualifiers
source                    1..73
                          mol_type = protein
                          organism = Homo sapiens
SEQUENCE: 93
TLQKKIEEIA AKYKHSVVKK CCYDGACVNN DETCEQRAAR ISLGPRCIKA FTECCVVASQ    60
LRANISHKDM QLG                                                      73

SEQ ID NO: 94             moltype = AA  length = 76
FEATURE                   Location/Qualifiers
source                    1..76
                          mol_type = protein
                          organism = Mus musculus
SEQUENCE: 94
NLHLLRQKIE EQAAKYKHSV PKKCCYDGAR VNFYETCEER VARVTIGPLC IRAFNECCTI    60
ANKIRKESPH KPVQLG                                                   76
```